(12) United States Patent
Adams et al.

(10) Patent No.: US 8,153,674 B2
(45) Date of Patent: Apr. 10, 2012

(54) ORGANIC COMPOUNDS

(75) Inventors: Christopher Adams, Somerville, MA (US); Julien Papillon, Somerville, MA (US); Gary Michael Ksander, Amherst, NH (US)

(73) Assignee: Novartis AG, Basel (CH)

( * ) Notice: Subject to any disclaimer, the term of this patent is extended or adjusted under 35 U.S.C. 154(b) by 603 days.

(21) Appl. No.: 12/295,155

(22) PCT Filed: Mar. 27, 2007

(86) PCT No.: PCT/US2007/064974
§ 371 (c)(1),
(2), (4) Date: Sep. 29, 2008

(87) PCT Pub. No.: WO2007/117982
PCT Pub. Date: Oct. 18, 2007

(65) Prior Publication Data
US 2009/0182007 A1    Jul. 16, 2009

Related U.S. Application Data

(60) Provisional application No. 60/787,104, filed on Mar. 29, 2006.

(51) Int. Cl.
C07D 405/02     (2006.01)
A61K 31/4178    (2006.01)

(52) U.S. Cl. .................. 514/397; 548/311.4

(58) Field of Classification Search .............. None
See application file for complete search history.

(56) References Cited

U.S. PATENT DOCUMENTS 4,904,300 A * 2/1990 Schneider et al. ............ 504/225

FOREIGN PATENT DOCUMENTS

EP        0305332 A      3/1989
WO    2006/008316 A      1/2006

OTHER PUBLICATIONS

Ehmer, et al., "Developent of a test system for inhibitors of human aldosterone synthase (CYP11B12): Screening in fission yeast and evaluation of selectivity in V79 cells" Journal of steroid biochemistry and molecular biology, vol. 81, No. 2, 2002, pp. 173-179.
Salmon, et al., "Plant sterol biosynthesis: novel potent and selective inhibitors of cytochrome p-450-dependent obtusifoliol 14. alpha-methyl demethylase" Archives of biochemistry and biophysics, 297(1), 1992 pp. 123-131.
Ulmschneider, et al., "Development and evaluation of a pharmacophore model for inhibitors of aldosterone synthase (CYP11B2)" Bioorganic & medicinal chemistry letters, vol. 16, No. 1, 2006, pp. 25-30.
Muller-Vieira, et al., "The adrenocortisol tumor cell line NCI-H295R as an in vitro screening system for the evaluation of CYP11B2 (aldosterone synthase) and CYP11B1 (steroid 11 beta hydroxylase) inhibitors" Journal of steroid biochemistry and molecular biology, vol. 96, No. 3-4, 2005, pp. 259-270.
U.S. Appl. No. 12/519,697, filed Jun. 17, 2009 in the name of Novartis AG.
U.S. Appl. No. 12/519,703, filed Jun. 17, 2009 in the name of Novartis AG.
U.S. Appl. No. 12/519,707, filed Jun. 17, 2009 in the name of Novartis AG.
Voets M et al: "Heteroaryl-substituted naphthalenes and structurally modified derivatives: selective inhibitors of CYP11B2 for the treatment of congestive heart failure and myocardial fibrosis" Journal of Medicinal Chemistry, American Chemical Society. Washington, US, vol. 48, No. 21, Sep. 22, 2005, pp. 6632-6642. table 1; compounds 20, 21.

* cited by examiner

*Primary Examiner* — Zinna Northington Davis
(74) *Attorney, Agent, or Firm* — Ann R. Pokalsky, Esq.; Dilworth & Barrese, LLP

(57) ABSTRACT

The present invention provides a compound of formula (I):

(I)

[chemical structure of formula (I) with substituents $R^1$, $R^2$, $R^3$, $R^4$, $R^5$, $R^6$, $R^7$, $R^8$, and X]

said compound is inhibitor of aldosterone synthase, and thus can be employed for the treatment of a disorder or disease mediated by aldosterone synthase. Accordingly, the compound of formula I can be used in treatment of hypokalemia, hypertension, congestive heart failure, renal failure, in particular, chronic renal failure, restenosis, atherosclerosis, syndrome X, obesity, nephropathy, post-myocardial infarction, coronary heart diseases, increased formation of collagen, cardiac fibrosis and remodeling following hypertension and endothelial dysfunction. Finally, the present invention also provides a pharmaceutical composition.

12 Claims, No Drawings

ORGANIC COMPOUNDS

This application is the National Stage of Application No. PCT/US07/64974 filed Mar. 27, 2007, which claims benefit under 35 U.S.C. §119(e) of U.S. Provisional Application No. 60/787,104, filed Mar. 29, 2006, the contents of which are incorporated herein by reference in their entirety.

The present invention relates to novel imidazole derivatives that are used as aldosterone synthase inhibitors, as well as for treatment of a disorder or disease mediated by aldosterone synthase (CYP11B2) and/or 11-beta-hydroxylase (CYP11B1)

In one embodiment, the present invention provides a compound of formula (I):

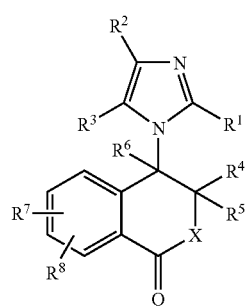

Wherein

X is oxygen or N—$R^9$;

$R^1$ is hydrogen, halogen, thiol, ($C_3$-$C_7$) cycloalkyl, aryl, heteroaryl, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_3$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^2$ is hydrogen, halogen, ($C_3$-$C_7$) cycloalkyl, aryl, heteroaryl, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_3$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^3$ is hydrogen, halogen, cyano, ($C_1$-$C_7$) alkenyl, ($C_1$-$C_7$) alkynyl, ($C_1$-$C_7$) alkyl-$SO_2$—, ($C_1$-$C_7$) alkoxy$SO_2$—, sulfonamido, aryl, heteroaryl, H($R^{10}$ON=)C—, $R^{10}$O($CH_2$)$_n$—, $R^{12}R^{11}(R^{13}O)$C—, $R^{14}$O—(O)C— or $R^{15}$—C(O)—; or $R^3$ is ($C_1$-$C_7$) alkyl that is optionally substituted by one to four substituents selected from halogen, mono-($C_1$-$C_7$) alkylamino, di-($C_1$-$C_7$) alkylamino; or $R^2$ and $R^3$ taken together with the carbon atoms to which they are attached optionally form a 5-9 membered ring;

$R^4$ and $R^5$ are independently hydrogen, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_3$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl; or $R^4$ and $R^5$ taken together with the carbon atom to which they are attached to optionally form a 4-9 membered ring;

$R^6$ is hydrogen, aryl, heteroaryl, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_1$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^7$ and $R^8$ are independently ($C_1$-$C_7$) alkyl or ($C_3$-$C_7$) cycloalkyl, each of which are optionally substituted by one to four substituents selected from hydroxy, ($C_1$-$C_7$) alkyl, halogen, ($C_1$-$C_7$) alkoxy, nitro, cyano, carboxy, thiol, ($C_3$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl; or $R^7$ and $R^8$ are independently hydrogen, halogen, cyano, nitro, mono-($C_1$-$C_7$) alkylamino, di-($C_1$-$C_7$) alkylamino, aryl, heteroaryl, $R^{16}$—O—, $R^{16}$—S—, $R^{17}$—C(O)—, or $R^{17}$—$SO_2$—;

n is 1, 2, 3, or 4;

$R^9$, $R^{10}$, $R^{11}$, $R^{12}$ and $R^{13}$ are independently hydrogen, ($C_3$-$C_7$) cycloalkyl, aryl, heteroaryl, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_1$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^{14}$ is hydrogen, ($C_3$-$C_7$) alkyl, ($C_3$-$C_7$) cycloalkyl, aryl, heteroaryl, or ($C_3$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_1$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^{15}$ is hydrogen, ($C_2$-$C_7$) alkyl, amino, mono-($C_1$-$C_7$) alkylamino, di-($C_1$-$C_7$) alkylamino, arylamino, diarylamino, aryl-mono-($C_1$-$C_7$) alkylamino;

$R^{16}$ is hydrogen, ($C_1$-$C_7$) alkyl, aryl, or ($C_1$-$C_4$) haloalkyl, and $R^{17}$ is amino, hydroxy, mono-($C_1$-$C_7$) alkylamino, di-($C_1$-$C_7$) alkylamino, or ($C_1$-$C_7$) alkoxy; or pharmaceutically acceptable salts thereof; or an optical isomer thereof; or a mixture of optical isomers.

In another embodiment, the present invention provides the compound of formula (I), wherein X is oxygen or N—$R^9$;

$R^1$ is hydrogen, halogen, thiol, ($C_3$-$C_7$) cycloalkyl, ($C_6$-$C_{10}$) aryl, (5-10)-membered heteroaryl, or ($C_1$-$C_4$) alkyl that is optionally substituted by one to four substituents selected from hydroxy, ($C_1$-$C_4$) alkyl, halogen, ($C_1$-$C_4$) alkoxy, amino, mono-($C_1$-$C_4$) alkylamino, or di-($C_1$-$C_4$) alkylamino;

$R^2$ is hydrogen, halogen, ($C_3$-$C_7$) cycloalkyl, ($C_6$-$C_{10}$) aryl, (5-10)-membered heteroaryl, or ($C_1$-$C_4$) alkyl that is optionally substituted by one to four substituents selected from hydroxy, ($C_1$-$C_4$) alkyl, halogen, ($C_1$-$C_4$) alkoxy, amino, mono-($C_1$-$C_4$) alkylamino, or di-($C_1$-$C_4$) alkylamino;

$R^3$ is hydrogen, halogen, cyano, ($C_6$-$C_{10}$) aryl, (5-10)-membered heteroaryl, $R^{10}$O($CH_2$)$_n$—, —, $R^{12}R^{11}(R^{13}O)$C—, $R^{14}$O—(O)C—, $R^{15}$—C(O)—, or ($C_1$-$C_4$) alkyl that is optionally substituted by one to four substituents selected from halogen, mono-($C_1$-$C_4$) alkylamino, di-($C_1$-$C_4$) alkylamino; or R² and R³ taken together with the carbon atoms to which they are attached optionally form a 5-9 membered ring;

R⁴ and R⁵ are independently hydrogen, or (C₁-C₄) alkyl that is optionally substituted by one to four substituents selected from hydroxy, (C₁-C₄) alkyl, halogen, (C₁-C₄) alkoxy, amino, mono-(C₁-C₄) alkylamino, or di-(C₁-C₄) alkylamino; or R⁴ and R⁵ taken together with the carbon atom to which they are attached to optionally form a 4-9 membered ring;

R⁶ is hydrogen, aryl, or (C₁-C₄) alkyl that is optionally substituted by one to four substituents selected from hydroxy, (C₁-C₄) alkyl, halogen, (C₁-C₄) alkoxy, amino, mono-(C₁-C₄) alkylamino, or di-(C₁-C₄) alkylamino;

R⁷ and R³ are independently hydrogen, halogen, cyano, nitro, R¹⁶—O—, R¹⁶—S—, R¹⁷—C(O)—, or R¹⁷—SO₂—, (C₁-C₄) alkyl or (C₃-C₇) cycloalkyl, each of which are optionally substituted by one to four substituents selected from hydroxy, halogen, nitro, cyano, carboxy, thiol, (C₃-C₇) cycloalkyl, amino, mono-(C₁-C₄) alkylamino, di-(C₁-C₄) alkylamino;

n is 1, 2, 3, or 4;

R⁹, R¹⁰, R¹¹, R¹² and R¹³ are independently hydrogen, (C₃-C₇) cycloalkyl, (C₆-C₁₀) aryl, (5-10)-membered heteroaryl, or (C₁-C₄) alkyl that is optionally substituted by one to four substituents selected from hydroxy, halogen, (C₁-C₄) alkoxy, (C₃-C₇) cycloalkyl, amino, mono-(C₁-C₄) alkylamino, di-(C₁-C₄) alkylamino, (C₆-C₁₀) aryl, (5-10)-membered heteroaryl;

R¹⁴ is (C₃-C₇) alkyl, (C₃-C₇) cycloalkyl, (C₉-C₁₀) aryl, (5-10)-membered heteroaryl, or (C₁-C₄) alkyl that is optionally substituted by one to four substituents selected from hydroxy, halogen, (C₁-C₄) alkoxy, amino, mono-(C₁-C₄) alkylamino, di-(C₁-C₄) alkylamino, (C₆-C₁₀) aryl, (5-10)-membered heteroaryl;

R¹⁵ is hydrogen, (C₂-C₄) alkyl, amino, mono-(C₁-C₄) alkylamino, di-(C₁-C₄) alkylamino, arylamino, diarylamino, aryl-mono-(C₁-C₄) alkylamino R¹⁶ is hydrogen, (C₁-C₄) alkyl, aryl, or (C₁-C₄) haloalkyl, and R¹⁷ is amino, hydroxy, mono-(C₁-C₄) alkylamino, di-(C₁-C₄) alkylamino, or (C₁-C₄) alkoxy; or pharmaceutically acceptable salts thereof; or an optical isomer thereof; or a mixture of optical isomers.

In another embodiment, the present invention provides a compound of formula (I):

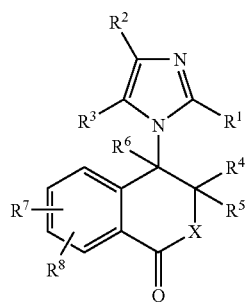

(I)

Wherein
X is N—R⁹ or oxygen;
R¹ is hydrogen;
R² is hydrogen;
R³ is cyano, R¹⁰—N(R¹⁸)—C(O)—, R¹²R¹¹(R¹³O)C—, R¹⁴—(O)C—, or R¹⁵—C(O)—; or
R⁴ and R⁵ are independently (C₁-C₄) alkyl; or R⁴ and R⁵ taken together with the carbon atom to which they are attached to optionally form a 3-9 membered ring;
R⁶ is hydrogen;
R⁷ is hydrogen;
R⁸ is hydrogen, cyano, or halogen;
R⁹ is hydrogen, benzyl, or C₁-C₄ alkyl;
R¹⁰ is C₁-C₄ alkyl, phenyl, or benzyl;
R¹¹ and R¹² are independently hydrogen;
R¹³ is hydrogen or (C₁-C₆) alkyl;
R¹¹ is C₃-C₆ alkyl;
R¹⁵ is (C₁-C₆) alkyl; or
R¹⁸ is hydrogen or C₁-C₄ alkyl, or
pharmaceutically acceptable salts thereof; or an optical isomer thereof; or a mixture of optical isomers.

In another embodiment, the present invention provides a compound of formula (I):
wherein
X is oxygen;
R¹ is hydrogen;
R² is hydrogen;
R³ is R¹²R¹¹(R¹³O)C—, R¹⁴O—(O)C—, or R¹⁵—C(O)—;
R⁴ and R⁵ are independently (C₁-C₄) alkyl;
R⁶ is hydrogen;
R⁷ is hydrogen;
R⁸ is hydrogen, or halogen;
R¹¹ and R¹² are independently hydrogen;
R¹³ is hydrogen or (C₁-C₆) alkyl;
R¹⁴ is C₃-C₆ alkyl;
R¹⁵ is (C₁-C₆) alkyl; or
pharmaceutically acceptable salts thereof; or an optical isomer thereof; or a mixture of optical isomers.

In another embodiment, the present invention provides a compound of formula (I):

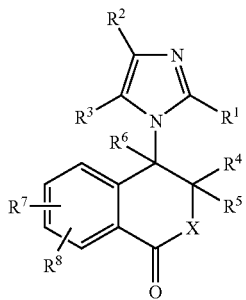

(I)

wherein
X is N—R⁹ or oxygen;
R¹ is hydrogen, halogen, thiol, or (C₁-C₇) alkyl;
R² is hydrogen, halogen, or (C₁-C₇) alkyl;
R³ is hydrogen, halogen, cycloalkyl, (C₁-C₇) alkenyl, heteroaryl, 4-10 membered heterocyclyl optionally substituted by one to four (C₁-C₇) alkyl, wherein said heterocyclyl having at least 3 hetero atoms, R¹⁰—N(R¹⁸)—C(O)—, H(R¹⁸ON=)C—, R¹⁰O(CH₂)ₙ—, or R¹⁴O—(O)C—; or R³ is hydrogen, halogen, cycloalkyl, (C₁-C₇) alkenyl, heteroaryl, 4-10 membered heterocyclyl optionally substituted by one to four (C₁-C₇) alkyl, wherein said heterocyclyl having at least 3 hetero atoms, R¹⁰—N(R¹⁸)—C(O)—, H(R¹⁸ON=)C—, R¹⁰O(CH₂)ₙ—, or R¹⁴O—(O)C—;

R³ is (C₂-C₇) alkyl substituted by hydroxy or (C₁-C₇) alkoxy, or (C₁-C₇) alkyl substituted by (C₁-C₇) alkoxy which is further substituted by one to four hydroxy; or $R^3$ is $(C_1-C_7)$ alkyl that is optionally substituted by one to four substituents selected from halogen, amino, mono-$(C_1-C_7)$ alkylamino, and di-$(C_1-C_7)$ alkylamino; or $R^2$ and $R^3$ taken together with the carbon atoms to which they are attached optionally form a 5-9 membered ring;

$R^4$ and $R^5$ are independently hydrogen, aryl, or $(C_1-C_7)$ alkyl, wherein said aryl or alkyl is optionally substituted by one to four substituents selected from hydroxy, $(C_1-C_7)$ alkyl, halogen, $(C_1-C_7)$ alkoxy, nitro, cyano, carboxy, thiol, $(C_3-C_7)$ cycloalkyl, $(C_1-C_7)$ alkenyl, $(C_1-C_7)$ alkynyl, amino, mono-$(C_1-C_7)$ alkylamino, di-$(C_1-C_7)$ alkylamino, aryl, heteroaryl, $(C_1-C_7)$ alkyl-C(O)—O—, $(C_1-C_7)$ alkyl-C(O)—, $(C_1-C_7)$ alkyl-O—C(O)—, acylamino, guanidino; or heterocyclyl; or $R^4$ and $R^5$, or $R^3$ and $R^4$ taken together with the carbon atom to which they are attached to optionally form a 4-9 membered ring;

$R^6$ is hydrogen, aryl, heteroaryl, or $(C_1-C_7)$ alkyl that is optionally substituted by one to four substituents selected from hydroxy, $(C_1-C_7)$ alkyl, halogen, $(C_1-C_7)$ alkoxy, nitro, cyano, carboxy, thiol, $(C_1-C_7)$ cycloalkyl, $(C_1-C_7)$ alkenyl, $(C_1-C_7)$ alkynyl, amino, mono-$(C_1-C_7)$ alkylamino, di-$(C_1-C_7)$ alkylamino, aryl, heteroaryl, $(C_1-C_7)$ alkyl-C(O)—O—, $(C_1-C_7)$ alkyl-C(O)—, $(C_1-C_7)$ alkyl-O—C(O)—, acylamino, guanidino, or heterocyclyl;

$R^7$ and $R^8$ are independently $(C_1-C_7)$ alkyl or $(C_3-C_7)$ cycloalkyl, each of which are optionally substituted by one to four substituents selected from hydroxy, $(C_1-C_7)$ alkyl, halogen, $(C_1-C_7)$ alkoxy, nitro, cyano, carboxy, thiol, $(C_3-C_7)$ cycloalkyl, $(C_1-C_7)$ alkenyl, $(C_1-C_7)$ alkynyl, amino, mono-$(C_1-C_7)$ alkylamino, di-$(C_1-C_7)$ alkylamino, aryl, heteroaryl, $(C_1-C_7)$ alkyl-C(O)—O—, $(C_1-C_7)$ alkyl-C(O)—, $(C_1-C_7)$ alkyl-O—C(O)—, acylamino, guanidino, or heterocyclyl; or $R^7$ and $R^8$ are independently hydrogen, halogen, cyano, nitro, mono-$(C_1-C_7)$ alkylamino, di-$(C_1-C_7)$ alkylamino, aryl, heteroaryl, $R^{16}$—O—, $R^{18}$—S—, $R^{17}$—C(O)—, or $R^{17}$—SO$_2$—;

$R^9$ is hydrogen, $(C_3-C_7)$ cycloalkyl, cyano, aralkyl, or $(C_1-C_7)$ alkyl that is optionally substituted by one to four halogen;

$R^{10}$ is aralkyl substituted by one to four substituents selected from hydroxy, $(C_1-C_7)$ alkyl, or halogen, heteroaryl optionally substituted by one to four substituents selected from hydroxy, $(C_1-C_7)$ alkyl, or halogen, or $(C_1-C_7)$ alkyl substituted by one to four hydroxy;

$R^{14}$ is aryl optionally substituted by one to four substituents selected from hydroxy, $(C_1-C_7)$ alkyl, halogen, $(C_1-C_7)$ alkoxy, nitro, cyano, carboxy, thiol, $(C_1-C_7)$ cycloalkyl, $(C_1-C_7)$ alkenyl, $(C_1-C_7)$ alkynyl, amino, mono-$(C_1-C_7)$ alkylamino, di-$(C_1-C_7)$ alkylamino, aryl, heteroaryl, $(C_1-C_7)$ alkyl-C(O)—O—, $(C_1-C_7)$ alkyl-C(O)—, $(C_1-C_7)$ alkyl-O—C(O)—, acylamino, guanidino, or heterocyclyl;

$R^{16}$ is hydrogen, $(C_1-C_7)$ alkyl, aryl, or $(C_1-C_4)$ haloalkyl, $R^{17}$ is amino, hydroxy, mono-$(C_1-C_7)$ alkylamino, di-$(C_1-C_7)$ alkylamino, 4-10 membered heterocyclyl, or $(C_1-C_7)$ alkoxy;

$R^{18}$ is hydrogen or $(C_1-C_7)$ alkyl; or n is 2, 3, or 4;

pharmaceutically acceptable salts thereof; or an optical isomer thereof; or a mixture of optical isomers.

In another embodiment, the present invention further provides a compound of formula (I):

X is oxygen or N—$R^9$ $R^1$ is hydrogen, or $(C_1-C_7)$ alkyl;

$R^2$ is hydrogen, or $(C_1-C_7)$ alkyl;

$R^3$ is hydrogen, halogen, cycloalkyl, or $(C_1-C_7)$ alkenyl;

$R^4$ and $R^5$ are independently hydrogen, aryl, or $(C_1-C_7)$ alkyl;

$R^6$ is hydrogen, aryl, heteroaryl, or $(C_1-C_7)$ alkyl;

$R^7$ and $R^8$ are independently hydrogen, halogen, cyano, or nitro;

$R^9$ is hydrogen, or $(C_1-C_7)$ alkyl; or pharmaceutically acceptable salts thereof; or an optical isomer thereof; or a mixture of optical isomers.

In another embodiment, the present invention provides a compound of formula (I):

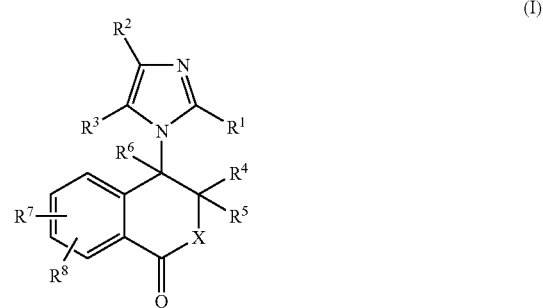

wherein

X is N—$R^9$;

$R^1$ is hydrogen, halogen, thiol, or $(C_1-C_7)$ alkyl;

$R^2$ is hydrogen, halogen, or $(C_1-C_7)$ alkyl;

$R^3$ is $(C_1-C_7)$alkyl-O—(O)C—;

$R^4$ and $R^5$ are independently hydrogen, aryl, or $(C_1-C_7)$ alkyl, wherein said aryl or alkyl is optionally substituted by one to four substituents selected from hydroxy, $(C_1-C_7)$ alkyl, halogen, $(C_1-C_7)$ alkoxy, nitro, cyano, carboxy, thiol, $(C_3-C_7)$ cycloalkyl, $(C_1-C_7)$ alkenyl, $(C_1-C_7)$ alkynyl, amino, mono-$(C_1-C_7)$ alkylamino, di-$(C_1-C_7)$ alkylamino, aryl, heteroaryl, $(C_1-C_7)$alkyl-C(O)—O—, $(C_1-C_7)$alkyl-C(O)—, $(C_1-C_7)$ alkyl-O—C(O)—, acylamino, guanidino, or heterocyclyl; or $R^4$ and $R^5$, or $R^3$ and $R^4$ taken together with the carbon atom to which they are attached to optionally form a 4-9 membered ring;

$R^6$ is hydrogen, aryl, heteroaryl, or $(C_1-C_7)$ alkyl that is optionally substituted by one to four substituents selected from hydroxy, $(C_1-C_7)$ alkyl, halogen, $(C_1-C_7)$ alkoxy, nitro, cyano, carboxy, thiol, $(C_1-C_7)$ cycloalkyl, $(C_1-C_7)$ alkenyl, $(C_1-C_7)$ alkynyl, amino, mono-$(C_1-C_7)$ alkylamino, di-$(C_1-C_7)$ alkylamino, aryl, heteroaryl, $(C_1-C_7)$ alkyl-C(O)—O—, $(C_1-C_7)$ alkyl-C(O)—, $(C_1-C_7)$ alkyl-O—C(O)—, acylamino, guanidino, or heterocyclyl;

$R^7$ and $R^8$ are independently hydrogen or $(C_1-C_7)$ alkyl;

$R^9$ is $(C_3-C_7)$ cycloalkyl;

pharmaceutically acceptable salts thereof; or an optical isomer thereof; or a mixture of optical isomers.

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. When an alkyl group includes one or more unsaturated bonds, it can be referred to as an alkenyl (double bond) or an alkynyl (triple bond) group.

The term "aryl" refers to monocyclic or bicyclic aromatic hydrocarbon groups having 6-20 carbon atoms in the ring portion. Preferably, the aryl is a ($C_6$-$C_{10}$) aryl. Non-limiting examples include phenyl, biphenyl, naphthyl or tetrahydronaphthyl, each of which may optionally be substituted by 1-4 substituents, such as alkyl, trifluoromethyl, cycloalkyl, halogen, hydroxy, alkoxy, acyl, alkyl-C(O)—O—, aryl-O—, heteroaryl-O—, amino, thiol, alkyl-S—, aryl-S—, nitro, cyano, carboxy, alkyl-O—C(O)—, carbamoyl, alkyl-S(O)—, sulfonyl, sulfonamido, heterocyclyl and the like, wherein R is independently hydrogen, alkyl, aryl, heteroaryl, aryl-alkyl-, heteroaryl-alkyl- and the like.

Furthermore, the term "aryl" as used herein, refers to an aromatic substituent which can be a single aromatic ring, or multiple aromatic rings that are fused together, linked covalently, or linked to a common group such as a methylene or ethylene moiety. The common linking group also can be a carbonyl as in benzophenone or oxygen as in diphenylether or nitrogen as in diphenylamine.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-7, more preferably about 1-4 carbons.

As used herein, the term "acyl" refers to a group R—C(O)— of from 1 to 10 carbon atoms of a straight, branched, or cyclic configuration or a combination thereof, attached to the parent structure through carbonyl functionality. Such group can be saturated or unsaturated, and aliphatic or aromatic. Preferably, R in the acyl residue is alkyl, or alkoxy, or aryl, or heteroaryl. Also preferably, one or more carbons in the acyl residue may be replaced by nitrogen, oxygen or sulfur as long as the point of attachment to the parent remains at the carbonyl. Examples include but are not limited to, acetyl, benzoyl, propionyl, isobutyryl, t-butoxycarbonyl, benzyloxycarbonyl and the like. Lower acyl refers to acyl containing one to four carbons.

As used herein, the term "acylamino" refers to acyl-NH—, wherein "acyl" is defined herein.

As used herein, the term "carbamoyl" refers to $H_2NC(O)$—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aryl-alkyl-NHC(O)—, alkyl(aryl-alkyl)-NC(O)— and the like.

As used herein, the term "sulfonyl" refers to R—$SO_2$—, wherein R is hydrogen, alkyl, aryl, heretoaryl, aryl-alkyl, heteroaryl-alkyl, aryl-O—, heteroaryl-O—, alkoxy, aryloxy, cycloalkyl, or heterocyclyl.

As used herein, the term "sulfonamido" refers to alkyl-S(O)$_2$—NH—, aryl-S(O)$_2$—NH—, aryl-alkyl-S(O)$_2$—NH—, heteroaryl-S(O)$_2$—NH—, heteroaryl-alkyl-S(O)$_2$—NH—, alkyl-S(O)$_2$—N (alkyl)-, aryl-S(O)$_2$—N(alkyl)-, aryl-alkyl-S(O)$_2$—N(alkyl)-, heteroaryl-S(O)$_2$—N(alkyl)-, heteroaryl-alkyl-S(O)$_2$—N(alkyl)- and the like.

As used herein, the term "heterocyclyl" or "heterocyclo" refers to an optionally substituted, saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include tetrahydrofuran(THF), dihydrofurari, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

The term "heterocyclyl" further refers to heterocyclic groups as defined herein substituted with 1, 2 or 3 substituents selected from the groups consisting of the following:
(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxy;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "cycloalkyl" refers to optionally substituted saturated or unsaturated monocyclic, bicyclic or tricyclic hydrocarbon groups of 3-12 carbon atoms, each of which may be substituted by one or more substituents, such as alkyl, halo, oxo, hydroxy, alkoxy, alkyl-C(O)—, acylamino, carbamoyl, alkyl-NH—, (alkyl)$_2$N—, thiol, alkylthio, nitro, cyano, carboxy, alkyl-O—C(O)—, sulfonyl, sulfonamido, sulfamoyl, heterocyclyl and the like. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "sulfamoyl" refers to $H_2NS(O)_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.

As used herein, the term "aryloxy" refers to both an —O-aryl and an —O— heteroaryl group, wherein aryl and heteroaryl are defined herein.

As used herein, the term "heteroaryl" refers to a 5-14 membered monocyclic- or bicyclic- or fused polycyclic-ring system, having 1 to 8 heteroatoms selected from N, O or S. Preferably, the heteroaryl is a 5-10 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoquinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

A heteroaryl group may be mono-, bi-, tri-, or polycyclic, preferably mono-, bi-, or tricyclic, more preferably mono- or bicyclic.

As used herein, the term "halogen" or "halo" refers to fluoro, chloro, bromo, and iodo.

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Preferably, the polyhaloalkyl contains up to 12, 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

As used herein, the term "isomers" refers to different compounds that have the same molecular formula. Also as used herein, the term "an optical isomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in *Remington's Pharmaceutical Sciences*, 20th ed., Mack Publishing Company, Easton, Pa., (1985), which is herein incorporated by reference.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The term "therapeutically effective amount" of a compound of the present invention refers to an amount of the compound of the present invention that will elicit the biological or medical response of a subject, or ameliorate symptoms, slow or delay disease progression, or prevent a disease, etc. In a preferred embodiment, the "effective amount" refers to the amount that inhibits or reduces expression of either aldosterone synthase.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "a disorder" or "a disease" refers to any derangement or abnormality of function; a morbid physical or mental state. See *Dorland's Illustrated Medical Dictionary*, (W. B. Saunders Co. 27th ed. 1988).

As used herein, the term "inhibition" or "inhibiting" refers to the reduction or suppression of a given condition, symptom, or disorder, or disease, or a significant decrease in the baseline activity of a biological activity or process. Preferably, the condition or symptom or disorder or disease is mediated by aldosterone synthase activity. More preferably, the condition or symptom or disorder or disease is associated with the abnormal activity of aldosterone synthase or the abnormal biological activity of aldosterone synthase, or the condition or symptom or disorder or disease is associated with the abnormal expression of aldosterone synthase.

As used herein, the term "treating" or "treatment" of any disease or disorder refers in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "abnormal" refers to an activity or feature which differs from a normal activity or feature.

As used herein, the term "abnormal activity" refers to an activity which differs from the activity of the wild-type or native gene or protein, or which differs from the activity of the gene or protein in a healthy subject. The abnormal activity can be stronger or weaker than the normal activity. In one embodiment, the "abnormal activity" includes the abnormal (either over- or under-) production of mRNA transcribed from a gene. In another embodiment, the "abnormal activity" includes the abnormal (either over- or under-) production of polypeptide from a gene. In another embodiment, the abnormal activity refers to a level of a mRNA or polypeptide that is different from a normal level of said mRNA or polypeptide by about 15%, about 25%, about 35%, about 50%, about 65%, about 85%, about 100% or greater. Preferably, the abnormal level of the mRNA or polypeptide can be either higher or lower than the normal level of said mRNA or polypeptide. Yet in another embodiment, the abnormal activity refers to functional activity of a protein that is different from a normal activity of the wild-type protein. Preferably, the abnormal activity can be stronger or weaker than the normal activity. Preferably, the abnormal activity is due to the mutations in the corresponding gene, and the mutations can be in the coding region of the gene or non-coding regions such as transcriptional promoter regions. The mutations can be substitutions, deletions, insertions.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein are merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Any asymmetric carbon atom on the compounds of the present invention can be present in the (R)-, (S)- or (R,S)-configuration, preferably in the (R)- or (S)-configuration. Substituents at atoms with unsaturated bonds may, if possible, be present in cis-(Z)- or trans-(F)-form. Therefore, the compounds of the present invention can be in the form of one of the possible isomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, the imidazolyl moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Finally, compounds of the present invention are either obtained in the free form, as a salt thereof, or as prodrug derivatives thereof.

When a basic group is present in the compounds of the present invention, the compounds can be converted into acid addition salts thereof, in particular, acid addition salts with the imidazolyl moiety of the structure, preferably pharmaceutically acceptable salts thereof. These are formed, with inorganic acids or organic acids. Suitable inorganic acids include but are not limited to, hydrochloric acid, sulfuric acid, a phosphoric or hydrohalic acid. Suitable organic acids include but are not limited to, carboxylic acids, such as ($C_1$-$C_4$)alkanecarboxylic acids which, for example, are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, organic sulfonic acids, such as ($C_1$-$C_4$)alkylsulfonic acids, e.g., methanesulfonic acid; or arylsulfonic acids which are unsubstituted or substituted, e.g., by halogen. Preferred are salts formed with hydrochloric acid, methanesulfonic acid and maleic acid.

When an acidic group is present in the compounds of the present invention, the compounds can be converted into salts with pharmaceutically acceptable bases. Such salts include alkali metal salts, like sodium, lithium and potassium salts; alkaline earth metal salts, like calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids like arginine, lysine and the like. Salts may be formed using conventional methods, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also be used for purification of the compounds obtained.

When both a basic group and an acid group are present in the same molecule, the compounds of the present invention can also form internal salts.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds are inactive or have low activity compared to the corresponding active drug compound, that contains one or more protective groups and are converted to an active form by metabolism or solvolysis. Both the active drug form and any released metabolic products should have acceptably low toxicity. Typically, the formation of active drug compound involves a metabolic process or reaction that is one of the follow types:

1. Oxidative reactions, such as oxidation of alcohol, carbonyl, and acid functions, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

2. Reductive reactions, such as reduction of carbonyl groups, reduction of alcoholic groups and carbon-carbon double bonds, reduction of nitrogen-containing functions groups, and other reduction reactions.

3. Reactions without change in the state of oxidation, such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. See, Cheng et al., US20040077595, application Ser. No. 10/656, 838, incorporated herein by reference. Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, *The Practice of Medicinal Chemistry*, Ch. 31-32, Ed. Werriuth, Academic Press, San Diego, Calif., 2001.

Exemplary prodrugs are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)).

Hydroxy groups have been masked as esters and ethers. EP 039,051 (Sloan and Little) discloses Mannich-base hydroxamic acid prodrugs, their preparation and use.

In view of the close relationship between the compounds, the compounds in the form of their salts and the pro-drugs, any reference to the compounds of the present invention is to be understood as referring also to the corresponding pro-drugs of the compounds of the present invention, as appropriate and expedient.

Furthermore, the compounds of the present invention, including their salts, can also be obtained in the form of their hydrates, or include other solvents used for their crystallization.

The compounds of the present invention have valuable pharmacological properties.

The compounds of the present invention are useful as aldosterone synthase inhibitors. Aldosterone synthase (CYP11B2) is a mitcohcondrial cytochrome P450 enzyme catalyzing the last step of aidosterone production in the adrenal cortex, i.e., the conversion of 11-deoxycorticosterone to aldosterone. Aldosterone synthase has been demonstrated to be expressed in all cardiovascular tissues such as heart, umbilical cord, mesenteric and pulmonary arteries, aorta, endothelium and vascular cells. Moreover, the expression of aldosterone synthase is closely correlated with aldosterone production in cells. It has been observed that elevations of aldosterone activities or aldosterone levels induce different diseases such as congestive heart failure, cardiac or myocardial fibrosis, renal failure, hypertension, ventricular arrhythmia and other adverse effects, etc., and that the inhibition of aldosterone or aldosterone synthase would be useful therapeutic approaches. See e.g., Ulmschenider et al. "Development and evaluation of a pharmacophore model for inhibitors of aldosterone synthase (CYP11B2)," *Bioorganic & Medicinal Chemistry Letters,* 16: 25-30 (2006); Bureik et al., "Development of test systems for the discovery of selective human aldosterone synthase (CYP11B2) and 11β-hydroxylase (CYP11B1) inhibitors, discovery of a new lead compound for the therapy of congestive heart failure, myocardial fibrosis and hypertension," *Moleculare and Cellular Endocrinology,* 217: 249-254 (2004); Bos et al., "Inhibition of catechnolamine-induced cardiac fibrosis by an aldosteron antagonist," *J. Cardiovascular Pharmacol,* 45(1): 8-13 (2005); Jaber and Madias, "Progression of chronic kidney disease: can it be prevented or arrested?" *Am. J. Med.* 118 (121: 1323-1330 (2005); Khan and Movahed, "The role of aldosterone and aldosterone-receptor antagonists in heart failure," *Rev. Cardiovasc Med.,* 5(2): 71-81 (2004); Struthers, "Aldosterone in heart failure: pathophysiology and treatment," *Cyrr. Heart Fail.,* 1(4): 171-175 (2004); Harris and Rangan, "Retardation of kidney failure—applying principles to practice,"*Ann. Acad. Med. Singapore,* 34(1): 16-23 (2005); Arima, "Aldosterone and the kidney: rapid regulation of renal microcirculation," *Steroids,* online publication November 2005; Brown, "Aldosterone and end-organ damage," *Curr. Opin. Nephrol Hypertens,* 14:235-241 (2005); Grandi, "Antihypertensive therapy: role of aldosteron antagonists," *Curr. Pharmaceutical Design,* 11: 2235-2242 (2005); Declayre and Swynghedauw, "Molecular mechanisms of myocardial remodeling: the role of aldosterone," *J. Mol. Cell. Cardiol.,* 34: 1577-1584 (2002). Accordingly, the compounds of the present invention as aldosterone synthase inhibitors, are also useful for treatment of a disorder or disease mediated by aldosterone synthase or responsive to inhibition of aldosterone synthase. In particular, the compounds of the present invention as aldosterone synthase inhibitors are useful for treatment of a disorder or disease characterized by abnormal aldosterone synthase activity. Preferably, the compounds of the present invention are also useful for treatment of a disorder or disease selected from hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, inflammation, increased formation of collagen, fibrosis such as cardiac or myocardiac fibrosis and remodeling following hypertension and endothelial dysfunction.

Furthermore, the compounds of the present invention are useful as CYP11B1 (11-β-hydroxylase) inhibitors. CYP11B1 catalyzes the last steps of cortisol synthesis. Cortisol is the main glucocorticoid in human. It regulates energy mobilization and thus the stress response. In addition, it is involved in the immune response of the human body. Abnormally increased cortisol level is the cause of a variety of diseases including Cushing's syndrome. Accordingly, the compounds of the present invention as CYP11B1 inhibitors are also useful for the treatment of a disorder or a disease or a condition characterized by abnormal activity or abnormal level of CYP11B1. The compounds of the present invention can be used for the treatment of a disorder, a disease or a condition such as Cushing's syndrome, excessive CYP11B1 level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke and the cortisol-induced mineralocorticoid excess, etc.

Accordingly, in one aspect, the present invention provides the use of a compound of formula (Ia):

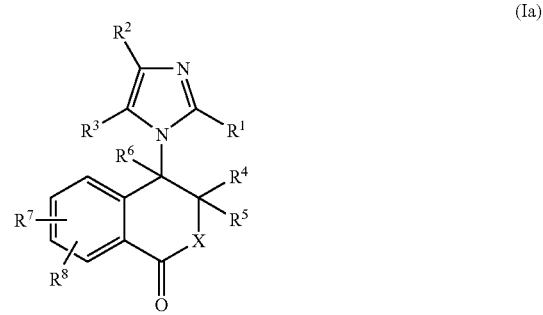

(Ia)

wherein

X is oxygen or N—$R^9$;

$R^1$ is hydrogen, halogen, thiol, ($C_3$-$C_7$) cycloalkyl, aryl, heteroaryl, ($C_1$-$C_7$) alkyl-O—C(O)—, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_3$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^2$ is hydrogen, halogen, ($C_3$-$C_7$) cycloalkyl, aryl, heteroaryl, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_3$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^3$ is hydrogen, halogen, cyano, cycloalkyl, ($C_1$-$C_7$) alkenyl, ($C_1$-$C_7$) alkynyl, ($C_1$-$C_7$) alkyl-$SO_2$—, ($C_1$-$C_7$) alkoxy$SO_2$—, sulfonamido, aryl, heteroaryl, H($R^{18}$ON=)C—, $R^{10}$O($CH_2$)$_n$—, $R^{12}R^{11}$($R^{13}$O)C—, $R^{14}$O—(O)C—, $R^{15}$—C(O)—, or $R^{10}$—N($R^{18}$)—C(O)—; or $R^3$ is ($C_1$-$C_7$) alkyl, 3-10 membered heteroaryl, or 3-10 membered heterocyclyl that is optionally substituted by one to four substituents selected from halogen, hydroxy, amino, mono-($C_1$-$C_7$) alkylamino, di-($C_1$-$C_7$) alkylamino; or $R^2$ and $R^3$ taken together with the carbon atoms to which they are attached optionally form a 5-9 membered ring;

$R^4$ and $R^5$ are independently hydrogen, aryl, ($C_1$-$C_7$) alkenyl, ($C_1$-$C_7$) alkynyl, or ($C_1$-$C_7$) alkyl, wherein said aryl or alkyl is optionally substituted by one to four substituents selected from hydroxy, ($C_1$-$C_7$) alkyl, halogen, ($C_1$-$C_7$) alkoxy, nitro, cyano, carboxy, thiol, ($C_3$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl; or $R^4$ and $R^5$, or $R^3$ and $R^4$ taken together with the carbon atom to which they are attached to optionally form a 4-9 membered ring;

$R^6$ is hydrogen, aryl, heteroaryl, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_1$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^7$ and $R^8$ are independently ($C_1$-$C_7$) alkyl or ($C_3$-$C_7$) cycloalkyl, each of which are optionally substituted by one to four substituents selected from hydroxy, ($C_1$-$C_7$) alkyl, halogen, ($C_1$-$C_7$) alkoxy, nitro, cyano, carboxy, thiol, ($C_3$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl; or $R^7$ and $R^8$ are independently hydrogen, halogen, cyano, nitro, mono-($C_1$-$C_7$) alkylamino, di-($C_1$-$C_7$) alkylamino, ($C_1$-$C_7$) alkoxy, ($C_1$-$C_7$) haloalkoxy, aryl, heteroaryl, $R^{16}$—O—, $R^{16}$—S—$R^{17}$—C(O)—, or $R^{17}$—$SO_2$—;

n is 1, 2, 3, or 4;

$R^9$, $R^{10}$, $R^{11}$, $R^{12}$ and $R^{13}$ are independently hydrogen, ($C_3$-$C_7$) cycloalkyl, aryl, aralkyl, heteroaryl, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_1$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^{14}$ is hydrogen, ($C_3$-$C_7$) cycloalkyl, aryl, heteroaryl, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_1$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^{15}$ is hydrogen, ($C_1$-$C_7$) alkyl, amino, mono-($C_1$-$C_7$) alkylamino, di-($C_1$-$C_7$) alkylamino, arylamino, diarylamino, aryl-mono-($C_1$-$C_7$) alkylamino, 4-10 membered heterocyclyl;

$R^{16}$ is hydrogen, ($C_1$-$C_7$) alkyl, aryl, or ($C_1$-$C_4$) haloalkyl, $R^{17}$ is amino, hydroxy, mono-($C_1$-$C_7$) alkylamino, di-($C_1$-$C_7$) alkylamino, 4-10 membered heterocyclyl, or ($C_1$-$C_7$) alkoxy; and $R^{18}$ is hydrogen or ($C_1$-$C_7$) alkyl, or $R^{10}$ and $R^{18}$ taken together with the carbon or hetero atom to which they are attached to optionally form a 4-9 membered ring; or pharmaceutically acceptable salts thereof; or an optical isomer thereof; or a mixture of optical isomers.

In another aspect, the present invention provides the use of a compound of formula (Ia):

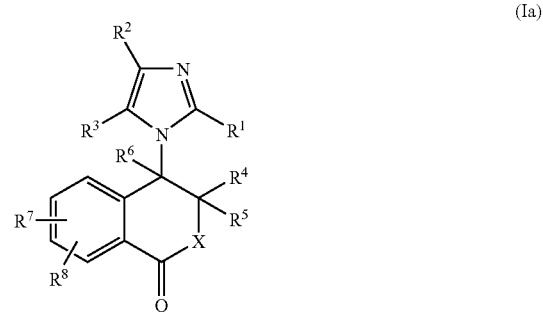

(Ia)

Wherein:

X is oxygen or N—$R^9$;

$R^1$ is hydrogen, halogen, thiol, ($C_3$-$C_7$) cycloalkyl, aryl, heteroaryl, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_3$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^2$ is hydrogen, halogen, ($C_3$-$C_7$) cycloalkyl, aryl, heteroaryl, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, (C3-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^3$ is hydrogen, halogen, cyano, ($C_1$-$C_7$) alkenyl, ($C_1$-$C_7$) alkynyl, ($C_1$-$C_7$) alkyl-$SO_2$—, ($C_1$-$C_7$) alkoxy$SO_2$—, sulfonamido, aryl, heteroaryl, H($R^{10}$ON=)C—, $R^{10}$O($CH_2$)$_n$—, $R^{12}R^{11}$($R^{13}$O)C—, $R^{14}$O—(O)C—, or $R^{15}$—C(O)—; or $R^3$ is ($C_1$-$C_7$) alkyl that is optionally substituted by one to four substituents selected from halogen, mono-($C_1$-$C_7$) alkylamino, di-($C_1$-$C_7$) alkylamino; or $R^2$ and $R^3$ taken together with the carbon atoms to which they are attached optionally form a 5-9 membered ring;

$R^4$ and $R^5$ are independently hydrogen, ($C_1$-$C_7$) alkenyl, ($C_1$-$C_7$) alkynyl, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_3$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl; or $R^4$ and $R^5$ taken together with the carbon atom to which they are attached to optionally form a 4-9 membered ring;

$R^6$ is hydrogen, aryl, heteroaryl, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_1$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^7$ and $R^8$ are independently ($C_1$-$C_7$) alkyl or ($C_3$-$C_7$) cycloalkyl, each of which are optionally substituted by one to four substituents selected from hydroxy, ($C_1$-$C_7$) alkyl, halogen, ($C_1$-$C_7$) alkoxy, nitro, cyano, carboxy, thiol, ($C_3$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl; or $R^7$ and $R^8$ are independently hydrogen, halogen, cyano, nitro, mono-($C_1$-$C_7$) alkylamino, di-($C_1$-$C_7$) alkylamino, ($C_1$-$C_7$) alkoxy, ($C_1$-$C_7$) haloalkoxy, aryl, heteroaryl, $R^{16}$—O—, $R^{16}$—S—, $R^{17}$—C(O)—, or $R^{17}$—$SO_2$—;

n is 1, 2, 3, or 4;

$R^9$, $R^{10}$; $R^{11}$, $R^{12}$ and $R^{13}$ are independently hydrogen, ($C_3$-$C_7$) cycloalkyl, aryl, heteroaryl, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_1$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^{14}$ is hydrogen, ($C_1$-$C_7$) alkyl, ($C_3$-$C_7$) cycloalkyl, aryl, heteroaryl, or ($C_1$-$C_7$) alkyl that is optionally substituted by one to four substituents selected from hydroxy, ($C_1$-$C_7$) alkyl, halogen, ($C_1$-$C_7$) alkoxy, nitro, cyano, carboxy, thiol, ($C_1$-$C_7$) cycloalkyl, ($C_1$-$C_7$) alkenyl, ($C_1$-$C_7$) alkynyl, amino, mono-($C_1$-$C_7$) alkylamino, di-($C_1$-$C_7$) alkylamino, aryl, heteroaryl, ($C_1$-$C_7$) alkyl-C(O)—O—, ($C_1$-$C_7$) alkyl-C(O)—, ($C_1$-$C_7$) alkyl-O—C(O)—, acylamino, guanidino, or heterocyclyl;

$R^{15}$ is hydrogen, ($C_1$-$C_7$) alkyl, amino, mono-($C_1$-$C_7$) alkylamino, di-($C_1$-$C_7$) alkylamino, arylamino, diarylamino, aryl-mono-($C_1$-$C_7$) alkylamino;

$R^{16}$ is hydrogen, ($C_1$-$C_7$) alkyl, aryl, or ($C_1$-$C_4$) haloalkyl, and $R^{17}$ is amino, hydroxy, mono-($C_1$-$C_7$) alkylamino, di-($C_1$-$C_7$) alkylamino, or ($C_1$-$C_7$) alkoxy; or pharmaceutically acceptable salts thereof; or an optical isomer thereof; or a mixture of optical isomers.

Preferably, the present invention provides the use of a compound of formula (Ia), wherein X is oxygen or N—$R^9$;

$R^1$ is hydrogen, halogen, thiol, ($C_3$-$C_7$) cycloalkyl, ($C_6$-$C_{10}$) aryl, (5-10)-membered heteroaryl, or ($C_1$-$C_4$) alkyl that is optionally substituted by one to four substituents selected from hydroxy, ($C_1$-$C_4$) alkyl, halogen, ($C_1$-$C_4$) alkoxy, amino, mono-($C_1$-$C_4$) alkylamino, or di-($C_1$-$C_4$) alkylamino;

$R^2$ is hydrogen, halogen, ($C_3$-$C_7$) cycloalkyl, ($C_6$-$C_{10}$) aryl, (5-10)-membered heteroaryl, or ($C_1$-$C_4$) alkyl that is optionally substituted by one to four substituents selected from hydroxy, ($C_1$-$C_4$) alkyl, halogen, ($C_1$-$C_4$) alkoxy, amino, mono-($C_1$-$C_4$) alkylamino, or di-($C_1$-$C_4$) alkylamino;

$R^3$ is hydrogen, halogen, cyano, ($C_6$-$C_{10}$) aryl, (5-10)-membered heteroaryl, $R^{10}$O($CH_2$)$_n$—, $R^{12}R^{11}(R^{13}O)C$—, $R^{14}O$—(O)C—, $R^{15}$—C(O)—, or ($C_1$-$C_4$) alkyl that is optionally substituted by one to four substituents selected from halogen, mono-($C_1$-$C_4$) alkylamino, di-($C_1$-$C_4$) alkylamino; or $R^2$ and $R^3$ taken together with the carbon atoms to which they are attached optionally form a 5-9 membered ring;

$R^4$ and $R^5$ are independently hydrogen, or ($C_1$-$C_4$) alkyl that is optionally substituted by one to four substituents selected from hydroxy, ($C_1$-$C_4$) alkyl, halogen, ($C_1$-$C_4$) alkoxy, amino, mono-($C_1$-$C_4$) alkylamino, or di-($C_1$-$C_4$) alkylamino; or $R^4$ and $R^5$ taken together with the carbon atom to which they are attached to optionally form a 4-9 membered ring;

$R^6$ is hydrogen, aryl or ($C_1$-$C_4$) alkyl that is optionally substituted by one to four substituents selected from hydroxy, ($C_1$-$C_4$) alkyl, halogen, ($C_1$-$C_4$) alkoxy, amino, mono-($C_1$-$C_4$) alkylamino, or di-($C_1$-$C_4$) alkylamino;

$R^7$ and $R^8$ are independently hydrogen, halogen, cyano, nitro, $R^{16}$—O—, $R^{16}$—S—, $R^{17}$—C(O)—, or $R^{17}$—$SO_2$—, ($C_1$-$C_4$) alkyl or ($C_3$-$C_7$) cycloalkyl, each of which are optionally substituted by one to four substituents selected from hydroxy, halogen, nitro, cyano, carboxy, thiol, ($C_3$-$C_7$) cycloalkyl, amino, mono-($C_1$-$C_4$) alkylamino, di-($C_1$-$C_4$) alkylamino;

n is 1, 2, 3, or 4;

$R^9$, $R^{10}$, $R^{11}$, $R^{12}$ and $R^{13}$ are independently hydrogen, ($C_3$-$C_7$) cycloalkyl, ($C_6$-$C_{10}$) aryl, (5-10)-membered heteroaryl, or ($C_1$-$C_4$) alkyl that is optionally substituted by one to four substituents selected from hydroxy, halogen, ($C_1$-$C_4$) alkoxy, ($C_3$-$C_7$) cycloalkyl, amino, mono-($C_1$-$C_4$) alkylamino, di-($C_1$-$C_4$) alkylamino, ($C_6$-$C_{10}$) aryl, (5-10)-membered heteroaryl;

$R^{14}$ is ($C_1$-$C_7$) alkyl, ($C_3$-$C_7$) cycloalkyl, ($C_6$-$C_{10}$) aryl, (5-10)-membered heteroaryl, or ($C_1$-$C_4$) alkyl that is optionally substituted by one to four substituents selected from hydroxy, halogen, ($C_1$-$C_4$) alkoxy, amino, mono-($C_1$-$C_4$) alkylamino, di-($C_1$-$C_4$) alkylamino, ($C_6$-$C_{10}$) aryl, (5-10)-membered heteroaryl;

$R^{15}$ is hydrogen, ($C_1$-$C_4$) alkyl, amino, mono-($C_1$-$C_4$) alkylamino, di-($C_1$-$C_4$) alkylamino, arylamino, diarylamino, aryl-mono-($C_1$-$C_4$) alkylamino;

$R^{16}$ is hydrogen, ($C_1$-$C_4$) alkyl, aryl, or ($C_1$-$C_4$) haloalkyl, and $R^{17}$ is amino, hydroxy, mono-($C_1$-$C_4$) alkylamino, di-($C_1$-$C_4$) alkylamino, or ($C_1$-$C_4$) alkoxy; or pharmaceutically acceptable salts thereof; or an optical isomer thereof; or a mixture of optical isomers.

Preferably, the present invention provides the use of a compound of formula (Ia), wherein X is N—$R^9$ or oxygen;

$R^1$ is hydrogen;

$R^2$ is hydrogen;

$R^3$ is cyano, $R^{10}$—N($R^{18}$)—C(O)—, $R^{12}R^{11}(R^{13}O)C$, $R^{14}O$—(O)C—, or $R^{15}$—C(O)—; or $R^4$ and $R^5$ are independently ($C_1$-$C_4$) alkyl; or $R^4$ and $R^5$ taken together with the carbon atom to which they are attached to optionally form a 3-9 membered ring;

$R^6$ is hydrogen;

$R^7$ is hydrogen;

$R^8$ is hydrogen, cyano, or halogen;

$R^9$ is hydrogen, benzyl, or $C_1$-$C_4$ alkyl;

$R^{10}$ is $C_1$-$C_4$ alkyl, phenyl, or benzyl;

$R^{11}$ and $R^{12}$ are independently hydrogen;

$R^{13}$ is hydrogen or ($C_1$-$C_6$) alkyl;

$R^{14}$ is $C_1$-$C_6$ alkyl;

$R^{15}$ is ($C_1$-$C_6$) alkyl; or $R^{18}$ is hydrogen or $C_1$-$C_4$ alkyl, or pharmaceutically acceptable salts thereof; or an optical isomer thereof; or a mixture of optical isomers.

Preferably, the present invention provides the use of a compound of formula (Ia), wherein X is oxygen;

$R^1$ is hydrogen;

$R^2$ is hydrogen;

$R^3$ is $R^{12}R^{11}(R^{13}O)C-$, $R^{14}O-(O)C-$, or $R^{15}-C(O)-$; or $R^4$ and $R^5$ are independently $(C_1-C_4)$ alkyl; or $R^6$ is hydrogen;

$R^7$ is hydrogen;

$R^8$ is hydrogen, or halogen;

$R^{11}$ and $R^{12}$ are independently hydrogen;

$R^{13}$ is hydrogen or $(C_1-C_6)$ alkyl;

$R^{14}$ is $C_3-C_6$ alkyl;

$R^{15}$ is $(C_1-C_6)$ alkyl; or pharmaceutically acceptable salts thereof; or an optical isomer thereof; or a mixture of optical isomers.

Preferably, the present invention provides the use of a compound of formula (Ia), wherein X is N—$R^9$ or oxygen;

$R^1$ is hydrogen, halogen, thiol, or $(C_1-C_7)$ alkyl;

$R^2$ is hydrogen, halogen, or $(C_1-C_7)$ alkyl;

$R^3$ is hydrogen, halogen, cycloalkyl, $(C_1-C_7)$ alkenyl, heteroaryl, 4-10 membered heterocyclyl optionally substituted by one to four $(C_1-C_7)$ alkyl, wherein said heterocyclyl having at least 3 hetero atoms, $R^{10}$—$N(R^{18})$—$C(O)$—, $H(R^{18}ON=)C-$, $R^{10}O(CH_2)_n-$, or $R^{14}O-(O)C-$;

$R^3$ is $(C_2-C_7)$ alkyl substituted by hydroxy or $(C_1-C_7)$ alkoxy, or $(C_1-C_7)$ alkyl substituted by $(C_1-C_7)$ alkoxy which is further substituted by one to four hydroxy;

$R^3$ is $(C_1-C_7)$ alkyl that is optionally substituted by one to four substituents selected from halogen, amino, mono-$(C_1-C_7)$ alkylamino, and di-$(C_1-C_7)$ alkylamino; or $R^2$ and $R^3$ taken together with the carbon atoms to which they are attached optionally form a 5-9 membered ring;

$R^4$ and $R^5$ are independently hydrogen, aryl, or $(C_1-C_7)$ alkyl, wherein said aryl or alkyl is optionally substituted by one to four substituents selected from hydroxy, $(C_1-C_7)$ alkyl, halogen, $(C_1-C_7)$ alkoxy, nitro, cyano, carboxy, thiol, $(C_3-C_7)$ cycloalkyl, $(C_1-C_7)$ alkenyl, $(C_1-C_7)$ alkynyl, amino, mono-$(C_1-C_7)$ alkylamino, di-$(C_1-C_7)$ alkylamino, aryl, heteroaryl, $(C_1-C_7)$ alkyl-C(O)—O—, $(C_1-C_7)$ alkyl-C(O)—, $(C_1-C_7)$ alkyl-O—C(O)—, acylamino, guanidino, or heterocyclyl;

$R^4$ and $R^5$, or $R^3$ and $R^4$ taken together with the carbon atom to which they are attached to optionally form a 4-9 membered ring;

$R^6$ is hydrogen, aryl, heteroaryl, or $(C_1-C_7)$ alkyl that is optionally substituted by one to four substituents selected from hydroxy, $(C_1-C_7)$ alkyl, halogen, $(C_1-C_7)$ alkoxy, nitro, cyano, carboxy, thiol, $(C_1-C_7)$ cycloalkyl, $(C_1-C_7)$ alkenyl, $(C_1-C_7)$ alkynyl, amino, mono-$(C_1-C_7)$ alkylamino, di-$(C_1-C_7)$ alkylamino, aryl, heteroaryl, $(C_1-C_7)$ alkyl-C(O)—O—, $(C_1-C_7)$ alkyl-C(O)—, $(C_1-C_7)$ alkyl-O—C(O)—, acylamino, guanidino, or heterocyclyl;

$R^7$ and $R^8$ are independently $(C_1-C_7)$ alkyl or $(C_3-C_7)$ cycloalkyl, each of which are optionally substituted by one to four substituents selected from hydroxy, $(C_1-C_7)$ alkyl, halogen, $(C_1-C_7)$ alkoxy, nitro, cyano, carboxy, thiol, $(C_3-C_7)$ cycloalkyl, $(C_1-C_7)$ alkenyl, $(C_1-C_7)$ alkynyl, amino, mono-$(C_1-C_7)$ alkylamino, di-$(C_1-C_7)$ alkylamino, aryl, heteroaryl, $(C_1-C_7)$ alkyl-C(O)—O—, $(C_1-C_7)$ alkyl-C(O)—, $(C_1-C_7)$ alkyl-O—C(O)—, acylamino, guanidino, or heterocyclyl; or $R^7$ and $R^8$ are independently hydrogen, halogen, cyano, nitro, mono-$(C_1-C_7)$ alkylamino, di-$(C_1-C_7)$ alkylamino, aryl, heteroaryl, $R^{16}$—O—, $R^{16}$—S—, $R^{17}$—C(O)—, or $R^{17}$—$SO_2$—;

$R^9$ is hydrogen, $(C_3-C_7)$ cycloalkyl, cyano, aralkyl, or $(C_1-C_7)$ alkyl that is optionally substituted by one to four halogen;

$R^{10}$ is, aralkyl substituted by one to four substituents selected from hydroxy, $(C_1-C_7)$ alkyl, or halogen, heteroaryl optionally substituted by one to four substituents selected from hydroxy, $(C_1-C_7)$ alkyl, halogen, or $(C_1-C_7)$ alkyl substituted by one to four hydroxy;

$R^{14}$ is aryl optionally substituted by one to four substituents selected from hydroxy, $(C_1-C_7)$ alkyl, halogen, $(C_1-C_7)$ alkoxy, nitro, cyano, carboxy, thiol, $(C_1-C_7)$ cycloalkyl, $(C_1-C_7)$ alkenyl, $(C_1-C_7)$ alkynyl, amino, mono-$(C_1-C_7)$ alkylamino, di-$(C_1-C_7)$ alkylamino, aryl, heteroaryl, $(C_1-C_7)$ alkyl-C(O)—O—, $(C_1-C_7)$ alkyl-C(O)—, $(C_1-C_7)$ alkyl-O—C(O)—, acylamino, guanidino, or heterocyclyl;

$R^{16}$ is hydrogen, $(C_1-C_7)$ alkyl, aryl, or $(C_1-C_4)$ haloalkyl, $R^{17}$ is amino, hydroxy, mono-$(C_1-C_7)$ alkylamino, di-$(C_1-C_7)$ alkylamino, 4-10 membered heterocyclyl, or $(C_1-C_7)$ alkoxy;

$R^{18}$ is hydrogen or $(C_1-C_7)$ alkyl; or n is 2, 3, or 4;

pharmaceutically acceptable salts thereof; or an optical isomer thereof; or a mixture of optical isomers.

Preferably, the present invention provides the use of a compound of formula (Ia), wherein X is oxygen or N—$R^9$;

$R^1$ is hydrogen, or $(C_1-C_7)$ alkyl;

$R^2$ is hydrogen, or $(C_1-C_7)$ alkyl;

$R^3$ is hydrogen, halogen, cycloalkyl, or $(C_1-C_7)$ alkenyl;

$R^4$ and $R^5$ are independently hydrogen, aryl, or $(C_1-C_7)$ alkyl;

$R^6$ is hydrogen, aryl, heteroaryl, or $(C_1-C_7)$ alkyl;

$R^7$ and $R^8$ are independently hydrogen, halogen, cyano, or nitro;

$R^9$ is hydrogen, or $(C_1-C_7)$ alkyl; or pharmaceutically acceptable salts thereof; or an optical isomer thereof; or a mixture of optical isomers.

Preferably, the present invention provides the use of a compound of formula (Ia), wherein X is N—$R^9$;

$R^1$ is hydrogen, halogen, thiol, or $(C_1-C_7)$ alkyl;

$R^2$ is hydrogen, halogen, or $(C_1-C_7)$ alkyl;

$R^3$ is $(C_1-C_7)$alkyl-O—(O)C—;

$R^4$ and $R^5$ are independently hydrogen, aryl, or $(C_1-C_7)$ alkyl, wherein said aryl or alkyl is optionally substituted by one to four substituents selected from hydroxy, $(C_1-C_7)$ alkyl, halogen, $(C_1-C_7)$ alkoxy, nitro, cyano, carboxy, thiol, $(C_3-C_7)$ cycloalkyl, $(C_1-C_7)$ alkenyl, $(C_1-C_7)$ alkynyl, amino, mono-$(C_1-C_7)$ alkylamino, di-$(C_1-C_7)$ alkylamino, aryl, heteroaryl, $(C_1-C_7)$alkyl-C(O)—O—, $(C_1-C_7)$alkyl-C(O)—, $(C_1-C_7)$ alkyl-O—C(O)—, acylamino, guanidino, or heterocyclyl; or $R^4$ and $R^5$, or $R^3$ and $R^4$ taken together with the carbon atom to which they are attached to optionally form a 4-9 membered ring;

$R^6$ is hydrogen, aryl, heteroaryl, or $(C_1-C_7)$ alkyl that is optionally substituted by one to four substituents selected from hydroxy, $(C_1-C_7)$ alkyl, halogen, $(C_1-C_7)$ alkoxy, nitro, cyano, carboxy, thiol, $(C_1-C_7)$ cycloalkyl, $(C_1-C_7)$ alkenyl, $(C_1-C_7)$ alkynyl, amino, mono-$(C_1-C_7)$ alkylamino, di-$(C_1-C_7)$ alkylamino, aryl, heteroaryl, $(C_1-C_7)$ alkyl-C(O)—O—, $(C_1-C_7)$ alkyl-C(O)—, $(C_1-C_7)$ alkyl-O—C(O)—, acylamino, guanidino, or heterocyclyl;

$R^7$ and $R^8$ are independently hydrogen or $(C_1-C_7)$ alkyl;

$R^9$ is $(C_3-C_7)$ cycloalkyl;

pharmaceutically acceptable salts thereof; or an optical isomer thereof; or a mixture of optical isomers.

Additionally, the present invention provides:

a compound of the present invention as described herein above for use as a medicament;

the use of a compound of the present invention as described herein above for the preparation of a pharmaceutical composition for the delay of progression and/or treatment of a disorder or disease mediated by aldosterone synthase, or characterized by abnormal activity of aldosterone synthase, or by abnormal expression of aldosterone synthase.

the use of a compound of the present invention as described herein above for the preparation of a pharmaceutical composition for the delay of progression and/or treatment of a disorder or disease selected from hypokalemia, hypertension, congestive heart failure, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction.

Additionally, the present invention provides, a compound of the present invention for use as a medicament;

the use of a compound of the present invention for the preparation of a pharmaceutical composition for the delay of progression and/or treatment of a disorder or disease or condition mediated by CYP11B1, or characterized by abnormal activity of CYP11B1, or by abnormal expression/level of CYP11B1.

the use of a compound of the present invention for the preparation of a pharmaceutical composition for the delay of progression and/or treatment of a disorder or disease or condition selected from Cushing's syndrome, excessive CYP11B1 level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke and the cortisol-induced mineralocorticoid excess, etc.

The compounds of formula (I)-(Ia) can be prepared by the procedures described in the following sections.

Generally, the compounds of formula (I)-(Ia) can be prepared according to Scheme 1, which contains five steps.

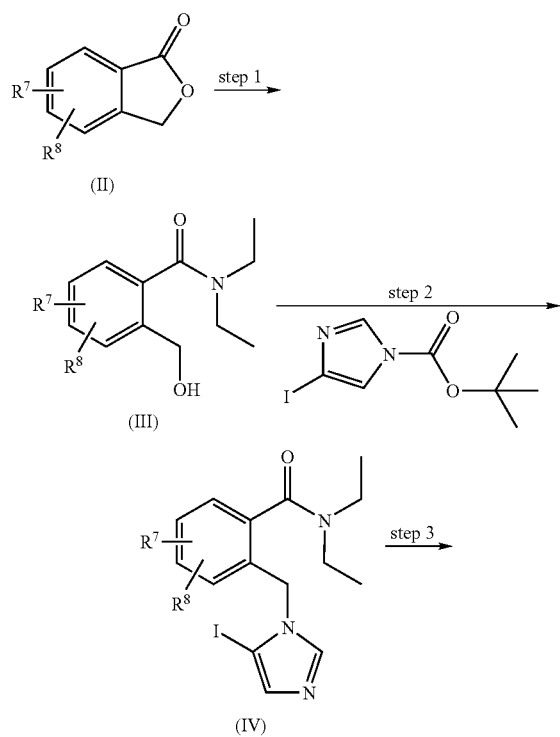

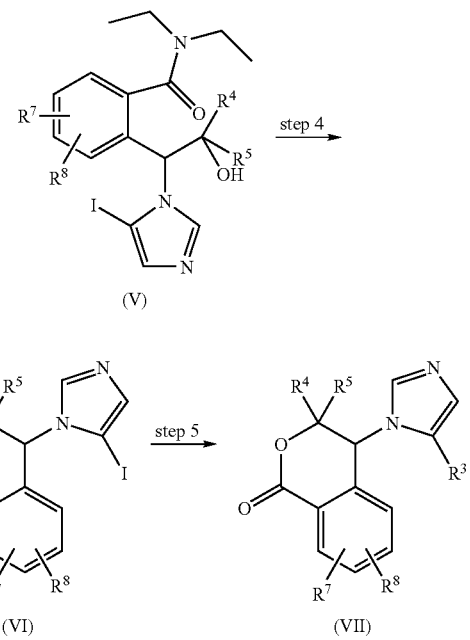

In step 1, aluminium(III) chloride promotes the reaction of a secondary amine, preferably diethylamine, with phthalide (II) to give alcohol (III). In step 2, the alcohol is activated, preferably by conversion to the triflate in DCM at −78° C., followed by reaction in the same flask with 1-Boc-4-iodoimidazole, followed by solvolysis of the Boc group, preferably with methanol, to give (IV). Compound (IV) can be alkylated in step 3 by deprotonation with a suitable base, preferably LDA, followed with trapping of the anion with the appropriate electrophilic reagent. Compound (V) is then converted in step 4 to lactone (VI) by basic hydrolysis of the amide, preferably with aqueous potassium hydroxide in dioxane, followed by acid-catalyzed ring-closure, in the same flask, preferably by acidifying the reaction mixture with concentrated HCl. Compound (VI) is then treated with the appropriate nucleophile, e.g. tributylvinyltin, in the presence of catalytic amounts of palladium salts, e.g. $Pd_2(dba)_3 \cdot CHCl_3$, and phosphine ligands, e.g. tri-(2)-furylphosphine, in polar aprotic solvent, e.g. NMP to give product (VII). Appropriate transformation of $R^3$ leads to further analogs. For example, if $R^3$ contains an alkene, the alkene can be converted to an alcohol by ozonolysis, followed by a reductive work-up, or the alkene can be converted to an alkyl by hydrogenation.

Alternatively, compounds of formula (I) and (Ia) can be prepared according to Scheme 2.

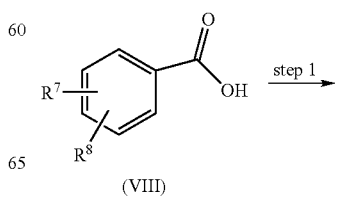

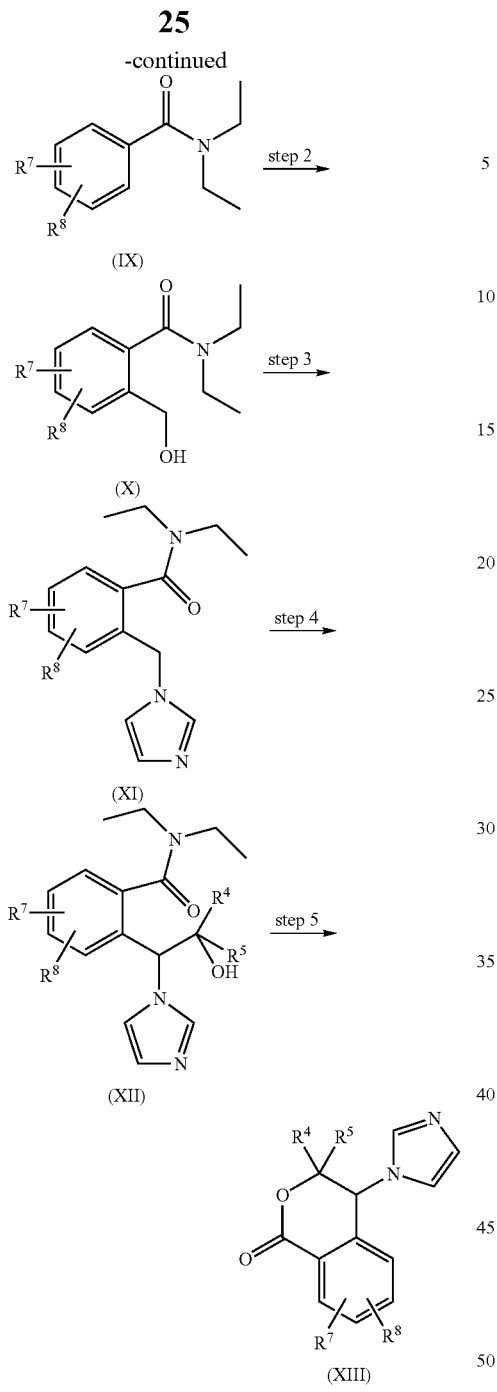

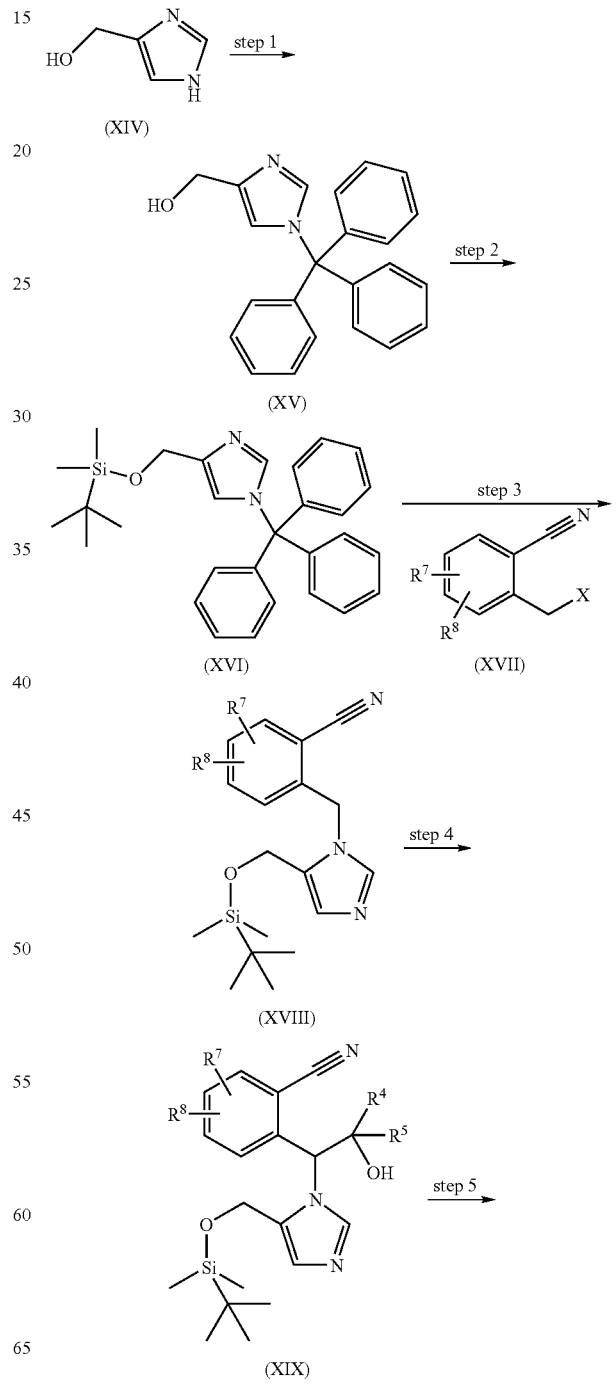

with a suitable base, preferably LDA, followed with trapping of the anion with the appropriate electrophilic reagent. Compound (XII) is then converted in step 5 to lactone (XIII) by basic hydrolysis of the amide, preferably with aqueous potassium hydroxide in dioxane, followed by acid-catalyzed ring-closure, in the same flask, preferably by acidifying the reaction mixture with concentrated HCl.

Alternatively, compounds of formula (I) and (Ia) can be prepared according to Scheme 3.

In step 1, a secondary amine, preferably diethylamine, is reacted with the acid chloride derived from benzoic acid derivative (VIII), to give amide (IX). In step 2, the amide is deprotonated in an ortho-directed metallation process, preferably using sec-BuLi and tetramethylethylenediamine, and the resulting anion is quenched with formaldehyde, to give alcohol (X). The alcohol is converted to the corresponding bromide, preferably using a reagent prepared from polymer-supported triphenylphosphine and bromine in dichloromethane. The intermediate bromide is reacted with imidazole, preferably in acetonitrile at 70° C., to give amide (XI). Compound (XI) can be alkylated in step 4 by deprotonation

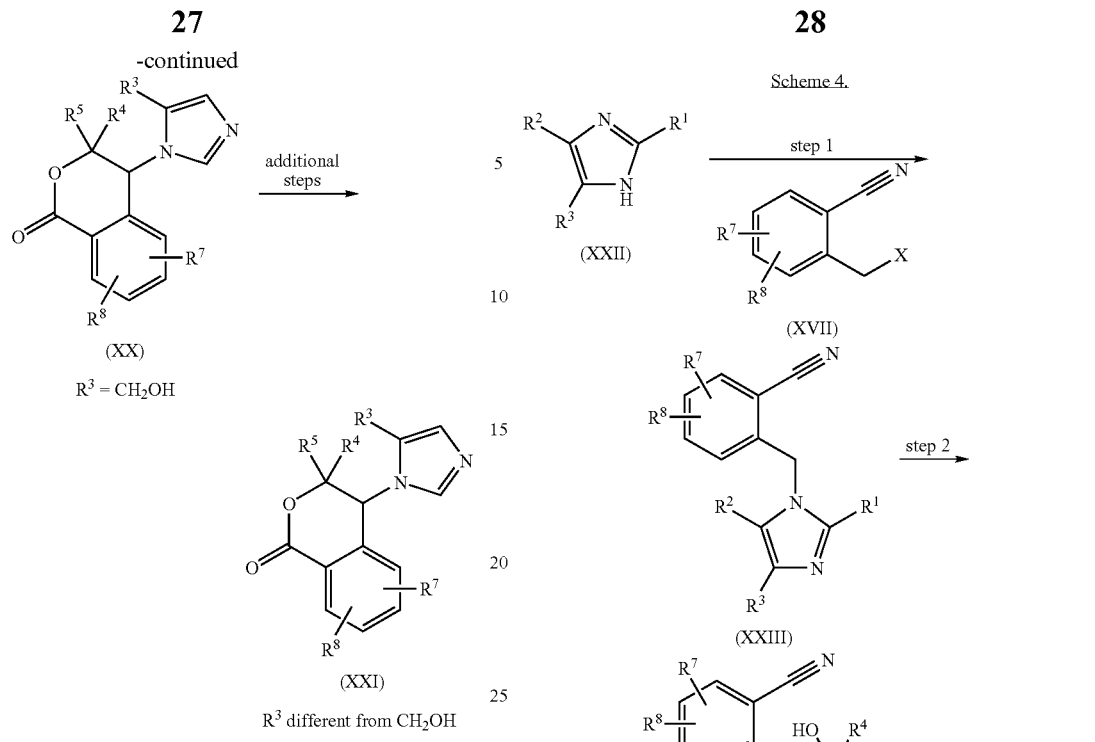

In step 1, a suitable protecting group, preferably triphenylmethyl, is introduced at the N-1 of (3H-imidazol-4-yl)-methanol (XIV), using a suitable reagent such as triphenylmethyl chloride, in the presence of triethylamine in DMF. Step 2 involves the protection of the alcohol resulting from step 1 as a silyl ether, preferably as t-butyldimethylsilyl ether, with a suitable reagent such as t-butyldimethylsilyl chloride in the presence of a suitable base, preferably imidazole, and an aprotic solvent, preferably DMF or $CH_2Cl_2$ to provide (XVI). Step 3 involves the reaction of a (XVI) with the appropriate alkylating reagent (XVII), such as X=Br, in an aprotic solvent, preferably $CH_3CN$ to provide (XVIII), after solvolysis, preferably using methanol. Alkylating agents (XVII) may be prepared by treatment of the corresponding 2-methylbenzonitrile derivative with a suitable brominating agent, e.g. NBS, in the presence of a suitable radical initiator, such as AIBN or benzoyl peroxide. Alternatively, alkylating agents (XVII) may be generated by conversion of a substituted benzyl alcohol to the corresponding halide by treatment with, for example, $CBr_4$ and $PPh_3$. Compound (XVIII) can be alkylated in step 4 by deprotonation with a suitable base, preferably LHMDS, followed with trapping of the anion with the appropriate electrophilic reagent. Compound (XIX) is then converted in step 5 to lactone (XX) using an acid, preferably sulfuric acid, in mixtures of water and an organic solvent, preferably THF or dioxane. Appropriate transformation of $R^3$ in (XX) leads to further analogs (XXI). For example the alcohol can be transformed to an ether by conversion to the chloride and nucleophilic substitution with the appropriate alcohol. In an other example, the alcohol can be oxidized to the aldehyde and the aldehyde be subjected to reductive amination conditions.

Also alternatively, the compounds of formula (I) and (Ia) can be prepared according to Scheme 4 in three steps.

Step 1 involves the reaction of a (XXII) with the appropriate alkylating reagent (XVII), such as X=Br, in the presence of a base, preferably sodium hydride. Alkylating agents (XVII) may be prepared by treatment of the corresponding 2-methylbenzonitrile derivative with a suitable brominating agent, e.g. NBS, in the presence of a suitable radical initiator, such as AIBN or benzoyl peroxide. Alternatively, alkylating agents (XVII) may be generated by conversion of a substituted benzyl alcohol to the corresponding halide by treatment with, for example, $CBr_4$ and $PPh_3$. Compound (XXIII) can be alkylated in step 2 by deprotonation with a suitable base, preferably LHMDS, followed with trapping of the anion with the appropriate electrophilic reagent. Compound (XXIV) is then converted in step 3 to lactone (XXV) using an acid, preferably sulfuric acid, in mixtures of water and an organic solvent, such as THF or dioxane.

Also alternatively, the compounds of formula (I) and (Ia) can be prepared according to Scheme 5 in four steps;

Scheme 5.

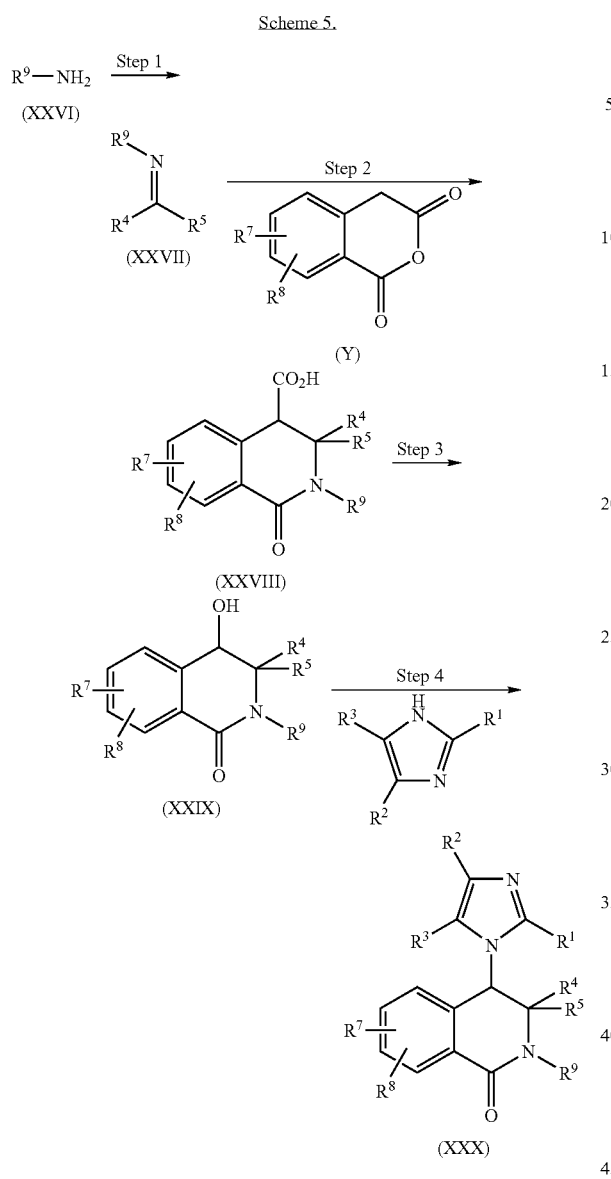

Scheme 6.

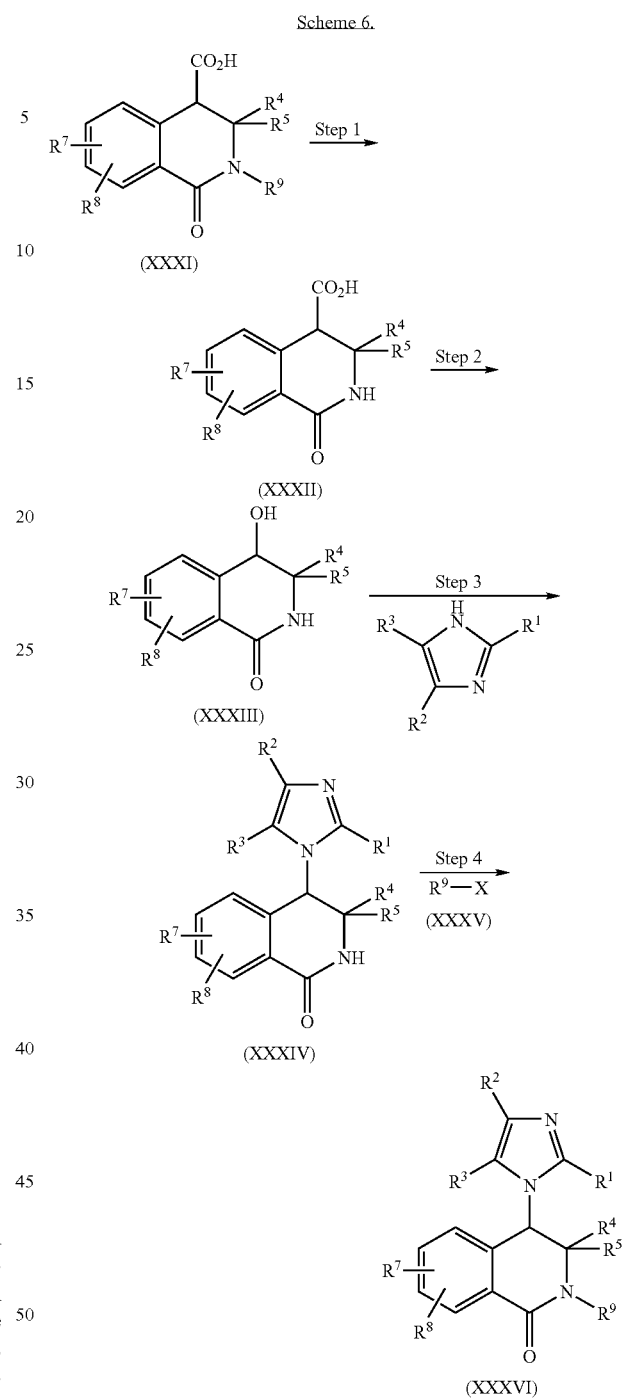

In step 1, the appropriate primary amine is condensed with acetone, preferably under the action of type-I neutral alumina. In step 2, the resulting imine (XVII) is condensed with homophthalic anhydride derivatives (Y) in the presence of the appropriate acid, preferably acetic acid, to afford lactams (XXVIII). Step 3 involves the oxidative cleavage of the carboxylic acid functional group, preferably by lead (IV) acetate employing a mixed solvent system preferably containing acetic acid and benzene. Saponification of the reaction mixture employing the appropriate base, preferably LiOH in mixtures of water and an organic solvent, preferably THF, then furnishes alcohol (XXIX). In step 4, the alcohol is substituted with imidazole derivatives, preferably using di-tert-butyl azodicarboxylate and triphenylphosphine in THF, to give (XXX).

Compounds (Y) can be prepared from 2-(hydroxymethyl) phenol derivatives (Podraza, K. F. *J. Heterocyclic Chem.* 1987, 24, 801).

Also alternatively, the compounds of formula (I) and (Ia) can be prepared according to Scheme 6 in four steps;

This method begins with compound (XXXI) (Scheme 5), where $R^9$ is preferably 3,4-dimethoxybenzyl. Treatment of (XXXI) with an acid, preferably trifluoroacetic acid, in the presence of a carbocation scavenger, preferably thioanisole, furnishes lactam XXXII (Step 1, Scheme 5). Step 2 involves the oxidative cleavage of the carboxylic acid functional group, preferably by lead (IV) acetate employing a mixed solvent system preferably containing acetic acid and benzene. Saponification of the reaction mixture employing the appropriate base, preferably LiOH in mixtures of water and an organic solvent, preferably THF, then furnishes alcohol (XXXIII). In step 3, the alcohol is substituted with imidazole derivatives, preferably using triphenylphosphine and di-tert-butyl azodicarboxylate in THF, to give (XXXIV). Deprotonation (Step 4) employing the appropriate base, preferably sodium hydride, and trapping of the anion with an appropriate alkylating agent, such as X=I or X=OTf permits access to lactams (XXXVI).

Also alternatively, the compounds of formula (I) and (Ia) can be prepared according to Scheme 7 in five steps;

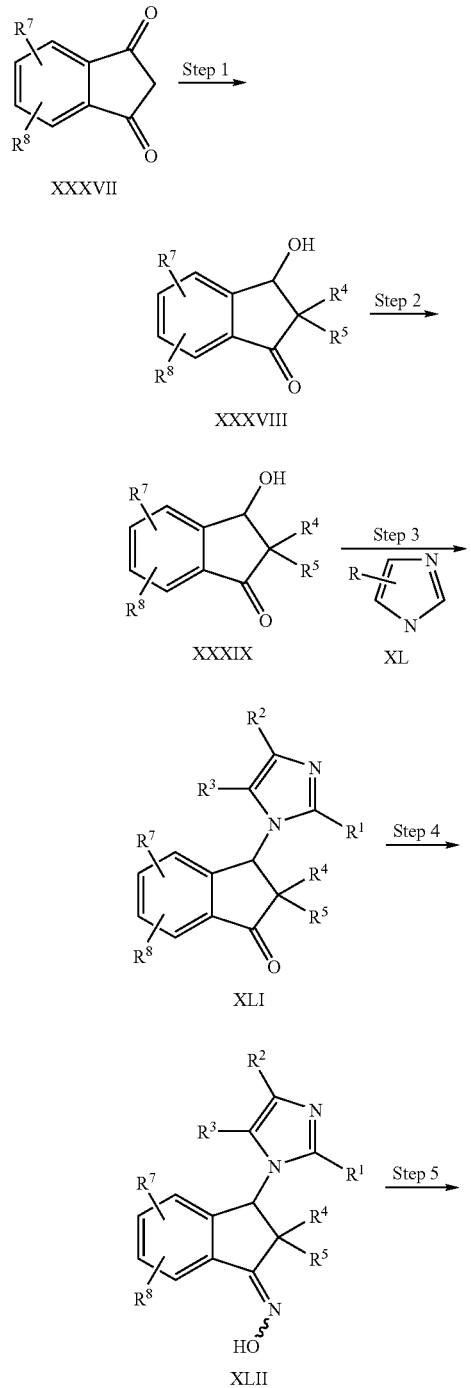

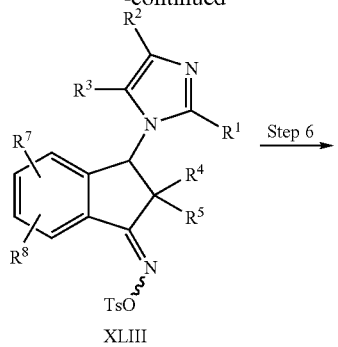

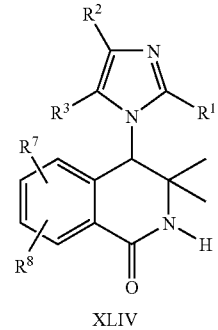

In Step 1, di-ketones of type XXXVII undergo alkylation upon action of a non-nucleophilic base, preferably potassium fluoride absorbed on Celite®, and an alkyl halide, preferably iodomethane to afford compounds of type XXXVIII. Step 2 involves mono-reduction employing the appropriate source and equivalents of hydride, preferably, 0.3 equivalents of sodium borohydride, to furnish alcohols of type XXXIX. Reaction of alcohols of type XXXIX with trifluoromethanesulfonic anhydride in the presence of a tertiary amine, preferably diisopropylethylamine, followed by treatment with imidazoles of type XL furnishes ketones of type XLI. Condensation (Step 4) of ketones of type XLI with hydroxylamine and sulfonylation of the resulting oxime (XLII) via employment of p-toluenesulfonyl chloride, in the presence of DMAP and pyridine provides compounds of type XLIII. Step 6 involves a thermally promoted Beckmann-type rearrangement, preferably accomplished via microwave irradiation at 190° C., to afford amides of type XLIV. The nitrogen atom of the resulting amide functionality can then be optionally manipulated, for example by alkylation via the employment of a strong base, preferably NaH, and an alkyl halide, for example iodomethane.

Generally, enantiomers of the compounds of the present invention can be prepared by methods known to those skilled in the art to resolve racemic mixtures, such as by formation and recrystallization of diastereomeric salts or by chiral chromotagraphy or HPLC separation utilizing chiral stationery phases.

In starting compounds and intermediates which are converted to the compounds of the invention in a manner described herein, functional groups present, such as amino, thiol, carboxyl and hydroxy groups, are optionally protected by conventional protecting groups that are common in preparative organic chemistry. Protected amino, thiol, carboxyl and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, room temperature or elevated temperatures, preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers etc.

Preferably, the pharmaceutical compositions are tablets and gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable compositions for transdermal application include an effective amount of a compound of the invention with carrier. Advantageous carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

The present invention further provides anhydrous pharmaceutical compositions and dosage forms comprising the compounds of the present invention as active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical compositions contain a therapeutically effective amount of a compound of the invention as defined above, either alone or in a combination with another therapeutic agent, e.g., each at an effective therapeutic dose as reported in the art. Such therapeutic agents include anti-obesity agents, such as orlistat, anti-hypertensive agents, inotropic agents and hypolipidemic agents, e.g., loop diuretics, such as ethacrynic acid, furosemide and torsemide; angiotensin converting enzyme (ACE) inhibitors, such as benazepril, captopril, enalapril, fosinopril, lisinopril, moexipril, perinodopril, quinapril, ramipril and trandolapril; inhibitors of the Na-K-ATPase membrane pump, such as digoxin; neutralendopeptidase (NEP) inhibitors; ACE/NEP inhibitors, such as omapatrilat, sampatrilat and fasidotril; angiotensin II antagonists, such as candesartan, eprosartan, irbesartan, losartan, telmisartan and valsartan, in particular, valsartan; β-adrenergic receptor blockers, such as acebutolol, atenolol, betaxolol, bisoprolol, metoprolol, nadolol, propranolol, sotalol and timolol; inotropic agents, such as digoxin, dobutamine and milrinone; calcium channel blockers, such as amlodipine, bepridil, diltiazem, felodipine, nicardipine, nimodipine, nifedipine, nisoldipine and verapamil; and 3-hydroxy-3-methyl-glutaryl coenzyme A reductase (HMG-CoA) inhibitors, such as lovastatin, pitavastatin, simvastatin, pravastatin, cerivastatin, mevastatin, velostatin, fluvastatin, dalvastatin, atorvastatin, rosuvastatin and rivastatin. A compound of the present invention may be administered either simultaneously, before or after the other active ingredient, either separately by the same or different route of administration or together in the same pharmaceutical formulation.

Furthermore, the combinations as described above can be administered to a subject via simultaneous, separate or sequential administration (use). Simultaneous administration (use) can take place in the form of one fixed combination with two or more active ingredients, or by simultaneously administering two or more compounds that are formulated independently. Sequential administration(use) preferably means administration of one (or more) compounds or active ingredients of a combination at one time point, other compounds or active ingredients at a different time point, that is, in a chronically staggered manner, preferably such that the combination shows more efficiency than the single compounds administered independently (especially showing synergism). Separate administration (use) preferably means administration of the compounds or active ingredients of the combination independently of each other at different time points, preferably meaning that two compounds are administered such that no overlap of measurable blood levels of both compounds are present in an overlapping manner (at the same time).

Also combinations of two or more of sequential, separate and simultaneous administrations are possible, preferably such that the combination compound-drugs show a joint therapeutic effect that exceeds the effect found when the combination compound-drugs are used independently at time intervals so large that no mutual effect on their therapeutic efficiency can be found, a synergistic effect being especially preferred.

Additionally, the present invention provides:
 a pharmaceutical composition or combination of the present invention for use as a medicament;
 the use of a pharmaceutical composition or combination of the present invention for the delay of progression and/or treatment of a disorder or disease mediated by aldosterone synthase, or characterized by abnormal activity of aldosterone synthase.
 the use of a pharmaceutical composition or combination of the present invention for the delay of progression and/or treatment of a disorder or disease mediated by or associated with CYP11B1, or responsive to inhibition of CYP11B1, or characterized by abnormal activity or expression of CYP11B1.
 the use of a pharmaceutical composition or combination of the present invention for the delay of progression and/or treatment of a disorder or disease selected from hypokalemia, hypertension, congestive heart failure, renal failure, in particular, chronic renal failure, restenosis, atherosclerosis, syndrome X, obesity, nephropathy, post-myocardial infarction, coronary heart diseases, increased formation of collagen, fibrosis and remodeling following hypertension and endothelial dysfunction.
 the use of a pharmaceutical composition or combination of the present invention for the preparation of a pharmaceutical composition for the delay of progression and/or treatment of a disorder or disease or condition selected from Cushing's syndrome, excessive CYP11B1 level, the ectopic ACTH syndrome, the change in adrenocortical mass, primary pigmented nodular adrenocortical disease (PPNAD) Carney complex (CNC), anorexia nervosa, chronic alcoholic poisoning, nicotine or cocaine withdrawal syndrome, the post-traumatic stress syndrome, the cognitive impairment after a stroke and the cortisol-induced mineralocorticoid excess, etc.

The pharmaceutical composition or combination of the present invention can be in unit dosage of about 1-1000 mg of active ingredients for a subject of about 50-70 kg, preferably about 5-500 mg of active ingredients. The therapeutically effective dosage of a compound, the pharmaceutical composition, or the combinations thereof is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, intraarterially, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, preferably between about 1-100 mg/kg.

The activities of a compound according to the present invention can be assessed by the following in vitro & in vivo methods well-described in the art. See Fieber, A et al. (2005), "Aldosterone Synthase Inhibitor Ameliorates Angiotensin II—Induced Organ Damage," *Circulation*, 111:3087-3094. The reference cited herein is incorporated by reference in its entirety.

In particular, the aldosterone synthase inhibitory activities in vitro can be determined by the following assay.

Human adrenocortical carcinoma NCI-H295R cell line is obtained from American Type Culture Collection (Manassas, Va.). Insulin/transferrin/selenium (ITS)-A supplement (100×), DMEM/F-12, antibiotic/antimycotic (100×), and fetal calf serum (FCS) are purchased from Gibco (Grand Island, N.Y.). Anti-mouse PVT scintillation proximity assay (SPA) beads and NBS 96-well plates are obtained from Amersham (Piscataway, N.J.) and Corning (Acton, Mass.), respectively. Solid black 96-well flat bottom plates are purchased from Costar (Corning, N.Y.). Aldosterone and angiotensin (Ang II) are purchased from Sigma (St. Louis, Mo.). D-[1,2,6,7-$^3$H(N)]aldosterone is acquired from PerkinElmer (Boston, Mass.). Nu-serum is a product of BD Biosciences (Franklin Lakes, N.J.).

For in vitro measurement of aldosterone activity, human adrenocortical carcinoma NCI-H295R cells are seeded in NBS 96-well plates at a density of 25,000 cells/well in 100 µl of a growth medium containing DMEM/F12 supplemented with 10% FCS, 2.5% Nu-serum, 1 µg ITS/ml, and 1× antibiotic/antimycotic. The medium is changed after culturing for 3 days at 37° C. under an atmosphere of 5% $CO_2$/95% air. On the following day, cells are rinsed with 100 µl of DMEM/F12 and incubated with 100 µl of treatment medium containing 1 µM Ang II and a compound at different concentrations in quadruplicate wells at 37° C. for 24 hr. At the end of incubation, 50 µl of medium is withdrawn from each well for measurement of aldosterone production by an RIA using mouse anti-aldosterone monoclonal antibodies.

Measurement of aldosterone activity can also be performed using a 96-well plate format. Each test sample is incubated with 0.02 µCi of D-[1,2,6,7-$^3$H(N)]aldosterone and 0.3 µg of anti-aldosterone antibody in phosphate-buffered saline (PBS) containing 0.1% Triton X-100, 0.1% bovine serum albumin, and 12% glycerol in a total volume of 200 µl at room temperature for 1 hr. Anti-mouse PVT SPA beads (50 µl) are then added to each well and incubated overnight at room temperature prior to counting in a Microbeta plate counter. The amount of aldosterone in each sample is calculated by comparing with a standard curve generated using known quantities of the hormone.

The in vivo inhibitory activities for aldosterone synthase can be determined by the following assay.

Test compounds (i.e., potential aldosterone synthase inhibitors) are profiled in vivo in a conscious rat model of acute secondary hyperaldosteronism. Wild-type rats are instrumented with chronically indwelling arterial and venous cannulas, which are exteriorized through a tether/swivel system. The ambulatory rats are housed in specialized cages to allow blood sampling and parenteral drug administration without disturbing the animals. Angiotensin II is continuously infused intravenously at a level sufficient to elevate plasma aldosterone concentration (PAC) by ~200-fold to 1-5 nM. This PAC increase is sustained at a stable level for at least 8-9 hours. Test compounds are administered p.o. (via oral gavage) or parenterally (via the arterial catheter) after one hour of angiotensin 11 infusion at a time when PAC has increased to a steady-state level. Arterial blood samples are collected before and at various times (up to 24 hours) after test agent administration for later determination of PAC and concentration of test agent. From these measurements, various parameters can be derived, e.g., 1) onset and duration of PAC reduction by the test agent, 2) pharmacokinetic parameters of the test agent such as half-life, clearance, volume of distribution, and oral bioavailability, 3) dose/PAC response, dose/test-agent concentration, and test-agent concentration/PAC response relationships, and 4) dose- and concentration-potencies and efficacy of the test agent. A successful test compound decreases PAC in a dose- and time-dependent fashion in the dose range of about 0.01 to about 10 mg/kg i.a. or p.o.

The in vitro inhibitory activities for CYP11B1 can be determined by the following assay.

The cell line NCI-H295R was originally isolated from an adrenocortical carcinoma and has been characterized in the literature through the stimulable secretion of steroid hormones and the presence of the enzymes essential for steroidogenesis. Thus, the NCI-H295R cells have Cyp11 B1 (steroid 11 p-hydroxylase). The cells show the physiological property of zonally undifferentiated human foetal adrenocortical cells which, however, have the capacity to produce the steroid hormones which are formed in the three, phenotypically distinguishable zones in the adult adrenal cortex. The NCI-H295R cells (American Type Culture Collection, ATCC, Rockville, Md., USA) are grown in Dulbeoco's Modified Eagle'Ham F-12 Medium (DME/F12), which has been I supplemented with Ulroser SF Serum(Soprachem, Cergy-Saint-Christophe, France), insulin, transferrin, selenite (1-T-S, Becton Dickinson Biosiences, Franklin lakes, NJ, USA) and antibiotics in 75 cm$^2$ cell culture vessels at 37° C. and in a 95% air-5% carbon dioxide atmosphere. The cells are subsequently transferred for colony formation into a 24-well incubation vessel. They are cultivated there in DME/F12 medium, which is now supplemented with 0.1% bovine serum instead of Ultroser SF for 24 hours. The experiment is initiated by cultivating the cells in DME/F12 medium which is supplemented with 0.1% bovine serum albumin and test compound, in the presence or absence of cell stimulants, for 72 hours. The test substance is added in a concentration range from 0.2 nanomolar to 20 millimolar. Cell stimulants which can be used are angiotensin 11 (1D or 100 nanomolar), potassium ions (16 millimolar), forskolin (10 micromolar) or a combination of two stimulants.

The excretion of aldosterone, cortisol, corticosterone and estradiol/estrone into the culture medium can be detected and quantified by commercially available, specific monoclonal antibodies in radioimmunoassays in accordance with the manufacturers instructions.

Inhibition of the release of certain steroids can be used as a measure of the respective enzyme inhibition by the added test compounds. The dose-dependent inhibition of enzymic activity by a compound is calculated by means of an inhibition plot which is characterized by an IC50.

The IC50 values for active test compounds are ascertained by a simple linear regression analysis in order to construct inhibition plots without data weighting. The inhibition plot is calculated by fitting a 4-parameter logistic function to the raw data points using the least squares method. The equation of the 4-parameter logistic function is calculated as follows: Y=(d−a)/((1+(x/c)b))+a I where: a=minimum data level b=gradient I c=ICED, d=maximum data level x=inhibitor concentration.

TABLE

Inhibitory Activity of Compounds

| Entry | Stereo-chemical state | Compound | Aldosterone cellular $IC_{50}$ (nM) | CYP11B1 % I (100 nM) |
|---|---|---|---|---|
| 1 | Ent-2 | 3-(3,3-dimethyl-1-oxo-isochroman-4-yl)-3H-imidazole-4-carboxylic acid methyl ester | 24 | 100 |
| 2 | Ent-2 | 3-(3,3-dimethyl-1-oxo-isochroman-4-yl)-3H-imidazole-4-carboxylic acid ethyl ester | 3 | 94 |
| 3 | Ent-1 | 3-(3,3-dimethyl-1-oxo-isochroman-4-yl)-3H-imidazole-4-carboxylic acid phenyl ester | 3 | 97 |
| 4 | Racemic | 3,3-dimethyl-4-[5-(3-methyl-[1,2,4]oxadiazol-5-yl)imidazol-1-yl]-isochroman-1-one | 187 | 100 |
| 5 | Racemic | 3-(3,3-dimethyl-1-oxo-isochroman-4-yl)-3H-imidazole-4-carbaldehyde oxime (trans) | 47 | 97 |
| 6 | Racemic | 4-(5-butyl-imidazol-1-yl)-3,3-dimethyl-isochroman-1-one | 6 | 100 |
| 7 | Ent-1 | 4-(5-vinyl-imidazol-1-yl)-3,3-dimethyl-isochroman-1-one | 22 | 100 |
| 8 | Ent-1 | 4-(5-ethoxymethyl-imidazol-1-yl)-3,3-dimethyl-isochroman-1-one | 17 | 100 |
| 9 | Ent-2 | [4-(5-ethyl-imidazol-1-yl)-isochroman-1-one]-3-spirocyclobutane | 7 | 100 |
| 10 | Racemic | [4-(5-ethyl-imidazol-1-yl)-isochroman-1-one]-3-spiro(4-tetrahydropyran) | 314 | 90 |
| 11 | Racemic | 3-(2,3,3-trimethyl-1-oxo-1,2,3,4-tetrahydro-isoquinolin-4-yl)-3H-imidazole-4-carboxylic acid methyl ester | 73 | 95 |
| 12 | Racemic | 3-(2-cyclopropyl-3,3-dimethyl-1-oxo-1,2,3,4-tetrahydro-isoquinolin-4-yl)-3H-imidazole-4-carboxylic acid methyl ester | 530 | 77 |

Ent-1: the first eluting enantiomer; Ent-2: the second eluting enantiomer;
I %: percentage of inhibition.

Abbreviations
DAST: (diethylamino)sulfur trifluoride
DMAP: 4-dimethylaminopyridine
DMF: N,N-dimethylformamide
ESI: electrospray ionization
h: hours
HPLC: high pressure liquid chromatography
HRMS: high resolution mass spectrometry
LC-MS: liquid chromatography/mass spectrometry
LDA: lithium diisopropylamide
LHMDS: lithium hexamethyldisilazide
min: minutes
MS: mass spectrometry
NBS: N-bromosuccinimide
NMR: nuclear magnetic resonance
TBSCl: tert-butyldimethylsilyl chloride
TFA: trifluoroacetic acid
THF: tetrahydrofuran
$t_r$: retention time
Tr: trityl

EXAMPLES

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. The compounds in the following examples have been found to have $IC_{50}$ values in the range of about 1 nM to about 1000 nM for inhibition of cellular aldosterone secretion, and have percent inhibitions values in the range of about 50% to 100% for CYP11B1 at 100 nM concentrations.

Example 1

(a) N,N-Diethyl-2-hydroxymethyl-benzamide (CAS# 103258-38-4)

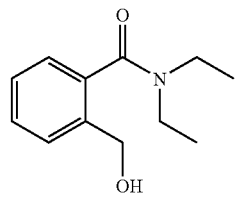

To a suspension of aluminium trichloride (12.67 g, 94.98 mmol) in dichloroethane (40 mL) is added diethylamine (13.5 g, 182.7 mmol) in dichloroethane (20 mL) while the temperature is maintained below 25° C. with an ice-bath. After another 25 min at r.t., phthalide (10.00 g, 74.5 mmol) is added in three portions and formation of a precipitate is observed. After 45 min, water and ice are added and the mixture is stirred for 30 min and filtered through celite. The aqueous phase is extracted with dichloromethane. After drying the combined organic phase over $MgSO_4$ and filtering through a cotton plug, the volatiles are removed in vacuo to give an orange residue, which is purified by silica gel flash chromatography (dichloromethane-methanol, 49:1 to 97:3 to 19:1) to give N,N-diethyl-2-hydroxymethyl-benzamide as an orange oil; $^1$H NMR (400 MHz) δ 1.09 (3 H, t, J=7.0 Hz), 1.28 (3 H, t, J=7.0 Hz), 3.24 (2 H, q, J=7.0 Hz), 3.55 (1 H, t, J=6.8 Hz), 3.58 (2 H, q, J=7.0 Hz), 4.52 (2 H, d, J=6.8 Hz), 7.24 (1 H, dd, J=7.4, 1.5 Hz), 7.32 (1 H, td, J=7.4, 1.5 Hz), 7.39 (1 H, td, J=7.4, 1.5 Hz), 7.44 (1 H, td, J=7.4, 1.5 Hz).

(b) N,N-Diethyl-2-(5-iodo-imidazol-1-ylmethyl)-benzamide

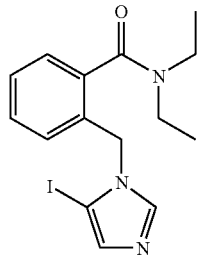

A flask is charged with dichloromethane (200 mL) and trifluoromethanesulfonic anhydride (19.34 g, 67.20 mmol) and cooled to −78° C. A solution of diisopropylethylamine (9.57 g, 73.30 mmol) and N,N-diethyl-2-hydroxymethyl-benzamide (12.92 g, 61.09 mmol) in dichloromethane (40 mL) is added over 10 min. After 30 min, a solution of 4-iodo-imidazole-1-carboxylic acid tert-butyl ester (12.83 g, 42.76 mmol) in dichloromethane (40 mL) is added. The mixture is allowed to gradually warm overnight and after 18 h, saturated aqueous sodium bicarbonate (100 mL) is added and the mixture is stirred vigorously for 30 min. The aqueous layer is extracted with dichloromethane. The combined organic phase is dried over MgSO$_4$, filtered through a cotton plug and concentrated in vacuo. The residue is purified by silica gel flash chromatography (dichloromethane-methanol, 49:1) to afford N,N-diethyl-2-(5-iodo-imidazol-1-ylmethyl)-benzamide; MS (ESI) m/z 384.1 (M+H).

(c) N,N-Diethyl-2-[(1-hydroxy-cyclobutyl)-(5-iodo-imidazol-1-yl)-methyl]-benzamide

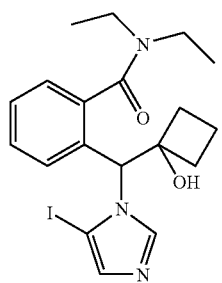

To a solution of diisopropylamine (0.38 g, 3.76 mmol) in THF (25 mL) at −78° C. under nitrogen is added n-BuLi (2.5M in hexanes, 1.50 mL, 3.75 mmol) and the mixture is warmed to 0° C. After 15 min, the LDA solution is cooled to −78° C. and a solution of N,N-diethyl-2-(5-iodo-imidazol-1-ylmethyl)-benzamide (1.00 g, 2.51 mmol) in THF (5 mL) is added over 10 min. Fifteen min after the end of addition, cyclobutanone (0.90 g, 12.53 mmol) in THF (2 mL) is added to the brown solution. After 1.5 h, 10% acetic acid in water is added. The organic phase is washed with saturated aqueous sodium bicarbonate and the combined organic phase is dried over MgSO$_4$, filtered through a cotton plug and concentrated in vacuo. The residue is purified by silica gel flash chromatography (elution with dichloromethane-methanol, 49:1 to 97:3) to N,N-diethyl-2-[(1-hydroxy-cyclobutyl)-(5-iodo-imidazol-1-yl)-methyl]-benzamide; MS (ESI) m/z 454.2 (M+H).

(d) [4-(5-Iodo-imidazol-1-yl)-isochroman-1-one]-3-spirocyclobutane

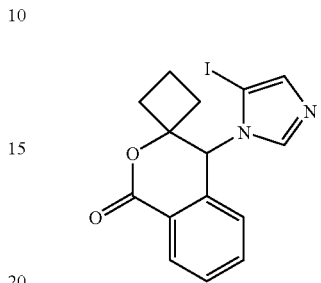

Dioxane (12 mL) and aqueous KOH (9 mmol) are added to crude N,N-diethyl-2-[(1-hydroxy-cyclobutyl)-(5-iodo-imidazol-1-yl)-methyl]-benzamide (0.61 g) and the mixture is heated to 60° C. After 30 h, the mixture is cooled to 0° C. and acidified to pH 1 with conc. HCl and the mixture is heated to 65° C. After 16 h, the mixture is diluted with ethyl acetate and washed with saturated aqueous sodium bicarbonate, water and brine. The combined aqueous phase is back-extracted twice with ethyl acetate and the combined organic phase is dried over magnesium sulfate and filtered through a cotton plug. Concentration in vacuo gave a residue which is purified by silica gel flash chromatography (methylene chloride-methanol, 49:1) to give, after trituration with chloroform, [4-(5-iodo-imidazol-1-yl)-isochroman-1-one]-3-spirocyclobutane as a pale yellow foam; MS (ESI) m/z 381.0 (M+H).

(e) [4-(5-Vinyl-imidazol-1-yl)-isochroman-1-one]-3-spirocyclobutane

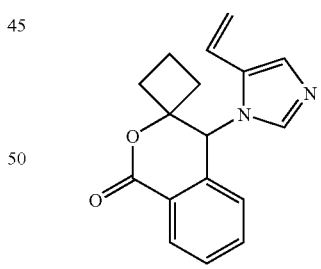

DMF (5 mL) is added to [4-(5-iodo-imidazol-1-yl)-isochroman-1-one]-3-spirocyclobutane (0.31 g, 0.77 mmol), tributylvinyltin (0.46 g, 1.39 mmol), Pd$_2$ dba$_3$.CHCl$_3$ (0.016 g, 0.015 mmol) and triphenylphosphine (0.016 g, 0.062 mmol) under nitrogen. The mixture is heated to 90° C. After 6 h, the mixture is cooled down, diluted with isopropyl acetate and washed twice with water and brine. The combined organic phase is dried over magnesium sulfate and filtered through a cotton plug. The residue is purified by silica gel flash chromatography (10% wt KF in silica gel, elution with dichloromethane-methanol, 49:1) to give [4-(5-vinyl-imidazol-1- yl)-isochroman-1-one]-3-spirocyclobutane as a pale yellow solid; MS (ESI) m/z 281.2 (M+H).

(f) [4-5-Ethyl-imidazol-1-yl)-isochroman-1-one]-3-spirocyclobutane

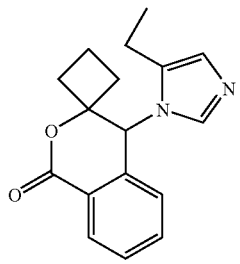

To a solution of [4-(5-vinyl-imidazol-1-yl)-isochroman-1-one]-3-spirocyclobutane (0.193 g, 0.654 mmol) in methanol (4 mL) is added Pd/C (10% wt, 0.035 g, 0.033 mmol) and the flask is flushed with hydrogen. The mixture is stirred under balloon pressure. After 3.5 h, the mixture is filtered and concentrated in vacuo. The residue is purified by silica gel flash chromatography (elution with dichloromethane-methanol, 49:1) to give [4-(5-ethyl-imidazol-1-yl)-isochroman-1-one]-3-spirocyclobutane as a very pale yellow solid (mp 178-179° C.); MS (ESI) m/z 283.1 (M+H); $^1$H NMR (400 MHz, CHLOROFORM-d) δ ppm 1.43 (t, J=7.5 Hz, 3H), 1.68-1.80 (m, 1 H), 2.03-2.15 (m, 3 H), 2.36-2.47 (m, 2 H), 2.71-2.86 (m, 2 H), 5.29 (s, 1 H), 6.85 (d, J=1.3 Hz, 1 H), 7.29-7.35 (m, 1 H), 7.31 (s, 1 H), 7.56 (td, J=7.6, 1.3 Hz, 1 H), 7.64 (td, J=7.6, 1.5 Hz, 1 H), 8.22 (dd, J=7.7, 1.4 Hz, 1 H).

(g) (R)- and (S)-[4-5-ethyl-imidazol-1-yl)-isochroman-1-one]-3-spirocyclobutane

Resolution of the enantiomers of the title compound is achieved by chiral HPLC using the ChiralPak IA column with a 4:1 heptane-isopropanol mobile phase to give enantiomer A (t$_r$=15.0 min) and enantiomer B (t$_r$=36.0 min).

Example 2

(a) N,N-Diethyl-2-[2-hydroxy-1-(5-iodo-imidazol-1-yl)-2-methyl-propyl]-benzamide

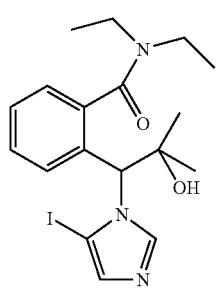

To a solution of diisopropylamine (0.97 g, 6.39 mmol) in THF (50 mL) at −78° C. under nitrogen is added n-BuLi (2.5M in hexanes, 3.8 mL, 9.6 mmol) and the mixture is warmed to 0° C. After 15 min, the LDA solution is cooled to −78° C. and a solution of N,N-diethyl-2-(5-iodo-imidazol-1-ylmethyl)-benzamide (2.45 g, 6.39 mmol) (example 1b) in THF (5 mL) is added over 15 min. 30 min after the end of addition, acetone (1.86 g, 31.97 mmol) in THF (5 mL) is added to the brown solution and the mixture is stirred for 1 h, whereupon 10% acetic acid in water is added. The mixture is poured in ethyl acetate and the two phases are separated. The organic phase is washed with saturated aqueous sodium bicarbonate. The combined aqueous phase is extracted twice with ethyl acetate. The combined organic phase is dried over MgSO$_4$, filtered through a cotton plug and concentrated in vacuo. The residue is purified by silica gel flash chromatography (elution with dichloromethane-methanol, 49:1 to 97:3 to 24:1) to afford U-4478-116 (1.65 g) as a yellow solid; MS (ESI) m/z 442.0 (M+H).

(b) 4-(5-Iodo-imidazol-1-yl)-3,3-dimethyl-isochroman-1-one

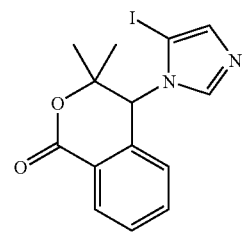

Dioxane (22 mL) and 1M aqueous KOH (22 mL, 22 mmol) are added to N,N-diethyl-2-[2-hydroxy-1-(5-iodo-imidazol-1-yl)-2-methyl-propyl]-benzamide (1.65 g) and the mixture is heated to 60° C. After 13.5 h, the mixture is cooled to 0° C. and acidified to pH=1 with conc. HCl. The mixture is heated to 60° C. After 24 h, the mixture is diluted with ethyl acetate and washed with saturated aqueous sodium bicarbonate, water and brine, dried over magnesium sulfate and filtered through a cotton plug. Concentration in vacuo gave an orange solid, which is purified by silica gel flash chromatography (methylene chloride-methanol, 49:1) to give a crystalline yellow solid; MS (ESI) m/z 369.0 (M+H); $^1$H NMR (400 MHz, CHLOROFORM-d) δ ppm 1.30 (s, 3 H), 1.57 (s, 3 H), 5.39 (s, 1 H), 7.19 (s, 1 H), 7.28 (br. d, J=7.6 Hz, 1 H), 7.39 (s, 1 H), 7.59 (td, J=7.6, 1.3 Hz, 1 H), 7.66 (td, J=7.6, 1.3 Hz, 1H), 8.27 (dd, J=7.6, 1.4 Hz, 1 H).

(c) 4-(5-Vinyl-imidazol-1-yl)-3,3-dimethyl-isochroman-1-one

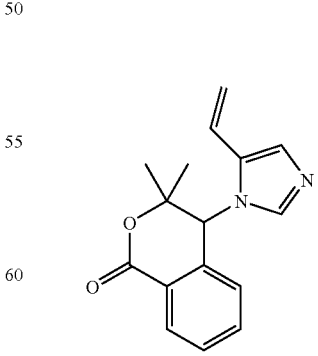

DMF (30 mL) is added to 4-(5-iodo-imidazol-1-yl)-3,3-dimethyl-isochroman-1-one (1.62 g, 4.18 mmol) (Example 2b), tributylvinyltin (2.40 g, 8.36 mmol), Pd$_2$ dba$_3$.CHCl$_3$ (0.087 g, 0.084 mmol) and triphenylphosphine (0.089 g, 0.334 mmol) under nitrogen. The mixture is heated to 90° C., to give a clear tan solution. After 3 h, the mixture is cooled down, diluted with isopropyl acetate and washed twice with water and brine. The combined organic phase is dried over magnesium sulfate and filtered through a cotton plug. The residue is purified by silica gel flash chromatography (10% wt silica gel/KF, elution with dichloromethane-methanol, 49:1 to 24:1) to give 4-(5-vinyl-imidazol-1-yl)-3,3-dimethyl-isochroman-1-one as a yellow solid; MS (ESI) m/z 269.2 (M+H); $^1$H NMR (400 MHz, MeOD) δ ppm 1.20 (s, 3 H), 1.51 (s, 3 H), 5.42 (br. s, 1 H), 5.69 (s, 1 H), 5.81 (br. s, 1 H), 6.95 (br. s, 1 H), 7.14 (br. s, 1H), 7.21 (s, 1 H), 7.42 (d, J=7.6 Hz, 1 H), 7.58-7.69 (m, 1 H), 7.70-7.80 (m, 1 H), 8.21 (dd, J=7.8, 1.3 Hz, 1 H).

(d) 4-(5-Ethyl-imidazol-1-yl)-3,3-dimethyl-isochroman-1-one

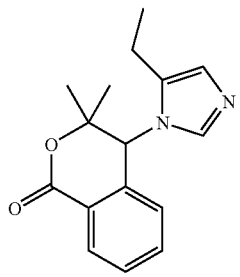

To a solution of 4-(5-vinyl-imidazol-1-yl)-3,3-dimethyl-isochroman-1-one (0.049 g, 0.173 mmol) (Example 3) in methanol (1 mL) is added Pd/C (10% wt, 0.009 g, 0.009 mmol) and the flask is flushed with hydrogen. The mixture is stirred under balloon pressure. After 3 h, another portion of catalyst (0.009 g) is added. After 7 h, the mixture is filtered and concentrated in vacuo to give 4-(5-ethyl-imidazol-1-yl)-3,3-dimethyl-isochroman-1-one as a white solid; MS (ESI) m/z 271.2 (M+H); $^1$H NMR (400 MHz, MeOD) δ ppm 1.25 (s, 3 H), 1.43 (br. s., 3 H), 1.56 (s, 3 H), 2.87 (br. s, 2 H), 5.55 (br. s, 1 H), 6.83 (s, 1 H), 7.17 (br. s, 1 H), 7.45 (d, J=7.6 Hz, 1 H), 7.67 (td, J=7.6, 1.0 Hz, 1 H), 7.78 (td, J=7.6, 1.3 Hz, 1 H), 8.24 (dd, J=7.6, 1.0 Hz, 1 H).

(e) (R)- and (S)-4-(5-Iodo-imidazol-1-yl)-3,3-dimethyl-isochroman-1-one

Resolution of the enantiomers of the title compound is achieved by chiral HPLC using the ChiralPak IA column with a 3:1 heptane-isopropanol mobile phase to give enantiomer A ($t_r$=14.4 min) and enantiomer B ($t_r$=21.4 min).

(f) (R)- and (S)-4-(5-Vinyl-imidazol-1-yl)-3,3-dimethyl-isochroman-1-one

Resolution of the enantiomers of the title compound is achieved by chiral HPLC using the ChiralPak IA column with a 7:3 heptane-ethanol mobile phase to give enantiomer A ($t_r$=14.1 min) and enantiomer B ($t_r$=15.5 min).

(g) (R)- and (S)-4-(5-Ethyl-imidazol-1-yl)-3,3-dimethyl-isochroman-1-one

Resolution of the enantiomers of the title compound is achieved by chiral HPLC using the ChiralPak IA column with a 9:1 hexanes-ethanol mobile phase to give enantiomer A ($t_r$=23.8 min) and enantiomer B ($t_r$=34.3 min).

The Following Compound can be Prepared in a Similar Fashion as Example 3:

(R)- and (S)-4-(5-Ethyl-imidazol-1-yl)-3,3-diethyl-isochroman-1-one

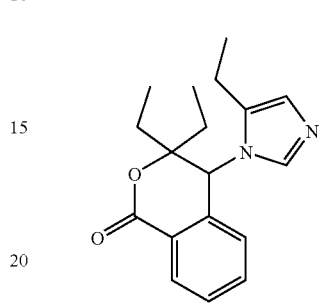

MS (ESI) m/z 299.1 (M+H); $^1$H NMR (400 MHz, CHLOROFORM-d) δ ppm 0.96 (t, J=7.3 Hz, 3 H), 0.97 (t, J=7.3 Hz, 3 H), 1.42 (t, J=7.3 Hz, 3 H), 1.46 (masked, 1 H), 1.51 (dq, J=14.6, 7.3 Hz, 1 H), 1.73 (dq, J=14.6, 7.3 Hz, 1 H), 1.95 (dq, J=14.8, 7.3 Hz, 1 H), 2.73 (q, J=7.3 Hz, 2 H), 5.16 (s, 1 H), 6.84 (s, 1 H), 7.18 (d, J=7.3 Hz, 1 H), 7.24 (s, 1 H), 7.50-7.56 (m, 1H), 7.61 (dt, J=7.3, 1.3 Hz, 1 H), 8.23 (dd, J=7.7, 1.4 Hz, 1 H)

Resolution of the enantiomers of the title compound is achieved by chiral HPLC using the ChiralPak IA column with a 9:1 heptane-isopropanol mobile phase to give enantiomer A ($t_r$=14.8 min) and enantiomer B ($t_r$=21.5 min).

(R)- and (S)-[4-(5-ethyl-imidazol-1-yl)-isochroman-1-one]-3-spirocyclopentane

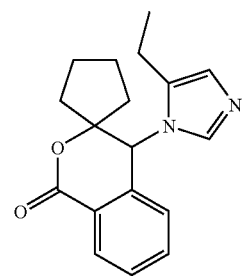

MS (ESI) m/z 297.1 (M+H); $^1$H NMR (400 MHz, CHLOROFORM-d) δ ppm 1.39 (t, J=7.5 Hz, 3 H), 1.61-2.05 (m, 8 H), 2.63-2.78 (m, 2 H), 5.12 (s, 1 H), 6.83 (d, J=1.0 Hz, 1 H), 7.22 (d, J=7.6 Hz, 1 H), 7.34 (s, 1 H), 7.54 (dt, J=7.6, 1.3 Hz, 1 H), 7.61 (dt, J=7.6, 1.3 Hz, 1 H), 8.22 (dd, J=7.6, 1.3 Hz, 1 H)

Resolution of the enantiomers of the title compound is achieved by chiral HPLC using the ChiralPak IA column with a 85:15 heptane-isopropanol mobile phase to give enantiomer A ($t_r$=17.7 min) and enantiomer B ($t_r$=31.5 min).

[4-(5-ethyl-imidazol-1-yl)-isochroman-1-one]-3-spiro(4-tetrahydropyran)

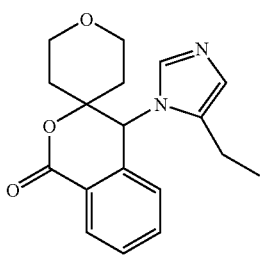

MS (ESI) m/z 313.1 (M+H); $^1$H NMR (400 MHz, CHLOROFORM-d) δ ppm 1.36-1.45 (m, 4H), 1.64-1.72 (m, 1 H), 1.81-1.89 (m, 2 H), 2.65-2.80 (m, 2 H), 3.79-3.95 (m, 4 H), 5.03 (s, 1 H), 6.86 (s, 1 H), 7.22 (br. s., 1 H), 7.24 (d, J=7.8 Hz, 1 H), 7.58 (dd, J=7.6, 1.3 Hz, 1H), 7.66 (dd, J=7.3, 1.3 Hz, 1 H), 8.26 (dd, J=7.7, 1.4 Hz, 1 H)

Example 3

(a) Tributylcyclopropyltin (CAS# 17857-70-4)

To a solution of tri-n-butyltin chloride (4 g, 11.8 mmol) in THF (20 mL) at 0° C. is added 0.5 M cyclopropylmagnesium bromide in THF (28.3 mL, 14.2 mmol). The reaction mixture is stirred under $N_2$ at ambient temperature for 4 h and poured into pH 7 aqueous buffer. The resulting mixture is extracted with diethyl ether, washed with brine, dried over magnesium sulfate and filtered through sintered funnel. The filtrate is concentrated and the residue is distilled under vacuum to give tributylcyclopropyltin as a colorless oil which is used in the next step without further purification.

(b) 4-(5-Cyclopropyl-imidazol-1-yl)-3,3-dimethyl-isochroman-1-one

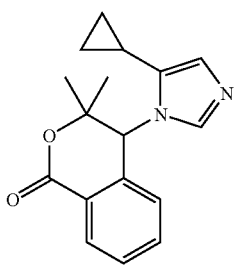

To a flask charged with 4-(5-iodo-imidazol-1-yl)-3,3-dimethyl-isochroman-1-one (350 mg, 0.95 mmol) (Example 2b), tris(dibenzylideneacetone)dipalladium(0) (98 mg, 0.095 mmol) and trifuran-2-yl-phosphane (33 mg, 0.142 mmol) and flushed with $N_2$ is added tributylcyclopropyltin (1.89 g, 5.7 mmol) in degassed N-methylpyrrolidinone (3 mL). The mixture is degassed for 15 min and heated to 95° C. for 25 h. The reaction mixture is quenched with water and extracted with ethyl acetate three times. The organic phase is combined, dried over sodium sulfate, concentrated and the residue is purified by semi-preparative reverse phase HPLC to give 4-(5-cyclopropyl-imidazol-1-yl)-3,3-dimethyl-isochroman-1-one as white solid; (ESI) m/z 283.2 (M+H); $^1$H NMR (400 MHz, MeOD) δ ppm 0.69 (s, 1 H), 0.81 (br. s, 1 H), 1.09 (br. s, 2 H), 1.29 (s, 3 H), 1.56 (s, 3 H), 1.94 (br. s, 1 H), 5.78 (s, 1 H), 6.68 (s, 1 H), 7.14 (br. s, 1 H), 7.42 (d, J=7.1 Hz, 1 H), 7.63 (td, J=7.6, 1.3 Hz, 1 H), 7.75 (td, J=7.6, 1.3 Hz, 1 H), 8.21 (dd, J=7.8, 1.3 Hz, 1 H).

(c) (R)- and (S)-4-(5-Cyclopropyl-imidazol-1-yl)-3,3-dimethyl-isochroman-1-one

Resolution of the enantiomers of the title compound is achieved by chiral HPLC using the ChiralPak OD-H column with a 4:1 heptane-isopropanol mobile phase to give enantiomer A ($t_r$=10.3 min) and enantiomer B ($t_r$=12.4 min).

Example 4

(R)- and (S)-4-(5-isopropenyl-imidazol-1-yl)-3,3-dimethyl-isochroman-1-one

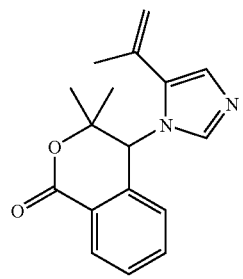

To a solution of 4-(5-iodo-imidazol-1-yl)-3,3-dimethyl-isochroman-1-one (0.700 g, 1.90 mmol) (Example 2b) in NMP (5 mL) is added tris(dibenzylideneacetone)dipalladium (0.196 g, 0.19 mmol) and trifuryl-2-yl-phospane (0.066 g, 0.285 mmol). Tributylisopropenyltin (1.25 g, 3.80 mmol) is added to the reaction mixture and it is heated to 90° C. for 24 h. The mixture is then allowed to cooled to room temperature, washed with water and extracted with ethyl acetate. The organic phase is dried over $Na_2SO_4$ and concentrated in vacuo. The residue is purified by silica gel chromatography (dichloromethane-methanol, 19:1) to give 4-(5-isopropenyl-imidazol-1-yl)-3,3-dimethyl-isochroman-1-one as a white solid; (ESI) m/z 283.0 (M+H); $^1$H NMR (400 MHz, MeOD) δ ppm 1.21 (s, 3 H), 1.50 (s, 3 H), 2.24 (br. s, 3 H), 5.31 (br. s, 1 H), 5.56 (br. s, 1 H), 5.73 (s, 1 H), 7.02 (br. s, 1 H), 7.28 (br. s, 1 H), 7.51 (d, J=7.8 Hz, 1 H), 7.69 (td, J=7.8, 1.0 Hz, 1 H), 7.81 (td, J=7.6, 1.3 Hz, 1 H), 8.25 (d, J=7.8 Hz, 1 H).

Resolution of the enantiomers of the title compound is achieved by chiral HPLC using the ChiralPak IA column with a 7:3 heptane-isopropanol mobile phase to give enantiomer A ($t_r$=8.5 min) and enantiomer B ($t_r$=11.8 min).

Example 5

(R)- and (S)-4-(5-Isopropyl-imidazol-1-yl)-3,3-dimethyl-isochroman-1-one

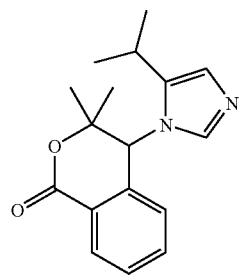

To a solution of 4-(5-isopropenyl-imidazol-1-yl)-3,3-dimethyl-isochroman-1-one (0.225 g, 0.797 mmol) (Example 4) in methanol (5 mL) is added Pd/C (0.250 g). The reaction vessel is flushed with hydrogen gas and stirred under balloon pressure for 72 h. The mixture is filtered and the filtrate concentrated in vacuo to give a 4-(5-isopropyl-imidazol-1-yl)-3,3-dimethyl-isochroman-1-one(0.210 g) as yellow solid (ESI) m/z 285.0 (M+H); $^1$H NMR (400 MHz, MeOD) δ ppm 1.24 (s, 3 H), 1.41 (d, J=6.6 Hz, 3 H), 1.45 (d, J=6.8 Hz, 3 H), 1.56 (s, 3H), 3.23 (br. s, 1 H), 5.60 (br. s, 1 H), 6.88 (br. s, 1 H), 7.15 (br. s, 1 H), 7.44 (d, J=7.3 Hz, 1H), 7.68 (td, J=7.6, 1.1 Hz, 1 H), 7.79 (td, J=7.6, 1.3 Hz, 1 H), 8.25 (dd, J=7.8, 1.3 Hz, 1 H).

Resolution of the enantiomers of the title compound is achieved by chiral HPLC using the ChiralPak IA column with a 9:1 heptane-isopropanol mobile phase to give enantiomer A ($t_r$=11.3 min) and enantiomer B ($t_r$=13.7 min).

Example 6

(a) 4-(tert-Butyl-dimethyl-silanyloxymethyl)-1-trityl-1H-imidazole

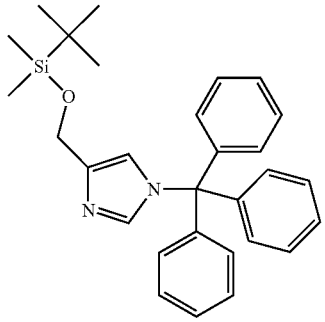

Trityl chloride (45.57 g, 0.163 mol), (1H-imidazol-4-yl)-methanol (20.00 g, 0.148 mol) and triethylamine (37.46 g, 0.370 mol) in DMF (150 mL) are stirred at r.t. for 16 h, whereupon the mixture is poured into ice-cold water. The precipitate is filtered off and dried under high vacuum to give (1-trityl-1H-imidazol-4-yl)-methanol as a solid. Crude (1-trityl-1H-imidazol-4-yl)-methanol (26.4 g, 0.077 mol), imidazole (15.88 g, 0.233 mol), DMAP (0.950 g, 7.7 mmol) and TBSCl (12.89 g, 0.085 mol) in DMF (0.1 L) are stirred at r.t. for 2 h, whereupon water is added. The mixture is extracted three times with dichloromethane. The organic layer is dried over $Na_2SO_4$ and concentrated in vacuo. The residue is purified by silica gel flash chromatography (elution with hexanes-ethyl acetate, 7:3) to yield 4-(tert-butyl-dimethyl-silanyloxymethyl)-1-trityl-1H-imidazole as a white solid; MS (ESI) m/z 243, 455 (M+H).

(b) 2-[S-(tert-Butyldimethylsilanyloxymethyl)-imidazol-1-ylmethyl]-benzonitrile

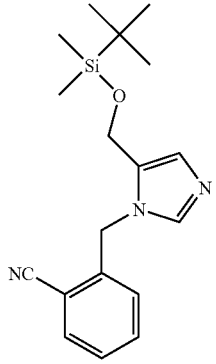

4-(tert-Butyl-dimethyl-silanyloxymethyl)-1-trityl-1H-imidazole (11.1 g, 24.4 mmol) and 2-cyanobenzyl bromide (5.02 g, 25.62 mmol) in acetonitrile (100 mL) are heated to 60° C. overnight, whereupon diethylamine (30 mL) is added. After 30 min, methanol (2 mL) is added. After 30 min the volatiles are removed in vacuo. The residue is taken up in dichloromethane and washed with water. The organic layer is dried over $Na_2SO_4$ and concentrated in vacuo. The residue is purified by silica gel flash chromatography (elution with dichloromethane-methanol, 49:1) to yield partially purified 2-[5-(tert-butyl-dimethyl-silanyloxymethyl)-imidazol-1-yl-methyl]-benzonitrile which is used in the next step without further purification; MS (ESI) m/z 328.2 (M+H).

(c) 2-{1-[5-(tert-Butyl-dimethyl-silanyloxymethyl)-imidazol-1-yl]-2-hydroxy-2-methyl-propyl}-benzonitrile

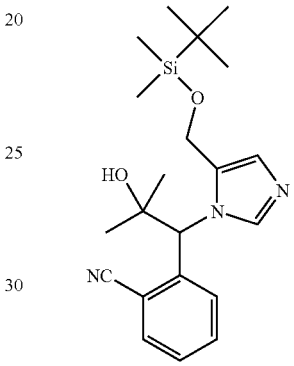

Crude 2-[5-(1-butyl-dimethyl-silariyloxymethyl)-imidazol-1-ylmethyl]-benzonitrile (56 g) is dried azeotropically with toluene then dissolved in THF (700 mL) and cooled to −75° C. LHMDS (1M in THF, 256 mL, 256 mmol) is added dropwise. Twenty min after the end of addition, acetone (14.88 g, 256.2 mmol) is added. Forty min after the end of addition, saturated aqueous sodium bicarbonate (10 mL) is added and the mixture is allowed to warm to r.t., then poured into water. After extraction with ethyl acetate the organic phase is dried over $Na_2SO_4$ and concentrated in vacuo. The residue is used in the next step without further purification; MS (ESI) m/z 386.1 (M+H).

(d) 4(5-Hydroxymethyl-imidazol-1-yl)-3,3-dimethyl-isochroman-1-one

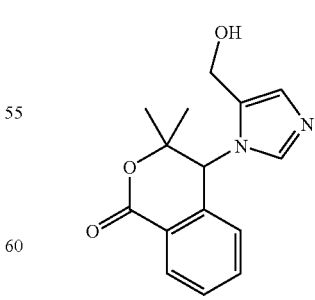

Crude 2-{1-[5-(tert-butyl-dimethyl-silanyloxymethyl)-imidazol-1-yl]-2-hydroxy-2-methyl-propyl}benzonitrile obtained in the previous reaction is dissolved in THF (1 L). Aqueous sulfuric acid (10 M, 65 mL, 650 mmol) is added and the mixture is stirred at reflux for 38 h. After cooling down, the mixture is poured in water (700 mL). The two phases are separated and the pH of the aqueous phase is adjusted to ca. 9 with aqueous sodium bicarbonate. Extraction with ethyl acetate, drying over $Na_2SO_4$ and concentration in vacuo gave 4-(5-hydroxymethyl-imidazol-1-yl)-3,3-dimethyl-isochroman-1-one as a white solid; MS (ESI) m/z 272.9 (M+H); $^1$H NMR (400 MHz, CDCl$_3$) δ ppm 1.29 (s, 3 H), 1.54 (s, 3 H), 4.71 (d, J=13.6 Hz, 1 H), 4.82 (d, J=13.9 Hz, 1 H), 5.51 (s, 1 H), 6.89 (s, 1 H), 7.29 (s, 1 H), 7.41 (d, J=7.6 Hz, 1 H), 7.53-7.58 (m, 1 H), 7.59-7.65 (m, 1 H), 8.25 (dd, J=7.6, 1.5 Hz, 1 H).

(e) (R)- and (S)-4-(5-Hydroxymethyl-imidazol-1-yl)-3,3-dimethyl-isochroman-1-one Resolution of the enantiomers of the title compound is achieved by chiral HPLC using the ChiralPak IA column with a 70:20:10 heptane-dichloromethane-ethanol mobile phase to give enantiomer A (t$_r$=7.1 min) and enantiomer B (t$_r$=8.3 min).
The Following Compounds can be Prepared in a Similar Fashion as Example 6:

7-Chloro-4-(5-hydroxymethyl-imidazol-1-yl)-3,3-dimethyl-isochroman-1-one

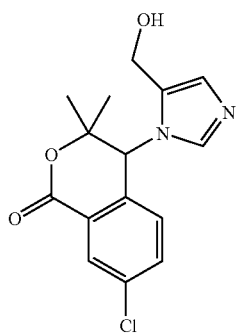

HRMS (ESI) m/z 307.0843 [(M+H)$^+$: Calcd for $C_{15}H_{16}N_2O_3Cl$: 307.0849]; $^1$H NMR (400 MHz, MeOD) δ ppm 1.26 (s, 3 H), 1.49 (s, 3 H), 4.67-4.81 (m, 2 H), 5.70 (s, 1 H), 6.96 (s, 1 H), 7.28 (br. s., 1 H), 7.57 (d, J=8.1 Hz, 1 H), 7.73 (dd, J=8.1, 2.3 Hz, 1 H), 8.17 (d, J=2.3 Hz, 1H).

(R)- and (S)-6-Chloro-4-(6-hydroxymethyl-imidazol-1-yl)-3,3-dimethyl-isochroman-1-one

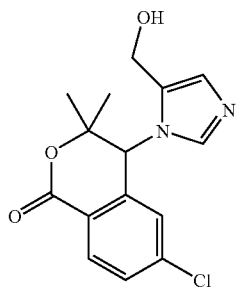

HRMS (ESI) m/z 307.0840 [(M+H)$^+$: Calcd for $C_{15}H_{16}N_2O_3Cl$: 307.0849]; $^1$H NMR (400 MHz, MeOD) δ ppm 1.30 (s, 3 H), 1.59 (s, 3 H), 4.76-4.85 (m, 2 H), 5.72 (s, 1 H), 7.02 (s, 1 H), 7.33 (br. s, 1 H), 7.67 (s, 1 H), 7.68 (dd, J=8.0, 2.2 Hz, 1 H), 8.22 (d, J=8.0 Hz, 1 H).

Resolution of the enantiomers of the title compound is achieved by chiral HPLC using the ChiralPak IA column with a 4:1 hexanes-ethanol mobile phase to give enantiomer A (t$_r$=7.5 min) and enantiomer B (t$_r$=12.7 min).

(R)- and (S)-5-Chloro-4-(5-hydroxymethyl-imidazol-1-yl)-3,3-dimethyl-isochroman-1-one

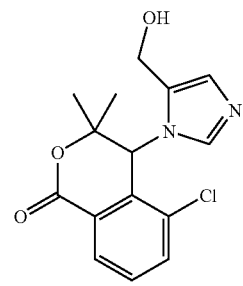

HRMS (ESI) m/z 305.0692 [(M–H)$^-$: Calcd for $C_{15}H_{14}N_2O_3Cl$: 305.0693]; $^1$H NMR (400 MHz, CHLOROFORM-d) δ ppm 1.33 (s, 3 H), 1.53 (s, 3 H), 1.87 (br. s, 1 H), 4.77-5.12 (m, 2 H), 5.61 (s, 1 H), 7.01 (s, 1 H), 7.15 (br. s, 1 H), 7.55 (t, J=7.8 Hz, 1 H), 7.70 (dd, J=8.1, 1.3 Hz, 1 H), 8.24 (dd, J=7.8, 1.0 Hz, 1 H).

Resolution of the enantiomers of the title compound is achieved by chiral HPLC using the ChiralPak IA column with a 85:15 hexanes-ethanol mobile phase to give enantiomer A (t$_r$=10.4 min) and enantiomer B (t$_r$=13.0 min).

(R)- and (S)-[4-(5-Hydroxymethyl-imidazol-1-yl)-isochroman-1-one]-3-spirocyclobutane

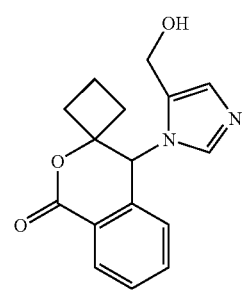

HRMS (ESI) m/z 285.1235 [(M+H)$^+$: Calcd for $C_{16}H_{15}N_2O_3$: 285.1239]; $^1$H NMR (400 MHz, CDCl$_3$) δ ppm 1.78-1.92 (m, 1 H), 1.99-2.17 (m, 3 H), 2.31-2.46 (m, 2 H), 4.78 (d, J=13.9 Hz, 1 H), 4.88 (d, J=13.9 Hz, 1 H), 5.75 (s, 1 H), 6.82 (s, 1 H), 7.34 (s, 1 H), 7.49-7.65 (m, 3 H), 8.20 (d, J=8.1 Hz, 1 H).

Resolution of the enantiomers of the title compound is achieved by chiral HPLC using the ChiralPak AS-H column with a 3:1 heptane-isopropanol mobile phase to give enantiomer A (t$_r$=10.3 min) and enantiomer B (t$_r$=16.7 min).

Example 7

(R)- and (S)-4-Chloro-4-(5-hydroxymethyl-imidazol-1-yl)-3,3-dimethyl-isochroman-1-one

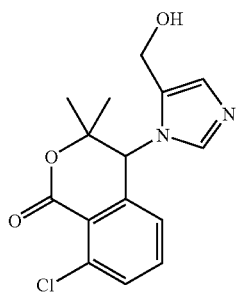

2-{1-[5-(tert-Butyldimethylsilanyloxymethyl)-imidazol-1-yl]-2-hydroxy-2-methyl-propyl}-6-chloro-benzonitrile (0.188 g, 0.616 mmol), prepared in a similar fashion as described in Example 6c is dissolved in 1,4-dioxane (5 mL). Concentrated sulfuric acid (0.130 mL, 2.46 mmol) and water (0.130 mL) are added and the mixture is stirred at reflux for 16 h. After cooling down, the mixture is basified to pH 10 using solid sodium bicarbonate and is then diluted with water and extracted with ethyl acetate twice. The combined organic phase is dried over $Na_2SO_4$ and concentration in vacuo. The residue obtained is purified by silica gel chromatography (dichloromethane-methanol, 9:1) to give 8-chloro-4-(5-hydroxymethyl-imidazol-1-yl)-3,3-dimethyl-isochroman-1-one; HRMS (ESI) m/z 307.0845 [(M+H)$^+$: Calcd for $C_{15}H_{16}N_2O_3Cl$: 307.0849]; $^1$H NMR (400 MHz, MeOD) δ ppm 1.30 (s, 3 H), 1.56 (s, 3 H), 4.77 (d, J=13.6 Hz, 1 H), 4.83 (d, J=13.6 Hz, 1 H), 5.77 (s, 1 H), 7.02 (s, 1 H), 7.35 (s, 1 H), 7.55 (br. d, J=7.3 Hz, 1 H), 7.68 (dd, J=8.0, 7.3 Hz, 1 H), 7.72 (dd, J=8.0, 1.5 Hz, 1 H).

Resolution of the enantiomers of the title compound is achieved by chiral HPLC using the Chiralcel OD column with a 85:15 heptane-ethanol mobile phase to give enantiomer A ($t_r$=29.2 min) and enantiomer B ($t_r$=31.5 min).

Example 8

4-(5-Methoxymethyl-imidazol-1-yl)-3,3-dimethyl-isochroman-1-one

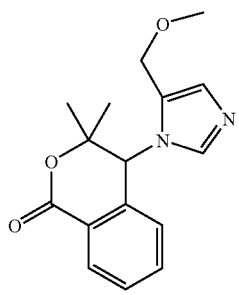

To a solution of 4-(5-hydroxymethyl-imidazol-1-yl)-3,3-dimethyl-isochroman-1-one (0.125 g, 0.495 mmol) (Example 6d) in DMF (2 mL) is added sodium hydride (0.018 g, 0.495 mmol). The reaction mixture is stirred at room temperature for 5 min and then methyl iodide (0.028 mL, 0.495 mmol) is added. The reaction is stirred for 2.5 h at room temperature. It is then washed with water and extracted with ethyl acetate twice. The organic layer is dried over $Na_2SO_4$ and concentrated in vacuo. The residue is purified by silica gel chromatography (dichloromethane-methanol, 19:1) to give 4-(5-methoxymethyl-imidazol-1-yl)-3,3-dimethyl-isochroman-1-one; MS (ESI) m/z 287.2 (M+H); $^1$H NMR (400 MHz, MeOD) δ ppm 1.70 (s, 3H), 1.77 (s, 3 H), 3.90 (s, 3 H), 4.39 (s, 2 H), 4.88 (br. s, 1 H), 6.99 (s, 1 H), 7.44-7.53 (m, 1H), 7.56-7.64 (m, 2 H), 7.76 (s, 1 H), 7.86 (d, J=7.6 Hz, 1 H).

Example 9

(a) 3-(3,3-Dimethyl-1-oxo-isochroman-4-yl)-3H-imidazole-4-carbaldehyde

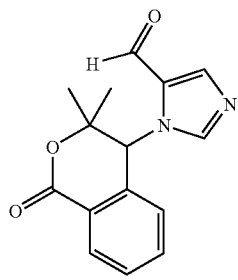

To a solution of 4-(5-hydroxymethyl-imidazol-1-yl)-3,3-dimethyl-isochroman-1-one (0.500 g, 1.84 mmol) (Example 6d) in dioxane (10 mL) is added manganese dioxide (2.4 g, 27.6 mmol) and the reaction mixture is heated to 60° C. overnight. Filtration through celite and concentration in vacuo afforded 3-(3,3-dimethyl-1-oxo-isochroman-4-yl)-3H-imidazole-4-carbaldehyde, which is used in the next step without further purification; MS (ESI) m/z 271.1 (M+H).

(b) 4-(5-But-1-enyl-imidazol-1-yl)-3,3-dimethyl-isochroman-1-one

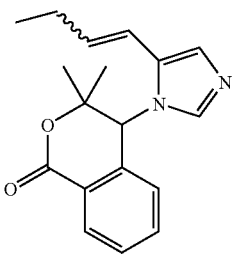

To a solution of propyltriphenylphosphonium bromide (0.157 g, 0.41 mmol) in THF (1 mL) at −78° C. is added sodium hexamethyldisilylamide (1M in THF, 0.44 mL, 0.44 mmol) and the mixture is allowed to warm to ambient temperature over 10 min. This solution is cooled to −20° C. and 3-(3,3-dimethyl-1-oxo-isochroman-4-yl)-3H-imidazole-4-carbaldehyde (0.10 g, 0.37 mmol) in THF (0.2 mL) is added. The cooling bath is removed and the mixture is stirred at ambient temperature overnight, then filtered. The filtrate is concentrated in vacuo to give the crude 4-(5-but-1-enyl-imidazol-1-yl)-3,3-dimethyl-isochroman-1-one which is used in the next step without further purification; MS (ESI) m/z 297.1 (M+H).

(c) 4-(5-Butyl-imidazol-1-yl)-3,3-dimethyl-isochroman-1-one

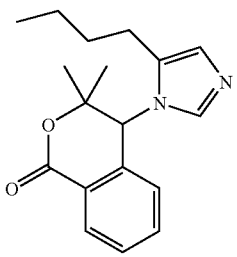

To a solution of 4-(5-but-1-enyl-imidazol-1-yl)-3,3-dimethyl-isochroman-1-one (0.110 g, 0.37 mmol) in methanol (2 mL) is added Pd/C (0.020 g). The reaction vessel is flushed with hydrogen gas and stirred under balloon pressure overnight. The mixture is filtered and the filtrate concentrated in vacuo to give a residue which is purified by semi-preparative reverse phase HPLC to give 4-(5-butyl-imidazol-1-yl)-3,3-dimethyl-isochroman-1-one as a white solid; MS (ESI) m/z 299.1 (M+H); $^1$H NMR (400 MHz, MeOD) δ ppm 1.02 (br. s, 3 H), 1.22 (s, 3 H), 1.53 (br. s, 5 H), 1.77 (br. s, 2 H), 2.81 (br. s, 2 H), 5.54 (br. s, 1 H), 6.82 (s, 1H), 7.19 (br. s, 1 H), 7.39 (d, J=7.3 Hz, 1 H), 7.60-7.67 (m, 1 H), 7.71-7.78 (m, 1 H), 8.21 (d, J=7.8 Hz, 1 H).

The Following Compounds can be Prepared in a Similar Fashion as Example 9:

(R)- and (S)-4-(5-Propyl-imidazol-1-yl)-3,3-dimethyl-isochroman-1-one

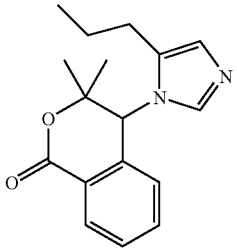

MS (ESI) m/z 285.0 (M+H); $^1$H NMR (400 MHz, MeOD) δ ppm 1.11 (br. s, 3 H), 1.22 (s, 3 H), 1.53 (s, 3 H), 1.82 (br. s, 2 H), 2.80 (br. s, 2 H), 5.55 (br. s, 1 H), 6.84 (s, 1 H), 7.23 (br. s, 1 H), 7.40 (d, J=7.8 Hz, 1 H), 7.59-7.68 (m, 1 H), 7.71-7.80 (m, 1 H), 8.21 (dd, J=7.8, 1.3 Hz, 1 H)

Resolution of the enantiomers of the title compound is achieved by chiral HPLC using the ChiralPak IA column with a 9:1 heptane-isopropanol mobile phase to give enantiomer A (t$_r$=20.0 min) and enantiomer B (t$_r$=22.1 min).

(R)- and (S)-[4-(5-propyl-imidazol-1-yl)-isochroman-1-one]-3-spirocyclobutane

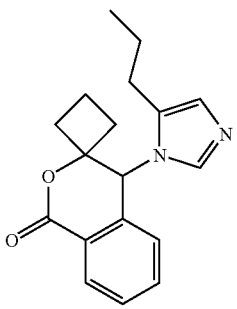

HRMS (ESI) m/z 297.1592 [(M+H)$^+$: Calcd for $C_{18}H_{20}N_2O_2$: 297.1603]; $^1$H NMR (400 MHz, MeOD) δ ppm 1.11 (t, J=7.3 Hz, 3 H), 1.74-1.86 (m, 2 H), 1.87-1.96 (m, 1 H), 2.00-2.10 (m, 2 H), 2.19-2.26 (m, 1 H), 2.27-2.36 (m, 2 H), 2.75-2.92 (m, 2 H), 5.78 (s, 1 H), 6.80 (s, 1 H), 7.25 (s, 1 H), 7.54 (d, J=7.8 Hz, 1 H), 7.59-7.67 (m, 1 H), 7.73-7.78 (m, 1 H), 8.17 (d, J=7.8 Hz, 1 H)

Resolution of the enantiomers of the title compound is achieved by chiral HPLC using the ChiralPak IA column with a 4:1 heptane-isopropanol mobile phase to give enantiomer A (t$_r$=10.0 min) and enantiomer B (t$_r$=18.8 min).

Example 10

(a) 4-[5-(2-Methoxyvinyl)-imidazol-1-yl]-3,3-dimethyl-isochroman-1-one

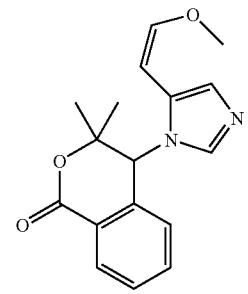

To a solution of methoxymethyltriphenylphosphonium chloride (0.974 g, 2.84 mmol) in THF (10 mL) at −78° C. is added sodium hexamethyldisilazide (1M in THF, 3.0 mL, 3.09 mmol) and the mixture is stirred at −78° C. for 1 h. 3-(3,3-dimethyl-1-oxo-isochroman-4-yl)-3H-imidazole-4-carbaldehyde (0.10 g, 0.37 mmol) (Example 9a) in THF (0.2 mL) is then added at −78° C. and the mixture is stirred at ambient temperature overnight. It is then quenched with water and extracted with ethyl acetate. The organic phase is concentrated in vacuo. The residue is purified using by semi-preparative reverse phase HPLC to afford 4-[5-(2-methoxyvinyl)-imidazole-1-yl]-3,3-dimethyl-isochroman-1-one; $^1$H NMR (400 MHz, CHLOROFORM-d) δ ppm 1.31 (s, 3 H), 1.52 (s, 3 H), 3.75 (br. s, 3 H), 5.22 (s, 1 H), 5.31 (s, 1 H), 5.55 (br. s, 1 H), 6.82 (br. s, 1 H), 6.96 (br. s, 1 H), 7.16 (d, J=7.6 Hz, 1 H), 7.55 (td, J=7.6, 1.3 Hz, 1 H), 7.63 (td, J=7.6, 1.3 Hz, 1 H), 8.24 (dd, J=7.7, 1.4 Hz, 1 H).

(b) 4-[5-(2-Methoxy-ethyl)-imidazol-1-yl]-3,3-dimethyl-isochroman-1-one

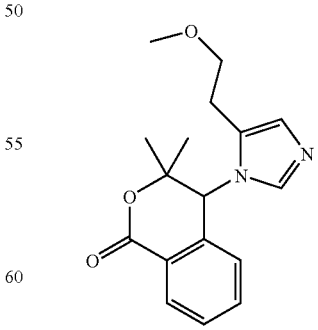

To a solution of 4-[5-(2-methoxy-vinyl)-imidazole-1-yl]-3,3-dimethyl-isochroman-1-one (0.110 g, 0.37 mmol) in methanol (5 mL) is added Pd/C (0.020 g). The reaction vessel is flushed with hydrogen gas and stirred under balloon pressure for 72 h. The mixture is filtered, and the filtrate concentrated in vacuo to give a residue which is purified by silica gel chromatography (dichloromethane-methanol, 19:1) to give 4-[5-(2-methoxy-ethyl)-imidazol-1-yl]-3,3-dimethyl-isochroman-1-one as a white solid; HRMS (ESI) m/z 301.1555 [(M+H)⁺: Calcd for $C_{17}H_{20}N_2O_3$: 301.1552]; ¹H NMR (400 MHz, MeOD) δ ppm 1.25 (s, 3 H), 1.56 (s, 3H), 3.13 (br. s, 2 H), 3.45 (br. s, 3 H), 3.70-3.79 (m, 2 H), 5.71 (s, 1 H), 6.90 (s, 1 H), 7.15 (br. s, 1 H), 7.52 (d, J=7.6 Hz, 1 H), 7.60-7.72 (m, 1 H), 7.74-7.86 (m, 1 H), 8.24 (dd, J=7.8, 1.5 Hz, 1 H)

(c) (R)- and (S)-4-[5-(2-Methoxy-ethyl)-imidazol-1-yl]-3,3-dimethyl-isochroman-1-one Resolution of the enantiomers of the title compound is achieved by chiral HPLC using the ChiralPak IA column with a 65:35 hexanes-reagent alcohol mobile phase to give enantiomer A ($t_r$=9.2 min) and enantiomer B ($t_r$=11.8 min).

Example 11

(a) 4-[5-(2-Ethoxy-ethyl)-imidazol-1-yl]-3,3-dimethyl-isochroman-1-one

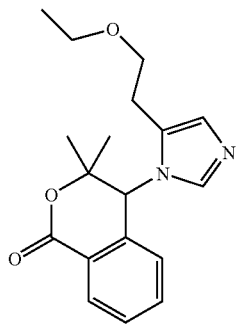

To a solution of ethoxymethyltriphenylphosphonium chloride (0.426 g, 1.2 mmol) in THF (5 mL) at ambient temperature is added lithium hexamethyldisilazide (1M in THF, 1.3 mL, 1.3 mmol) and the mixture is stirred for 15 min. 3-(3,3-Dimethyl-1-oxo-isochroman-4-yl)-3H-imidazole-4-carbaldehyde (0.27 g, 1.0 mmol) (Example 9a) in THF (5 mL) and the mixture is stirred at ambient temperature overnight, then filtered. The filtrate is concentrated in vacuo to give crude 4-[5-(2-ethoxy-vinyl)-imidazol-1-yl]-3,3-dimethyl-isochroman-1-one, which is redissolved in methanol (5 mL). Pd/C (0.500 g) is added and the reaction vessel is flushed with hydrogen gas and stirred under balloon pressure at 50° C. overnight. The mixture is filtered, and the filtrate is concentrated in vacuo to give a residue which is purified by semi-preparative reverse phase HPLC to give 4-[5-(2-ethoxy-ethyl)-imidazol-1-yl]-3,3-dimethyl-isochroman-1-one as a white solid; MS (ESI) m/z 315.0 (M+H); ¹H NMR (400 MHz, MeOD) of the HCl salt δ ppm 1.25 (t, J=6.9 Hz, 3 H), 1.32 (s, 3 H), 1.62 (s, 3 H), 3.29-3.37 (m, 2 H), 3.60-3.69 (m, 2 H), 3.79-3.97 (m, 2 H), 6.09 (s, 1 H), 7.57 (s, 1 H), 7.64 (d, J=7.6 Hz, 1 H), 7.73-7.79 (m, 1 H), 7.81-7.88 (m, 1 H), 8.32 (dd, J=7.7, 1.4 Hz, 1 H), 8.63 (br. s, 1H)

(b) (R)- and (S)-4-[5-(2-Ethoxyethyl)-imidazol-1-yl]-3,3-dimethyl-isochroman-1-one Resolution of the enantiomers of the title compound is achieved by chiral HPLC using the ChiralPak IA column with a 7:3 heptane-ethanol mobile phase to give enantiomer A ($t_r$=7.9 min) and enantiomer B ($t_r$=9.3 min).

Example 12

(R,R)-, (S,S)-, (R,S)-, (S,R)-4-[5-(1-Hydroxy-ethyl)-imidazol-1-yl]-3,3-dimethyl-isochroman-1-one

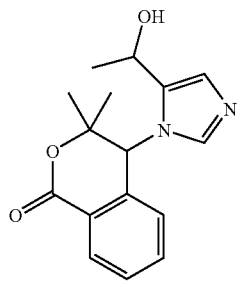

To a solution of 3-(3,3-dimethyl-1-oxo-isochroman-4-yl)-3H-imidazole-4-carbaldehyde (0.500 g, 1.852 mmol) (Example 9a) in THF (20 mL) at −78° C. is added 1M methyl magnesium bromide in dibutyl ether (2.41 mL, 2.41 mmol). The reaction mixture is stirred at −78° C. for 3 h, whereupon acetone (2 mL) is added. The mixture is allowed to warm to ambient temperature and then poured into water (50 mL). The mixture is extracted with ethyl acetate. The combined organic phase is washed with water, dried over $Na_2SO_4$ and concentrated in vacuo. The residue is purified by silica gel chromatography (gradient methanol in dichloromethane, 1% to 5%) to give 4-[5-(1-hydroxy-ethyl)-imidazol-1-yl]-3,3-dimethyl-isochroman-1-one as a white solid. Resolution of all four stereoisomers of the title compound is achieved by chiral HPLC. Stereoisomer A is separated with a ChiralPak IA column using an 85:15 heptane-isopropanol mobile phase. The remaining three stereoisomers are resolved with a ChiralPak AD using an 85:15 heptane-ethanol mobile phase to give stereoisomer B ($t_r$=61.4 min), stereoisomer C ($t_r$=76.7 min) and stereoisomer D ($t_r$=94.9 min)

(R,S) and (S,R) isomers (stereoisomer A and D): MS (ESI) m/z 287.0 (M+H); ¹H NMR (400 MHz, CDCl₃) δ ppm 1.26 (s, 3 H), 1.54 (s, 3 H), 1.79 (d, J=6.6 Hz, 3 H), 1.84 (d, J=8.6 Hz, 1 H), 4.91-5.01 (m, 1 H), 5.67 (s, 1 H), 7.01 (s, 1 H), 7.24 (s, 1 H), 7.47 (d, J=8.1 Hz, 1H), 7.52-7.58 (m, 1 H), 7.59-7.64 (m, 1 H), 8.25 (dd, J=7.7, 1.4 Hz, 1 H)

(R,R) and (S,S) isomers (stereoisomer B and C): MS (ESI) m/z 287.1 (M+H); ¹H NMR (400 MHz, CDCl₃) δ ppm 1.40 (s, 3 H), 1.56 (s, 3 H), 1.77 (d, J=6.6 Hz, 3 H), 1.85 (br. s, 1 H), 5.06-5.12 (m, 1 H), 5.60 (s, 1 H), 6.99 (s, 1 H), 7.23 (d, J=7.6 Hz, 1 H), 7.40 (s, 1 H), 7.54 (td, J=7.8, 1.3 Hz, 1 H), 7.61 (td, J=7.6, 1.5 Hz, 1 H), 8.24 (dd, J=7.7, 1.4 Hz, 1 H)

Example 13

4-5-Acetyl-imidazol-1-yl)-3,3-dimethyl-isochroman-1-one

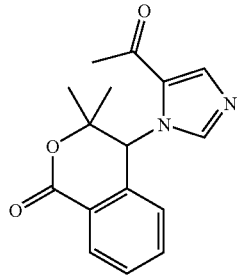

To a solution of 4-[5-(1-hydroxy-ethyl)-imidazol-1-yl]-3,3-dimethyl-isochroman-1-one (0.100 g, 0.35 mmol) (Example 12) in dioxane (2 mL) is added manganese dioxide (0.46 g, 5.2 mmol) and the reaction mixture is heated to 60° C.

overnight. Filtration through celite and concentration in vacuo gave a residue, which is purified by semi-preparative reverse phase HPLC to give 4-(5-acetyl-imidazol-1-yl)-3,3-dimethyl-isochroman-1-one as a white solid; MS (ESI) m/z 285.0 (M+H); $^1$H NMR (400 MHz, CDCl$_3$) δ ppm 1.22 (s, 3 H), 1.55 (s, 3 H), 2.61 (s, 3 H), 6.90 (s, 1 H), 7.38 (d, J=7.1 Hz, 1 H), 7.47 (s, 1 H), 7.57-7.62 (m, 1 H), 7.63-7.69 (m, 1 H), 7.93 (s, 1 H), 8.28 (dd, J=7.6, 1.5 Hz, 1 H).

Example 14

3-(3,3-Dimethyl-1-oxo-isochroman-4-yl)-3H-imidazole-4-carbaldehyde Oxime

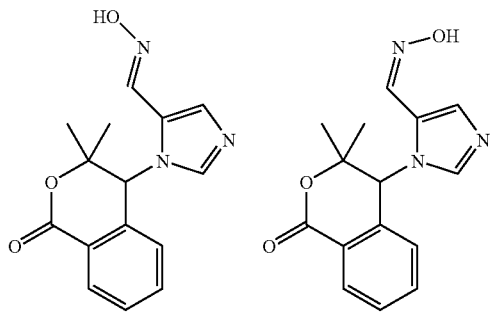

3-(3,3-Dimethyl-1-oxo-isochroman-4-yl)-3H-imidazole-4-carbaldehyde (0.100 g, 0.363 mmol) (Example 9a) in ethanol (3 mL) is added to NaHCO$_3$ (0.246 g, 2.901 mmol) and hydroxylamine hydrochloride (0.208 g, 2.901 mmol) in water (1 mL). After 1 hr, water is added and the mixture is extracted three times with dichloromethane. The combined organic phase is dried over magnesium sulfate and filtered through a cotton plug. Concentration in vacuo gives a residue, which is purified by silica gel flash chromatography (elution with dichloromethane-methanol, 49:1), resulting in the separation of the two isomers. Each isomer is obtained as a white solid.

Cis isomer: MS (ESI) m/z 286.0 (M+H); $^1$H NMR (400 MHz, MeOD) δ ppm 1.25 (s, 3 H), 1.59 (s, 3 H), 5.99 (s, 1 H), 7.27 (br. s, 1 H), 7.52 (d, J=7.6 Hz, 1 H), 7.71 (t, J=7.7 Hz, 1 H), 7.76-7.86 (m, 1 H), 7.95 (br. s, 1 H), 8.05 (s, 1 H), 8.28 (d, J=7.8 Hz, 1 H).

Trans isomer: MS (ESI) m/z 285.9 (M+H); $^1$H NMR (400 MHz, MeOD) δ ppm 1.29 (s, 3 H), 1.55 (s, 3 H), 6.81 (s, 1 H), 7.30 (s, 1 H), 7.32 (s, 1 H), 7.50 (d, J=7.6 Hz, 1 H), 7.64-7.73 (m, 1 H), 7.75-7.83 (m, 1 H), 8.26 (dd, J=7.8, 1.5 Hz, 1 H), 8.32 (s, 1 H).

Example 15

4-(5-Ethylaminomethyl-imidazol-1-yl)-3,3-dimethyl-isochroman-1-one

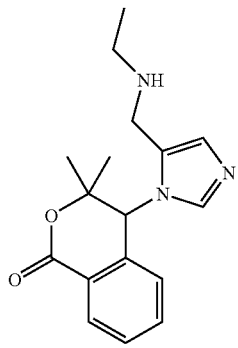

To a solution of 3-(3,3-dimethyl-1-oxo-isochroman-4-yl)-3H-imidazole-4-carbaldehyde (0.133 g, 0.49 mmol) (Example 9a) in dichloroethane (2 mL) is added ethylamine (0.37 mL, 0.738 mmol) and sodium triacetoxyborohydride (0.313 g, 1.477 mmol). The reaction mixture is stirred at 50° C. for 5 h. The mixture is cooled to room temperature, washed with saturated aqueous sodium bicarbonate and is extracted with ethyl acetate. The organic phase is dried over Na$_2$SO$_4$ and concentrated in vacuo. The residue is dissolved in methanol (5 mL) and purified by reverse phase HPLC to give 4-(5-ethylaminomethyl-imidazol-1-yl)-3,3-dimethyl-isochroman-1-one; HRMS (ESI) m/z 300.1705 [(M+H)$^+$: Calcd for C$_{17}$H$_{22}$N$_3$O$_2$: 300.1712]; $^1$H NMR (400 MHz, MeOD) of the TFA salt δ ppm 1.27 (s, 3 H), 1.46 (t, J=6.8 Hz, 3 H), 1.59 (s, 3 H), 3.35-3.40 (m, 2 H), 4.65 (br. s, 2 H), 5.82 (s, 1 H), 7.51 (br. s, 1 H), 7.64 (d, J=7.3 Hz, 1 H), 7.75 (td, J=7.8, 1.0 Hz, 1 H), 7.84 (td, J=7.6, 1.3 Hz, 1 H), 7.92 (br. s, 1 H), 8.30 (dd, J=7.8, 1.3 Hz, 1 H).

The Following Compound can be Prepared in a Similar Fashion as Example 15:

4-(5-Dimethylaminomethyl-imidazol-1-yl)-3,3-dimethyl-isochroman-1-one

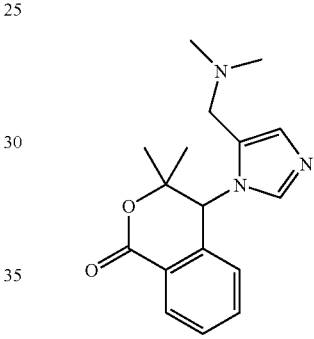

MS (ESI) m/z 300.0 (M+H); $^1$H NMR (400 MHz, MeOD) of the TFA salt δ ppm 1.25 (s, 3 H), 1.58 (s, 3 H), 2.93 (br. s, 6 H), 4.62 (br. s, 2 H), 5.94 (s, 1 H), 7.60 (d, J=7.8 Hz, 1 H), 7.63 (s, 1 H), 7.75 (td, J=7.8, 1.3 Hz, 1 H), 7.83 (td, J=7.6, 1.5 Hz, 1 H), 8.04 (br. s, 1 H), 8.30 (dd, J=7.8, 1.3 Hz, 1 H).

Example 16

(a) 4-(5-Difluoromethyl-imidazol-1-yl)-3,3-dimethyl-isochroman-1-one

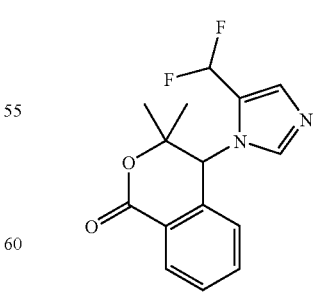

To a solution of 3-(3,3-dimethyl-1-oxo-isochroman-4-yl)-3H-imidazole-4-carbaldehyde (0.098 g, 0.355 mmol) (Example 9a) in dichloromethane (3 mL) at 0° C. under nitrogen is added DAST (0.301 g, 1.777 mmol) dropwise and the cooling bath is removed. After 2 h, the solvent is removed in vacuo and the residue is taken up in dichloroethane (3 mL) and refluxed. After another 2 h, an additional portion of DAST (0.060 g, 0.372 mmol) is added. The mixture is then diluted with dichloromethane, the organic phase is shaken with saturated aqueous sodium bicarbonate and filtered through celite. The organic phase is dried over magnesium sulfate and filtered through a cotton plug. The residue is purified by silica gel flash chromatography (elution with heptane-ethyl acetate, 3:2 to 1:1 to 2:3) to give 4-(5-difluoromethyl-imidazol-1-yl)-3,3-dimethyl-isochroman-1-one as a pale yellow crystalline solid; MS (ESI) m/z 293.0 (M+H); $^1$H NMR (400 MHz, CHLOROFORM-D) δ ppm 1.32 (s, 3 H), 1.57 (s, 3 H), 5.50 (s, 1 H), 6.86 (t, J=52.7 Hz, 1 H), 7.32 (t, J=2.6 Hz, 1 H), 7.43 (s, 1H), 7.44 (m, 1 H), 7.54-7.63 (m, 1 H), 7.63-7.71 (m, 1 H), 8.27 (dd, J=7.7, 1.3 Hz, 1 H).

(b) (R)- and (S)-4-(5-Difluoromethyl-imidazol-1-yl)-3,3-dimethyl-isochroman-1-one Resolution of the enantiomers of the title compound is achieved by chiral HPLC using the ChiralPak IA column with a 3:1 heptane-isopropanol mobile phase to give enantiomer A ($t_r$=13.3 min) and enantiomer B ($t_r$=21.4 min).

Example 17

(a) 4-(5-Fluoromethyl-imidazol-1-yl)-3,3-dimethyl-isochroman-1-one

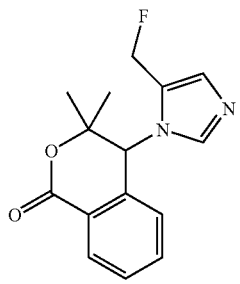

To a solution of 4-(5-hydroxymethyl-imidazol-1-yl)-3,3-dimethyl-isochroman-1-one (0.158 g, 0.574 mmol) (Example 6d) in dichloromethane (7 mL) at 0° C. under nitrogen is added DAST (0.487 g, 2.872 mmol) dropwise. The mixture is stirred at 0° C. overnight. After dilution with dichloromethane, the organic phase is washed twice with saturated aqueous sodium bicarbonate, water and brine. The combined aqueous phase is back-extracted once with dichloromethane. The combined organic phase is dried over magnesium sulfate and filtered through a cotton plug. The residue is purified by silica gel flash chromatography (elution with dichloromethane-methanol, 99:1 to 49:1) to afford 4-(5-fluoromethyl-imidazol-1-yl)-3,3-dimethyl-isochroman-1-one as a white solid; MS (ESI) m/z 275.0 (M+H); $^1$H NMR (400 MHz, CHLOROFORM-d) δ ppm 1.31 (s, 3 H), 1.57 (s, 3 H), 5.27 (s, 1 H), 5.45 (dd, J=22.7, 12.4 Hz, 1 H), 5.58 (dd, J=21.2, 12.4 Hz, 1 H), 7.21 (d, J=5.3 Hz, 1 H), 7.29 (d, J=7.3 Hz, 1 H), 7.38 (d, J=2.8 Hz, 1 H), 7.55-7.61 (m, 1 H), 7.65 (dd, J=7.6, 1.5 Hz, 1 H), 8.27 (dd, J=7.7, 1.4 Hz, 1 H).

(b) (R)- and (S)-4-(5-Fluoromethyl-imidazol-1-yl)-3,3-dimethyl-isochroman-1-one

Resolution of the enantiomers of the title compound is achieved by chiral HPLC using the ChiralPak IA column with a 3:1 heptane-isopropanol mobile phase to give enantiomer A ($t_r$=13.3 min) and enantiomer B ($t_r$=21.4 min).

Example 18

(R)- and (S)-4-(5-Methyl-imidazol-1-yl)-3,3-dimethyl-isochroman-1-one

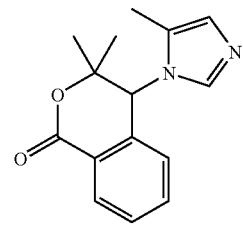

A solution of 4-(5-hydroxymethyl-imidazol-1-yl)-3,3-dimethyl-isochroman-1-one (0.300 g, 1.1 mmol) (Example 6d) in thionyl chloride (3 mL) is refluxed overnight. The volatiles are removed in vacuo to give 4-(5-chloromethyl-imidazol-1-yl)-3,3-dimethyl-isochroman-1-one, which is redissolved in methanol (10 mL). The solution is injected in an H-Cube™ using a Pd on carbon cartridge at 0.5 mL/min, 100 bar $H_2$ and 50° C. The solution eluting from the cartridge is collected and concentrated in vacuo. The residue is purified by semi-preparative reverse phase HPLC to give 3,3-dimethyl-4-(5-methyl-imidazol-1-yl)-isochroman-1-one as a white solid; MS (ESI) m/z 257.0 (M+H); $^1$H NMR (400 MHz, CDCl$_3$) δ ppm 1.34 (s, 3 H), 1.58 (s, 3 H), 2.38 (br. s, 3 H), 5.18 (br. s, 1 H), 6.92 (s, 1 H), 7.17 (br. s, 1 H), 7.35 (br. s, 1 H), 7.58 (t, J=7.6 Hz, 1 H), 7.62-7.68 (m, 1 H), 8.26 (d, J=7.8 Hz, 1 H).

Resolution of the enantiomers of the title compound is achieved by chiral HPLC using the ChiralPak IA column with a 7:3 heptane-isopropanol mobile phase to give enantiomer A ($t_r$=10.8 min) and enantiomer B ($t_r$=17.8 min).

Example 19

(R)- and (S)-4-(5-Ethoxymethyl-imidazol-1-yl)-3,3-dimethyl-isochroman-1-one

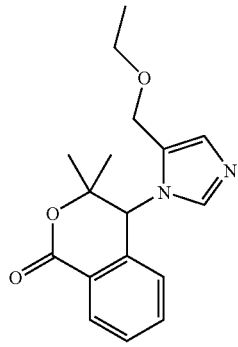

To a solution of 4-(5-chloromethyl-imidazol-1-yl)-3,3-dimethyl-isochroman-1-one (0.150 g, 0.516 mmol), prepared as described in Example 18, in anhydrous ethanol (5 mL) is added diisopropylethyl amine (0.100 g, 0.77 mmol) and the mixture is stirred at reflux overnight. The mixture is purified by semi-preparative reverse phase HPLC to give 4-(5-ethoxymethyl-imidazol-1-yl)-3,3-dimethyl-isochroman-1-one as a white solid; MS (ESI) m/z 301.0 (M+H); $^1$H NMR (400 MHz, MeOD) δ ppm 1.26 (s, 3 H), 1.29 (t, J=6.1 Hz, 3 H), 1.54 (s, 3 H), 3.62 (br. s, 2 H), 4.70 (br. s, 2 H), 5.59 (s, 1

H), 7.02 (s, 1 H), 7.29 (br. s, 1 H), 7.52 (d, J=7.8 Hz, 1 H), 7.63 (td, J=7.8, 1.3 Hz, 1 H), 7.74 (td, J=7.6, 1.3 Hz, 1 H), 8.21 (dd, J=7.8, 1.3 Hz, 1H).

Resolution of the enantiomers of the title compound is achieved by chiral HPLC using the ChiralPak IA column with a 7:2:1 heptane-dichloromethane-ethanol mobile phase to give enantiomer A ($t_r$=8.9 min) and enantiomer B ($t_r$=6.3 min).

The Following Compound can be Prepared in a Similar Fashion as Example 19:

4-[5-(2-Hydroxy-ethoxymethyl)-imidazol-1-yl]-3,3-dimethyl-isochroman-1-one

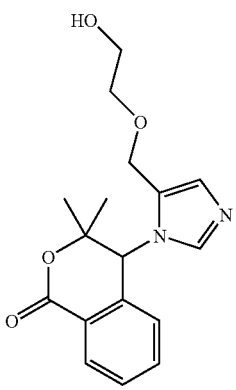

MS (ESI) m/z 317.0 (M+H); $^1$H NMR (400 MHz, CDCl$_3$) δ ppm 1.31 (s, 3 H), 1.55 (s, 3 H), 1.76 (br. s, 1 H), 3.55-3.69 (m, 2 H), 3.78-3.86 (m, 2 H), 4.65-4.75 (m, 2 H), 5.46 (s, 1 H), 7.06 (s, 1 H), 7.34 (d, J=8.3 Hz, 2 H), 7.55 (td, J=7.6, 1.3 Hz, 1 H), 7.62 (td, J=7.6, 1.5 Hz, 1H), 8.25 (dd, J=7.8, 1.5 Hz, 1 H)

Example 20

(a) 3-(3,3-Dimethyl-1 oxo-isochroman-4-yl)-3H-imidazole-4-carbonitrile

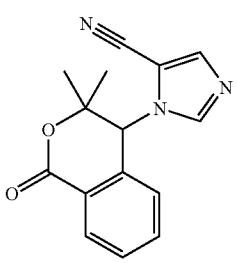

To a solution of 4-(5-hydroxymethyl-imidazol-1-yl)-3,3-dimethyl-isochroman-1-one (1.0 g, 3.76 mmol) (Example 6d) in THF (30 mL) is added magnesium sulfate (4.79 g, 0.055 mol) and ammonia (2M isopropanol, 9 mL, 0.018 mol). Manganese dioxide (9 mL, 0.055 mol) is then added and the reaction mixture is stirred at room temperature for 48 h. Filtration through celite and concentration in vacuo affords a residue, which is purified by reverse-phase HPLC to give 3-(3,3-dimethyl-1-oxo-isochroman-4-yl)-3H-imidazole-4-carbonitrile; MS (ESI) m/z 268.0 (M+H); $^1$H NMR (400 MHz, MeOD) δ ppm 1.33 (s, 3 H), 1.60 (s, 3 H), 5.87 (s, 1 H), 7.57 (d, J=7.6 Hz, 1 H), 7.67-7.78 (m, 1 H), 7.78-7.98 (m, 3 H), 8.28 (dd, J=7.7, 1.4 Hz, 1 H).

(b) (R)- and (S)-3-(3,3-Dimethyl-1-oxo-isochroman-4-yl)-3H-imidazole-4-carbonitrile Resolution of the enantiomers of the title compound is achieved by chiral HPLC using the ChiralPak IA column with a 7:3 heptane-ethanol mobile phase to give enantiomer A ($t_r$=13.5 min) and enantiomer B ($t_r$=42.7 min).

Example 21

4-(5-Amino-methyl-imidazol-1-yl)-3,3-dimethyl-isochroman-1-one

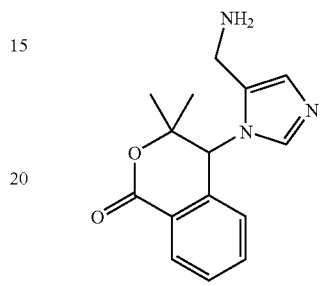

The solution of 3-(3,3-dimethyl-1-oxo-isochroman-4-yl)-3H-imidazole-4-carbonitrile (0.130 g, 0.5 mmol) (Example 20) in THF (2 mL) is added borane dimethyl sulfide complex (0.055 mL, 0.55 mmol) dropwise, and the resulting mixture is stirred at reflux for 30 min. The reaction mixture is concentrated in vacuo and the residue is redissolved in THF (2 mL) and 0.5 M hydrogen chloride in methanol (1.1 mL, 0.55 mmol) is added dropwise. The reaction mixture is stirred at ambient temperature for 1.5 h. The mixture is concentrated in vacuo and the residue is purified by semi-preparative reverse phase HPLC to give 4-(5-aminomethyl-imidazol-1-yl)-3,3-dimethyl-isochroman-1-one as a yellowish solid; MS (ESI) m/z 271.9 (M+H); $^1$H NMR (400 MHz, CDCl$_3$) δ ppm 1.28 (s, 3 H), 1.59 (s, 3 H), 4.55-4.74 (m, 2 H), 5.99 (s, 1 H), 7.67-7.76 (m, 3 H), 7.82 (td, J=7.6, 1.5 Hz, 1 H), 8.29 (dd, J=7.7, 1.4 Hz, 1H), 8.52 (br. s, 1 H)

Example 22

(a) 3-(3,3-Dimethyl-1-oxo-isochroman-4-yl)-3H-imidazole-4-carboxylic Acid Ethyl Ester

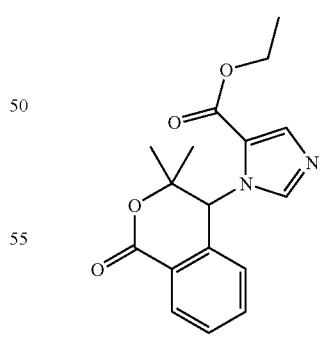

To a solution of 4-(5-hydroxymethyl-imidazol-1-yl)-3,3-dimethyl-isochroman-1-one (0.56 g, 2.0 mmol) (Example 6d) in THF (10 mL) is added ethanol (0.6 mL), sodium cyanide (0.111 g, 2.26 mmol) and manganese dioxide (2.69 g, 30.9 mmol). The mixture is stirred at reflux for 2 days, filtered and concentrated in vacuo. The residue is purified by silica gel chromatography (gradient ethyl acetate in heptane, 20% to 90%) to give 3-(3,3-dimethyl-1-oxo-isochroman-4-yl)-3H- imidazole-4-carboxylic acid ethyl ester as oil; HRMS (ESI) m/z 315.1355 [(M+H)+: Calcd for $C_{17}H_{18}N_2O_4$: 315.1345]; $^1$H NMR (400 MHz, MeOD) of the HCl salt δ ppm 1.24 (s, 3 H), 1.43 (t, J=7.1 Hz, 3 H), 1.55 (s, 3 H), 4.46 (q, J=7.1 Hz, 2 H), 6.83 (s, 1 H), 7.53 (d, J=7.6 Hz, 1 H), 7.66-7.71 (m, 2 H), 7.78 (td, 1 H), 7.91 (s, 1 H), 8.26 (dd, J=7.8, 1.3 Hz, 1 H)

(b) (R)- and (S)-3-(3,3-Dimethyl-1-oxo-isochroman-4-yl)-3H-imidazole-4-carboxylic Acid Ethyl Ester Resolution of the enantiomers of the title compound is achieved by chiral HPLC using the ChiralPak AS-H column with a 4:1 hexanes-isopropanol mobile phase to give enantiomer A ($t_r$=10.5 min) and enantiomer B ($t_r$=12.4 min). The Following Compound can be Prepared in a Similar Fashion as Example 22:

(R)- and (S)-3-(3,3-Dimethyl-1-oxo-isochroman-4-yl)-3H-imidazole-4-carboxylic Acid Methyl Ester

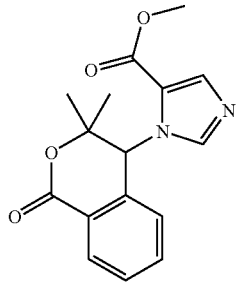

MS (ESI) m/z 301.0 (M+H); $^1$H NMR (400 MHz, MeOD) δ ppm 1.26 (s, 3 H), 1.58 (s, 3 H), 4.00 (s, 3 H), 6.81 (s, 1 H), 7.47 (s, 1 H), 7.54 (d, J=7.6 Hz, 1 H), 7.71 (td, J=7.8, 1.3 Hz, 1H), 7.79 (dd, J=7.6, 1.5 Hz, 1 H), 7.82 (d, J=1.0 Hz, 1 H), 8.28 (dd, J=7.7, 1.4 Hz, 1 H).

Resolution of the enantiomers of the title compound is achieved by chiral HPLC using the ChiralPak AS-H column with a 9:1 hexanes-isopropanol mobile phase to give enantiomer A ($t_r$=22.0 min) and enantiomer B ($t_r$=30.9 min).

Example 23

(a) 3-(3,3-Dimethyl-1-oxo-isochroman-4-yl)-3H-imidazole-4-carboxylic Acid

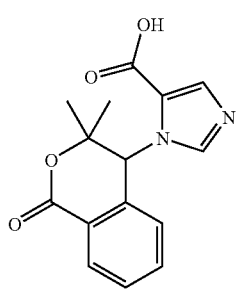

3-(3,3-Dimethyl-1-oxo-isochroman-4-yl)-3H-imidazole-4-carbonitrile (0.100 g, 0.374 mmol) (Example 20) is dissolved in a mixture of tetrahydrofuran (2 mL) and water (0.2 mL). Sulfuric acid (0.2 mL, 1.872 mmol) is added and the mixture is stirred at reflux for 16 h. Concentration in vacuo gave a residue which is purified by reverse phase HPLC to give 3-(3,3-dimethyl-1-oxo-isochroman-4-yl)-3H-imidazole-4-carboxylic acid; MS (ESI) m/z 287.0 (M+H)

(b) 3-(3,3-Dimethyl-1-oxo-isochroman-4-yl)-3H-imidazole-4-carboxylic Acid Isopropyl Ester

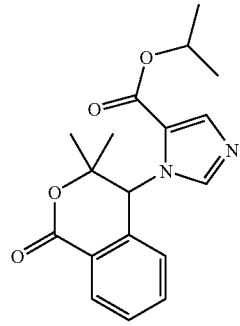

3-(3,3-Dimethyl-1-oxo-isochroman-4-yl)-3H-imidazole-4-carboxylic acid (0.075 g, 0.262 mmol) (Example 23) is dissolved in dichloromethane (2 mL). Catalytic amount of dimethylformamide (0.002 mL, 0.0262 mmol) is added to the reaction mixture and cooled to 0° C. Oxalyl chloride (0.016 mL, 0.655 mmol) is added and the cooling bath is removed. The mixture is stirred at room temperature for 2 h and concentrated in vacuo. The residue obtained is redissolved in dichloromethane, and isopropanol (10 mL) is added. The reaction mixture is stirred at room temperature for 1 h, whereupon the volatiles are removed in vacuo. Saturated aqueous sodium bicarbonate is added and extracted with dichloromethane. The combined organic phase is dried over $Na_2SO_4$ and concentrated in vacuo. The residue is purified by silica gel chromatography (hexane-ethyl acetate, 1:1) to give 3-(3,3-dimethyl-1-oxo-isochroman-4-yl)-3H-imidazole-4-carboxylic acid isopropyl ester; MS (ESI) m/z 329.0 (M+H); $^1$H NMR (400 MHz, MeOD) of the HCl salt δ ppm 1.34 (s, 3 H), 1.48 (d, J=5.9 Hz, 3 H), 1.49 (d, J=5.9 Hz, 3 H), 1.62 (s, 3 H), 5.42 (sept, J=5.9 Hz, 1 H), 7.02 (s, 1 H), 7.67 (d, J=7.6 Hz, 1 H), 7.75-7.81 (m, 1 H), 7.82-7.90 (m, 1 H), 8.33 (dd, J=7.8, 1.5 Hz, 1 H), 8.38 (d, J=1.3 Hz, 1 H), 8.76 (d, J=1.0 Hz, 1 H)

Example 24

3-(3,3-Dimethyl-1-oxo-isochroman-4-yl)-3H-imidazole-4-carboxylic Acid Phenylamide

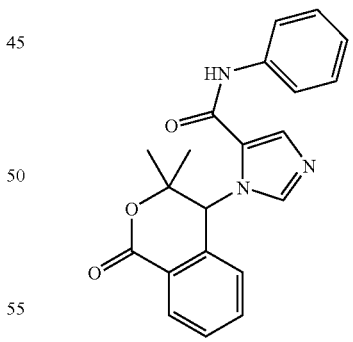

To a solution of 3-(3,3-dimethyl-1-oxo-isochroman-4-yl)-3H-imidazole-4-carboxylic acid (0.150 g, 0.524 mmol) (Example 23) dissolved in carbon tetrachloride (5 mL) is added thionyl chloride (0.386 mL, 5.24 mmol). The mixture is refluxed for 2 h. After concentration in vacuo, the residue obtained is redissolved in carbon tetrachloride, and aniline (0.240 mL, 2.62 mmol) is added. The reaction mixture is stirred at room temperature for 1 h. The mixture is washed with saturated aqueous sodium bicarbonate and extracted with dichloromethane twice. The combined organic phase is dried over $Na_2SO_4$ and concentrated in vacuo. The residue is purified by reverse phase HPLC to give 3-(3,3-dimethyl-1-oxo-isochroman-4-yl)-3H-imidazole-4-carboxylic acid benzyl amide; MS (ESI) m/z 362.0 (M+H); ¹H NMR (400 MHz, MeOD) δ ppm 1.31 (s, 3 H), 1.57 (s, 3 H), 6.96 (s, 1 H), 7.18-7.25 (m, 1 H), 7.36-7.48 (m, 3 H), 7.64 (d, J=7.6 Hz, 1 H), 7.68-7.78 (m, 3 H), 7.78-7.85 (m, 1 H), 7.88 (s, 1 H), 8.28 (dd, J=7.8, 1.3 Hz, 1 H).

Example 25

3-(3,3-Dimethyl-1-oxo-isochroman-4-yl)-3H-imidazole-4-carboxylic Acid Benzylamide

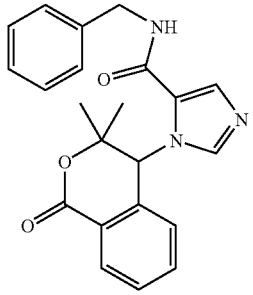

3-(3,3-Dimethyl-1-oxo-isochroman-4-yl)-3H-imidazole-4-carboxylic acid (0.100 g, 0.349 mmol) (Example 23) is dissolved in dichloromethane (2 mL). Catalytic amount of dimethylformamide (0.002 mL, 0.0262 mmol) is added to the reaction mixture and cooled to 0° C. Oxalyl chloride (0.076 mL, 0.874 mmol) is added and the cooling bath is removed. The mixture is stirred at room temperature for 2 h and then concentrated in vacuo. The residue obtained is redissolved in dichloromethane and benzylamine (0.114 mL, 1.04 mmol) is added. Reaction mixture is stirred at room temperature for 1 h. The mixture is washed with saturated aqueous sodium bicarbonate and extracted with dichloromethane. The combined organic phase is dried over Na₂SO₄ and concentrated in vacuo. The residue is purified by silica gel chromatography (dichlormethane-methanol, 19:1) to give 3-(3,3-dimethyl-1-oxo-isochroman-4-yl)-3H-imidazole-4-carboxylic acid benzylamide; MS (ESI) m/z 376.0 (M+H); ¹H NMR (400 MHz, MeOD) δ ppm 1.24 (s, 3 H), 1.53 (s, 3 H), 4.62 (s, 2 H), 6.98 (s, 1 H), 7.26-7.35 (m, 1 H), 7.35-7.46 (m, 5 H), 7.57 (d, J=7.6 Hz, 1 H), 7.64-7.73 (m, 2 H), 7.74-7.84 (m, 1 H), 8.26 (dd, J=7.8, 1.5 Hz, 1 H).

The Following Compounds can be Prepared in a Similar Fashion as Example 25:

3-(3,3-Dimethyl-1-oxo-isochroman-4-yl)-3H-imidazole-4-carboxylic acid (4-fluoro)-benzylamide

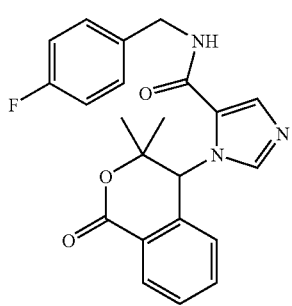

MS (ESI) m/z 394.3 (M+H); ¹H NMR (400 MHz, MeOD) δ ppm 1.23 (s, 3 H), 1.53 (s, 3 H), 4.59 (s, 2 H), 6.97 (s, 1 H), 7.07-7.19 (m, 2 H), 7.36 (s, 1 H), 7.40-7.48 (m, 2 H), 7.55 (d, J=7.6 Hz, 1 H), 7.65-7.73 (m, 1 H), 7.75-7.82 (m, 1 H), 8.26 (d, J=7.8 Hz, 1 H)

3(3,3-Dimethyl-1-oxo-isochroman-4-yl)-3H-imidazole-4-carboxylic Acid (2-fluoro-benzyl)-methyl-amide

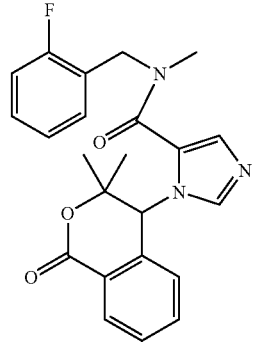

MS (ESI) m/z 408.1 (M+H); ¹H NMR (400 MHz, MeOD) δ ppm 1.25 (s, 3 H), 1.52 (s, 3 H), 3.24 (br. s, 3 H), 4.93 (br. s, 2 H), 6.26 (s, 1 H), 7.17-7.40 (m, 2 H), 7.37-7.53 (m, 4 H), 7.64-7.73 (m, 2 H), 7.80 (td, J=7.3, 1.3 Hz, 1 H), 8.26 (d, J=7.8 Hz, 1 H).

3-(3,3-Dimethyl-1-oxo-isochroman-4-yl)-3H-imidazole-4-carboxylic acid (4-fluoro-benzyl)-methyl-amide

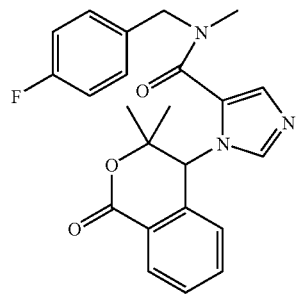

MS (ESI) m/z 408.1 (M+H); ¹H NMR (400 MHz, MeOD) δ ppm 1.24 (s, 3 H), 1.53 (s, 3 H), 3.23 (br. s, 3 H), 4.82 (br. s, 2 H), 6.30 (s, 1 H), 7.18 (t, J=8.7 Hz, 2 H), 7.38-7.45 (m, 4 H), 7.66 (br. d, J=7.6 Hz, 1 H) 7.70 (td, J=7.6, 1.3 Hz, 1 H), 7.81 (td, J=7.6, 1.4 Hz, 1 H), 8.26 (d, J=7.6, 1.3 Hz, 1 H).

3-(3,3-Dimethyl-1-oxo-isochroman-4-yl)-3H-imidazole-4-carboxylic acid (2-hydroxy-ethyl)-amide

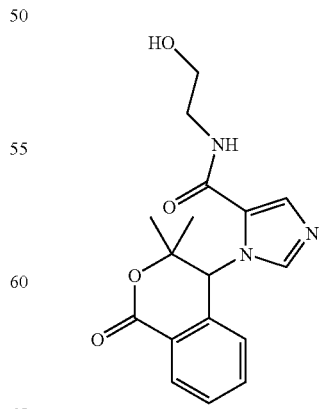

HRMS (ESI) m/z 328.1299 [(M+H)⁺ Calcd for C₁₇H₁₈N₃O₄: 328.1297]; ¹H NMR (400 MHz, MeOD) δ ppm 1.26 (s, 3 H), 1.55 (s, 3 H), 3.47-3.62 (m, 2 H), 3.71-3.83 (m, 2 H), 6.96 (s, 1 H), 7.35 (s, 1 H), 7.58 (d, J=7.6 Hz, 1 H), 7.65-7.73 (m, 2 H), 7.79 (td, J=7.6, 1.3 Hz, 1H), 8.26 (dd, J=7.8, 1.3 Hz, 1 H)

(R)- and (S)-3-(3,3-Dimethyl-1-oxo-isochroman-4-yl)-3H-imidazole-4-carboxylic Acid Phenyl Ester

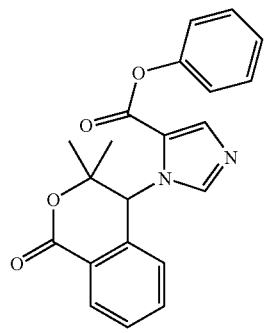

MS (ESI) m/z 362.9 (M+H); $^1$H NMR (400 MHz, MeOD) δ ppm 1.32 (s, 3 H), 1.57 (s, 3 H), 6.75 (s, 1 H), 7.23-7.42 (m, 3 H), 7.47-7.55 (m, 2 H), 7.56-7.62 (m, 2 H), 7.72 (td, J=7.6, 1.3 Hz, 1 H), 7.82 (td, J=7.6, 1.3 Hz, 1 H), 8.09 (d, J=1.0 Hz, 1 H), 8.29 (dd, J=7.7, 1.4 Hz, 1 H).

Resolution of the enantiomers of the title compound is achieved by chiral HPLC using the ChiralPak IA column with a 7:3 acetonitrile-ethanol mobile phase to give enantiomer A ($t_r$=4.2 min) and enantiomer B ($t_r$=6.3 min).

Example 26

3,3-Dimethyl-4-[5-(3-methyl-[1,2,4]oxadiazol-5-yl)-imidazol-1-yl]-isochroman-1-one

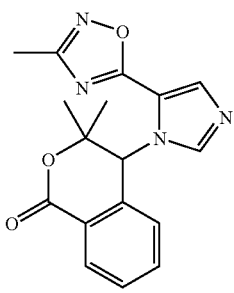

3-(3,3-Dimethyl-1-oxo-isochroman-4-yl)-3H-imidazole-4-carboxylic acid (0.538 g, 1.88 mmol) (Example 23) is dissolved in dichloromethane (4 mL) and cooled to 0° C. Oxalyl chloride (0.41 mL, 4.702 mmol) is added and the cooling bath is removed. The mixture is stirred at room temperature for 3 h. The reaction mixture is concentrated in vacuo. The residue obtained is redissolved in chloroform and N-hydroxyacetamidine (0.181 g, 2.44 mmol) is added. The reaction mixture is stirred at reflux for 72 h. The mixture is cooled to room temperature, washed with saturated solution of sodium bicarbonate and is extracted with dichloromethane. The organic phase is dried over Na$_2$SO$_4$ and concentrated in vacuo. The residue is purified by silica gel chromatography (hexane-ethyl acetate, 3:7) to give dimethyl-4-[5-(3-methyl-[1,2,4] oxadiazol-5-yl)-imidazol-1-yl]-isochroman-1-one as a white solid; MS (ESI) m/z 325.0 (M+H); $^1$H NMR (400 MHz, MeOD) δ ppm 1.26 (s, 3 H), 1.61 (s, 3 H), 2.55 (s, 3 H), 6.94 (s, 1 H), 7.56 (d, J=7.1 Hz, 1 H), 7.63 (s, 1 H), 7.72 (td, J=7.6, 1.3 Hz, 1 H), 7.80 (td, J=7.6, 1.3 Hz, 1 H), 8.01 (s, 1 H), 8.30 (dd, J=7.8, 1.3 Hz, 1 H).

Example 27

(a) (1-Trityl-1H-imidazol-4-yl)acetic acid (CAS # 168632-03-9)

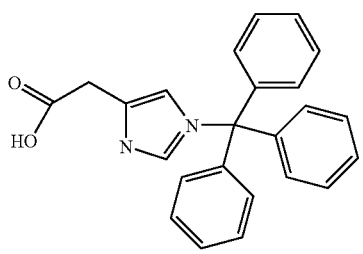

Trityl chloride (51 g, 0.18 mol) is added to a suspension of (1H-imidazol-4-yl)acetic acid hydrochloride (25 g, 0.15 mol) in pyridine (500 mL, 0.3 M). This is stirred at room temperature for 16 h, at the end of which MeOH (150 mL) is added. This solution is stirred at room temperature for 1 h. Solvents are evaporated and the residue is taken up in CH$_2$Cl$_2$ and washed twice with 1 M aqueous citric acid solution and brine. The organic phase is dried over anhydrous Na$_2$SO$_4$ and evaporated to give a sticky residue which when taken up in diethyl ether and evaporated gives the product as a white solid that is used without further purification; MS (ESI) m/z 368.9 (M+H) (Procedure adapted from *J. Org. Chem.* 1993, 58, 4606, also prepared in WO2003013526).

(b) 2-(1-Trityl-1H-imidazol-4-yl)ethanol (CAS# 127607-62-9)

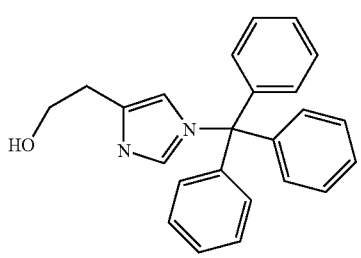

A solution of (1-trityl-1H-imidazol-4-yl)-acetic acid (6.27 g, 17.03 mmol) in THF (100 mL) is cooled to 0° C. Lithium aluminumhydride (1M solution in THF, 42.6 mL, 42.6 mmol) is added to it dropwise. The reaction mixture is stirred at room temperature for 1 h. It is quenched with saturated aqueous sodium bicarbonate and extracted with ethyl acetate twice. The combined organic phase is dried over Na$_2$SO$_4$ and concentrated in vacuo to give (1-trityl-1H-imidazol-4-yl)-acetic acid, which is used in the next step without further purification; $^1$H NMR (400 MHz, CHLOROFORM-D) δ ppm 2.76 (t, J=5.6 Hz, 2 H), 3.89 (t, J=5.7 Hz, 2 H), 6.61 (d, J=1.5 Hz, 1 H), 7.32-7.38 (m, 16 H).

(c) 4-[2-(tert-Butyldimethylsilanyloxy)-ethyl]-1-trityl-1H-imidazole

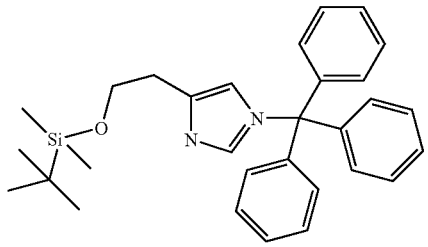

To a solution of 2-(1-trityl-1H-imidazol-4-yl)-ethanol (5.21 g, 14.7 mmol) in DMF (20 mL) is added tert-butylchlorodimethylsilane (2.44 g, 16.1 mmol), dimethylaminopyridine (0.179 g, 1.47 mmol) and imidazole (3.00 g, 44.1 mmol). The reaction mixture is stirred for 2 h at room temperature. It is then diluted with ethyl acetate and washed with water thrice. The organic phase is dried over Na$_2$SO$_4$ and concentrated in vacuo. The residue is purified by silica gel chromatography (hexane-ethanol, 7:3) to give 4-[2-(tert-butyl-dimethyl-silanyloxy)-ethyl]-1-trityl-1H-imidazole product, which is used in the next step without further purification; MS (ESI) m/z 469.3 (M+H)

(d) 2-{5-[2-(tert-Butyldimethylsilanyloxy)-ethyl]-imidazol-1-ylmethyl}-benzonitrile

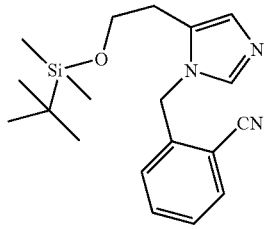

To a solution of 4-[2-(tert-butyldimethylsilanyloxy)-ethyl]-1-trityl-1H-imidazole (2.10 g, 4.48 mmol) in acetonitrile (20 mL) is added 2-bromomethylbenzonitrile (0.967 g, 4.93 mmol). The reaction mixture is stirred at 60° C. for 16 h. It is then cooled to room temperature and diethylamine (5 mL, 44.8 mmol) is added. The reaction mixture is stirred at 60° C. for 30 min. It is then cooled to room temperature and the solvents are removed in vacuo. Methanol (25 mL) is added and stirring is continued for 1 h at room temperature. Methanol is removed by concentration in vacuo. The residue is dissolved in ethyl acetate and washed with water twice. The combined organic phase is dried over Na$_2$SO$_4$ and concentrated in vacuo. The residue is purified by silica gel chromatography (dichloromethane-methanol, 19:1) to give 2-{5-[2-(tert-butyldimethylsilanyloxy)-ethyl]-imidazol-1-ylmethyl}-benzonitrile; MS (ESI) m/z 342 (M+H)

(e) 2-(1-{5-[2-tert-Butyldimethylsilanyloxy)-ethyl]-imidazol-1-yl}-2-hydroxy-2-methyl-propyl)-benzonitrile

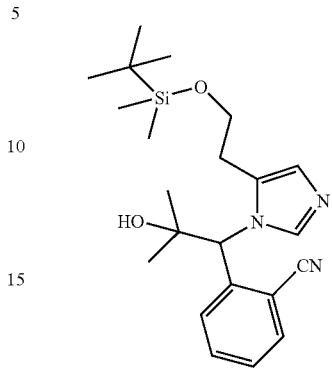

2-{5-[2-(tert-Butyldimethylsilanyloxy)-ethyl]-imidazol-1-ylmethyl}-benzonitrile (1.14 g, 3.34 mmol) is dissolved in THF (20 mL) and cooled to −78° C. LHMDS (1M in THF, 5 mL, 5 mmol) is added dropwise. Ten min after the end of addition, acetone (0.295 g, 5.01 mmol) is added. The reaction mixture is stirred at −78° C. for 40 min. It is then quenched with saturated aqueous sodium bicarbonate (10 mL). The mixture is allowed to warm to room temperature, then poured into water. After extraction with ethyl acetate the organic phase is dried over Na$_2$SO$_4$ and concentrated in vacuo to give 2-(1-{5-[2-(tert-butyldimethylsilanyloxy)-ethyl]-imidazol-1-yl}-2-hydroxy-2-methyl-propyl)-benzonitrile; MS (ESI) m/z 400.3 (M+H)

(f) 4-[5-(2-Hydroxyethyl)-imidazol-1-yl]-3,3-dimethyl-isochroman-1-one

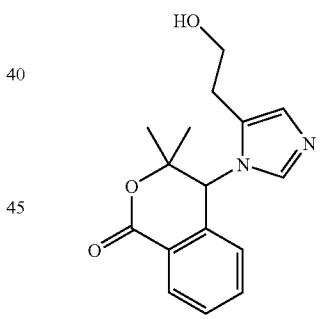

2-(1-{5-[2-(tert-Butyldimethylsilanyloxy)-ethyl]-imidazol-1-yl}-2-hydroxy-2-methyl-propyl)-benzonitrile (1.5 g, 3.75 mmol) is dissolved in THF (15 mL). Concentrated sulfuric acid (0.80 mL, 15.03 mmol) and water (0.80 mL) are added and the mixture is stirred at reflux for 24 h. After cooling down, the mixture is basified to pH 10 using 10% aqueous sodium hydroxide and is then extracted with ethyl acetate twice. The combined organic phase is dried over Na$_2$SO$_4$ and concentration in vacuo. The residue obtained is purified by silica gel chromatography (dichloromethane-methanol, 9:1) to give 4-[5-(2-hydroxy-ethyl)-imidazol-1-yl]-3,3-dimethyl-isochroman-1-one; HRMS (ESI) m/z 287.1403; [(M+H)$^+$ Calcd for C$_{16}$H$_{19}$N$_2$O$_3$: 287.1396]; $^1$H NMR (400 MHz, MeOD) δ ppm 1.26 (s, 3 H), 1.56 (s, 3 H), 3.06 (br. s, 2 H), 3.75-4.18 (m, 2 H), 5.74 (br. s, 1 H), 6.92 (br. s, 1 H), 7.15 (d, J=1.3 Hz, 1 H), 7.57 (d, J=7.3 Hz, 1 H), 7.67 (t, J=7.3 Hz, 1 H), 7.78 (t, J=7.3 Hz, 1 H), 8.24 (d, J=7.3 Hz, 1 H)

(g) (R)- and (S)-4-[5-(2-Hydroxyethyl)-imidazol-1-yl]-3,3-dimethyl-isochroman-1-one Resolution of the enantiomers of the title compound is achieved by chiral HPLC using the ChiralPak IA column with a 9:1 heptane-ethanol mobile phase to give enantiomer A ($t_r$=35.5 min) and enantiomer B ($t_r$=42.7 min).

Example 28

4-[5-(2-Fluoro-ethyl)-imidazol-1-yl]-3,3-dimethyl-isochroman-1-one

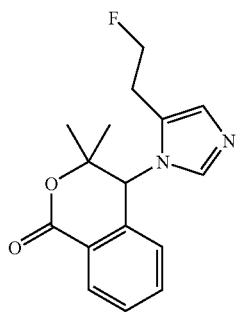

To a partial suspension of 4-[5-(2-hydroxy-ethyl)-imidazol-1-yl]-3,3-dimethyl-isochroman-1-one (0.180 g, 0.616 mmol) (example 27f) in dichloromethane (10 mL) at 0° C. under nitrogen is added DAST (0.314 g, 1.848 mmol) dropwise. After 30 min, the mixture is diluted with dichloromethane and washed twice with saturated aqueous sodium bicarbonate, water and brine. The combined aqueous phase is back-extracted once with dichloromethane. The combined organic phase is dried over magnesium sulfate and filtered through a cotton plug. The residue is purified by silica gel flash chromatography (elution with dichloromethane-methanol, 99:1 to 49:1) to afford 4-[5-(2-fluoro-ethyl)-imidazol-1-yl]-3,3-dimethyl-isochroman-1-one as an oil. The material is converted to the HCl salt and triturated with methanol, to give a crystalline solid; MS (ESI) m/z 289.0 (M+H); $^1$H NMR (400 MHz, MeOD) δ ppm 1.27 (s, 3 H), 1.59 (s, 3 H), 4.69-4.95 (m, 4 H), 5.73 (br. S., 1 H), 7.16 (s, 1 H), 7.53 (d, J=7.6 Hz, 1 H), 7.63 (br. S., 1 H), 7.71 (td, J=7.6, 1.1 Hz, 1 H), 7.81 (td, J=7.6, 1.3 Hz, 1H), 8.27 (dd, J=7.8, 1.3 Hz, 1 H).

Example 29

(a) 2-Imidazol-1-ylmethyl-benzonitrile (CAS# 143426-58-8)

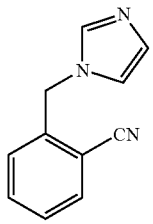

To a solution of imidazole (1.0 g, 14.6 mmol) in DMF (10 mL) is added sodium hydride (60% wt. in mineral oil, 0.887 g, 22.17 mmol) at room temperature. The mixture is stirred for 30 min, whereupon 2-cyanobenzyl bromide (2.87 g, 14.6 mmol) is added. After an additional 30 min, water is added and the mixture is extracted with ethyl acetate. The aqueous phase is poured into aqueous sodium bicarbonate and extracted with dichloromethane. The combined organic phase is dried over sodium sulfate, filtered and concentrated in vacuo to give a residue which is purified by silica gel chromatography (dichloromethane-methanol, 19:1) to give 2-imidazol-1-ylmethyl-benzonitrile; MS (ESI) m/z 184.3 (M+H).

(b) 2-(2-Hydroxy-1-imidazol-1-yl-2-methyl-propyl)-benzonitrile

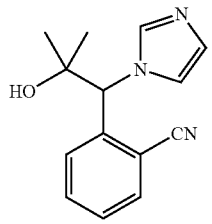

2-Imidazol-1-ylmethyl-benzonitrile (1.0 g, 5.49 mmol) is dissolved in THF (10 mL) and cooled to −75° C. LHMDS (1M in THF, 8.24 mL, 8.24 mmol) is added dropwise. Ten min after the end of addition, acetone (0.48 g, 8.24 mmol) is added. Thirty min after the end of addition, saturated aqueous sodium bicarbonate (10 mL) is added and the mixture is allowed to warm to r.t., then poured into water. After extraction with ethyl acetate the organic phase is dried over $Na_2SO_4$ and concentrated in vacuo. The residue is used in the next step without further purification; MS (ESI) m/z 242.1 (M+H).

(c) 4-(Imidazol-1-yl)-3,3-dimethyl-isochroman-1-one

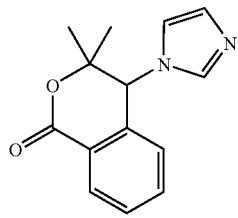

Crude 2-(2-hydroxy-1-imidazol-1-yl-2-methyl-propyl)-benzonitrile (1.75 g) is dissolved in dioxane (15 mL) and water (15 mL). Sulfuric acid (1.5 mL, 29.0 mmol) is added and the mixture is stirred at reflux for 2 h. After cooling down, the pH is adjusted with solid sodium bicarbonate. The mixture is extracted with ethyl acetate and the combined organic phase is washed with water, dried over $Na_2SO_4$ and concentrated in vacuo. The residue is purified by silica gel chromatography (dichloromethane-methanol, 19:1) to give 4-(imidazol-1-yl)-3,3-dimethyl-isochroman-1-one; MS (ESI) m/z 242.9 (M+H); $^1$H NMR (400 MHz, MeOD) δ ppm. 1.30 (s, 3 H), 1.53 (s, 3 H), 5.76 (s, 1 H), 6.98 (s, 1 H), 7.09 (s, 1 H), 7.52 (d, J=7.6 Hz, 1 H), 7.64-7.73 (m, 1 H), 7.76-7.85 (m, 1 H), 7.89 (s, 1 H), 8.25 (dd, J=7.7, 1.4 Hz, 1 H).

(d) (R)- and (S)-4-(Imidazol-1-yl)-3,3-dimethyl-isochroman-1-one

Resolution of the enantiomers of the title compound is achieved by chiral HPLC using the ChiralPak AS-H column with a 9:1 heptane-ethanol mobile phase to give enantiomer A ($t_r$=10.1 min) and enantiomer B ($t_r$=16.6 min).

The Following Compounds can be Prepared in a Similar Fashion as Example 29:

(R)- and (S)-6-Fluoro-4-imidazol-1-yl-3,3-dimethyl-isochroman-1-one

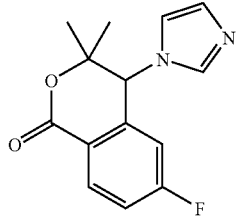

HRMS (ESI) m/z 261.1044 [(M+H)$^+$ Calcd for C$_{14}$H$_{13}$FN$_2$O$_2$: 261.1039]; $^1$H NMR (400 MHz, MeOD) δ ppm 1.24 (s, 3 H), 1.49 (s, 3 H), 5.70 (s, 1 H), 6.90 (s, 1 H), 7.01 (s, 1 H), 7.24 (dd, J=8.6, 2.5 Hz, 1 H), 7.38 (td, J=8.6, 2.5 Hz, 1 H), 7.74 (s, 1 H), 8.26 (dd, J=8.6, 5.6 Hz, 1 H).

Resolution of the enantiomers of the title compound is achieved by chiral HPLC using the ChiralPak IA column with a 85:15 heptane-reagent alcohol mobile phase to give enantiomer A (t$_r$=21.4 min) and enantiomer B (t$_r$=34.6 min).

(R)- and (S)-7-Chloro-4-imidazol-1-yl-3,3-dimethyl-isochroman-1-one

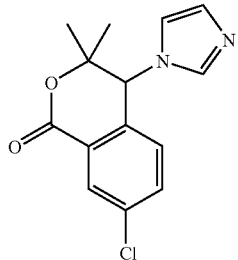

(ESI) m/z 277, 279 (M+H); $^1$H NMR (400 MHz, MeOD) δ ppm 1.28 (s, 3 H), 1.52 (s, 3 H), 5.75 (s, 1 H), 6.93 (s, 1 H), 7.04 (s, 1 H), 7.51 (d, J=8.3 Hz, 1 H), 7.74-7.82 (m, 2 H), 8.21 (d, J=2.0 Hz, 1 H).

Resolution of the enantiomers of the title compound is achieved by chiral HPLC using the Chiralcel OD column with a 9:1 hexanes-ethanol mobile phase to give enantiomer A (t$_r$=14.6 min) and enantiomer B (t$_r$=18.9 min).

(R)- and (S)-7-Fluoro-4-imidazol-1-yl-3,3-dimethyl-isochroman-1-one

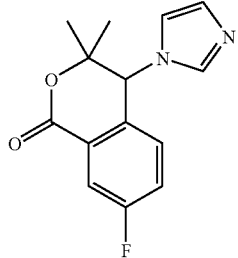

(ESI) m/z 261.3 (M+H); $^1$H NMR (400 MHz, MeOD) δ ppm 1.28 (s, 3 H), 1.53 (s, 3 H), 5.74 (s, 1 H), 6.91 (s, 1 H), 7.03 (s, 1 H), 7.43-7.61 (m, 2 H), 7.77 (s, 1 H), 7.93 (dd, J=8.3, 2.3 Hz, 1 H).

Resolution of the enantiomers of the title compound is achieved by chiral HPLC using the Chiralcel OD column with a 9:1 hexanes-ethanol mobile phase to give enantiomer A (t$_r$=13.6 min) and enantiomer B (t$_r$=17.4 min).

(R)- and (S)-6-Methoxy-4-imidazo-1-yl-3,3-dimethyl-isochroman-1-one

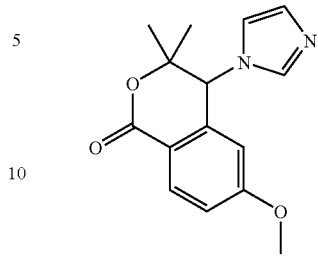

(ESI) m/z 273.3 (M+H); $^1$H NMR (400 MHz, MeOD) δ ppm 1.26 (s, 3 H), 1.52 (s, 3 H), 3.91 (s, 3 H), 5.63 (s, 1 H), 6.92 (br. s, 1 H), 7.00 (d, J=2.5 Hz 1 H), 7.02 (br. s, 1 H), 7.19 (dd, J=8.8, 2.5 Hz, 1 H), 7.75 (br. s, 1 H), 8.17 (d, J=8.8 Hz, 1 H)

Resolution of the enantiomers of the title compound is achieved by chiral HPLC using the Chiralcel OD column with a 4:1 hexanes-isopropanol mobile phase to give enantiomer A (t$_r$=9.0 min) and enantiomer B (t$_r$=10.0 min).

(R)- and (S)-6,8-Dichloro-4-imidazol-1-yl-3,3-dimethyl-isochroman-1 one

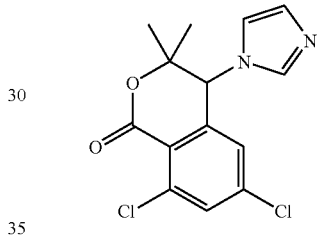

HRMS (ESI) m/z 311.0353 [(M+H)$^+$ Calcd for C$_{14}$H$_{12}$Cl$_2$N$_2$O$_2$: 311.0354]; $^1$H NMR (400 MHz, MeOD) δ ppm 1.24 (s, 3 H), 1.47 (s, 3 H), 5.72 (s, 1 H), 6.95 (t, J=1.4 Hz, 1 H), 7.04 (s, 1H), 7.48 (d, J=2.0 Hz, 1 H), 7.77 (s, 1 H), 7.79 (d, J=2.0 Hz, 1 H).

Resolution of the enantiomers of the title compound is achieved by chiral HPLC using the ChiralPak AS-H column with a 85:15 heptane-reagent alcohol mobile phase to give enantiomer A (t$_r$=6.5 min) and enantiomer B (t$_r$=8.2 min).

(R)- and (S)-6-Trifluoromethyl-4-imidazol-1-yl-3,3-dimethyl-isochroman-1 one

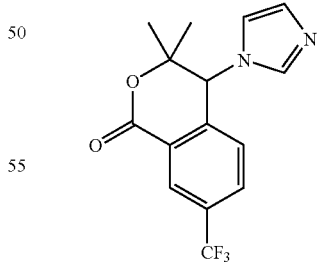

MS (ESI) m/z 311.0 (M+H); $^1$H NMR (400 MHz, CDCl$_3$) δ ppm 1.37 (s, 3 H), 1.55 (s, 3 H), 5.47 (s, 1 H), 6.81 (t, J=1.3 Hz, 1 H), 7.15 (s, 1 H), 7.47 (d, J=8.0 Hz, 1 H), 7.87-7.96 (m, 2H), 8.54 (d, J=1.3 Hz, 1 H).

Resolution of the enantiomers of the title compound is achieved by chiral HPLC using the ChiralPak AS-H column with a 19:1 heptane-reagent alcohol mobile phase to give enantiomer A (t$_r$=9.8 min) and enantiomer B (t$_r$=13.7 min).

(R)- and (S)-[4-(imidazol-1-yl)-7-fluoro-isochroman-1-one]-3-spirocyclobutane

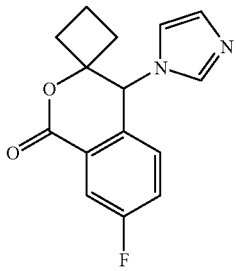

HRMS (ESI) m/z 273.1046 [(M+H)$^+$ Calcd for C$_{15}$H$_{14}$FN$_2$O$_2$: 273.1039]; $^1$H NMR (400 MHz, MeOD) of the HCl salt δ ppm 1.93-2.43 (m, 6 H), 6.26 (s, 1 H), 7.51-7.66 (m, 3 H), 7.79 (dd, J=8.5, 4.9 Hz, 1 H), 7.93 (dd, J=8.5, 2.7 Hz, 1 H), 9.11 (s, 1 H)

Resolution of the enantiomers of the title compound is achieved by chiral HPLC using the ChiralPak AS-H column with a 19:1 heptane-ethanol mobile phase to give enantiomer A (t$_r$=15.4 min) and enantiomer B (t$_r$=21.7 min).

(R)- and (S)-6-Fluoro-4-imidazol-1-yl-3,3-diethyl-isochroman-1-one

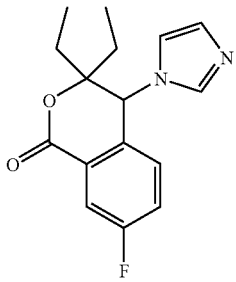

HRMS (ESI) m/z 289.1346 [(M+H)$^+$ Calcd for C$_{16}$H$_{16}$FN$_2$O$_2$: 289.1352]; $^1$H NMR (400 MHz, MeOD) of the HCl salt δ ppm 0.94 (t, J=7.3 Hz, 3 H), 0.96 (t, J=7.3 Hz, 3 H), 1.40-1.57 (m, 2 H), 1.68-1.85 (m, 2 H), 5.78 (s, 1 H), 6.88 (s, 1 H), 6.97 (s, 1 H), 7.49 (td, J=8.7, 2.6 Hz, 1 H), 7.55 (dd, J=8.1, 5.0 Hz, 1 H), 7.76 (s, 1 H), 7.87 (dd, J=8.5, 2.7 Hz, 1 H)

Resolution of the enantiomers of the title compound is achieved by chiral HPLC using the ChiralPak AS-H column with a 19:1 heptane-reagent alcohol mobile phase to give enantiomer A (t$_r$=22.5 min) and enantiomer B (t$_r$=27.9 min).

Example 30

(3R,4R)-, (3S,4S)-, (3R,4S)- and (3S,4R)-,4-Imidazol-1-yl-3-phenyl-isochroman-1-one

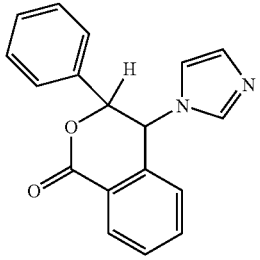

2-Imidazol-1-ylmethyl-benzonitrile (0.84 g, 4.36 mmol) (Example 29a) is dissolved in THF (40 mL) and cooled to −78° C. LHMDS (1.0M in THF, 15.2 mL, 15.2 mmol) is added, followed after 10 min with benzaldehyde (2.10 g, 19.60 mmol). After 1 min, the reaction is quenched with 1M aqueous sodium hydrogen sulfate. The pH is adjusted to 12 with 4M aqueous sodium hydroxide and extracted with ethyl acetate. The organic phase is dried over MgSO$_4$ and concentrated in vacuo to give a residue, which is purified by silica gel flash chromatography (dichloromathe-methanol, 1:0 to 23:1 gradient) to give after concentration of the fractions a yellow residue (1.40 g), which is redissolved in dioxane (40 mL). 10M aqueous H$_2$SO$_4$ (2.2 mL, 22 mmol) is added. The mixture is heated to 90° C. After overnight stirring, the mixture is diluted with ethyl acetate and washed with saturated aqueous bicarbonate and brine. The organic phase is dried over MgSO$_4$ and concentrated in vacuo to give a gummy residue. Purification and resolution of the four isomers of the title compound is achieved by chiral HPLC using the ChiralPak OD-RH column with a 7:3 heptane-ethanol mobile phase to give the cis diastereomer as enantiomer A (t$_r$=14.0 min) and enantiomer B (t$_r$=16.7 min) and the trans diastereomer as enantiomer C (t$_r$=23.2 min) and enantiomer D (t$_r$=43.2 min).

cis diastereomer: MS (ESI) m/z 291.0 (M+H); $^1$H NMR (400 MHz, DMSO-d$_6$) δ ppm 6.06 (d, J=2.9 Hz, 1 H), 6.29 (d, J=2.9 Hz, 1 H), 6.59 (s, 1 H), 6.72 (s, 1 H), 7.09 (s, 1 H), 7.16-7.22 (m, 2 H), 7.28-7.34 (m, 3 H), 7.60 (d, J=7.1 Hz, 1 H), 7.71 (td, J=7.7, 1.3 Hz, 1 H), 7.81 (td, J=7.6, 1.5 Hz, 1 H), 8.19 (dd, J=7.8, 1.3 Hz, 1 H), trans diastereomer: MS (ESI) m/z 291.0 (M+H); $^1$H NMR (400 MHz, DMSO-d$_6$) δ ppm 6.19 (d, J=10.5 Hz, 1 H), 6.36 (d, J=10.5 Hz, 1 H), 6.70 (d, J=7.8 Hz, 1 H), 6.91 (s, 1 H), 7.19 (t, J=1.3 Hz, 1 H), 7.30-7.36 (m, 3 H), 7.37-7.44 (m, 2 H), 7.56-7.64 (m, 2 H), 7.72 (td, J=7.6, 1.4 Hz, 1 H), 8.10 (dd, J=7.7, 1.1 Hz, 1 H).

Example 31

(a)
N,N-Diethyl-3,4-difluoro-2-hydroxymethyl-benzamide

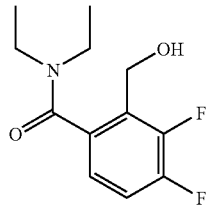

A flask is charged with 3,4-difluorobenzoic acid (2.40 g, 14.88 mmol) and dichloromethane (50 mL) is added. Upon complete dissolution, the mixture is cooled to 0° C. and DMF (0.022 g, 0.298 mmol) and oxalyl chloride (3.85 g, 29.75 mmol) are added. The cooling bath is removed. After 2 h, the mixture is concentrated, taken up in dichloromethane (50 mL) and diethylamine (5.50 g, 74.38 mmol) is added. After 30 min, dichloromethane (500 mL) is added and the mixture is washed with 1M aqueous HCl, saturated aqueous sodium bicarbonate and brine. The organic phase is dried over magnesium sulfate and concentrated in vacuo to afford N,N-diethyl-3,4-difluorobenzamide as a brown oil, which is redissolved in anhydrous THF (60 mL). A 2 neck-flask is charged with paraformaldehyde (2.40 g, 76.22 mmol) and connected via a small length of tubing to another two-neck flask fitted with a pipette using an appropriate adapter. The second flask is charged with THF (60 mL) and cooled to −78° C. The paraformaldehyde is cracked with a heatgun and bubbled into the cold THF through the pipette. A clear solution is formed. To the solution of N,N-diethyl-3,4-difluorobenzamide in THF, is added TMEDA (2.98 g, 25.41 mmol) and the flask is cooled to −78° C. sec-BuLi (1.4M in cyclohexane, 18.1 mL, 25.4 mmol) is added and after 30 min, the cold solution of formaldehyde is added via cannula. After 2 h, the cooling bath is removed. Upon reaching room temperature, the reaction is quenched with 1M aqueous sodium bisulfate. After dilution with ethyl acetate, the organic phase is washed with saturated aqueous sodium bicarbonate and brine. The organic phase is dried over magnesium sulfate and concentrated in vacuo. The residue is purified by silica gel flash chromatography (ethyl acetate-heptane, 3:7 to 2:3 to 1:1) to yield N,N-diethyl-3,4-difluoro-2-hydroxymethyl-benzamide as an orange oil; $^1$H NMR (400 MHz, CHLOROFORM-d) δ ppm 1.12 (t, J=7.1 Hz, 3 H), 1.28 (t, J=7.1 Hz, 3 H), 3.26 (q, J=7.1 Hz, 2 H), 3.58 (q, J=7.1 Hz, 2H), 4.62 (br. s., 2 H), 7.00 (ddd, J=8.4, 4.6, 1.6 Hz, 1 H), 7.09-7.19 (m, 1 H).

(b) N,N-Diethyl-3,4-difluoro-2-imidazol-1-ylmethyl-benzamide

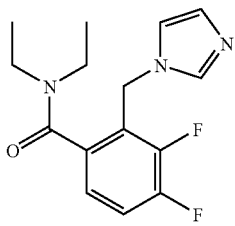

A flask is charged with polymer-supported triphenylphosphine (1.48 mmol/g, 6.87 g, 10.17 mmol) and dichloromethane (70 mL). Bromine (1.58 g, 9.77 mmol) is added at r.t., followed with N,N-diethyl-3,4-difluoro-2-hydroxymethyl-benzamide (1.100 g, 4.070 mmol) in dichloromethane (15 mL). After 5 min, the mixture is filtered and the resin is washed several times with dichloromethane. The resulting filtrate is concentrated in vacuo to yield an oil. Imidazole (2.80 g, 40.70 mmol) is added, followed with acetonitrile (30 mL) and the mixture is heated to 70° C. After 5 min at 70° C., the mixture is allowed to cool down, diluted with ethyl acetate and extracted three times with 1M aqueous HCl. The combined aqueous phase is washed once with dichloromethane. The aqueous phase is then cooled to 0° C. and the pH is adjusted to 12 with cold 4M aqueous NaOH. The aqueous phase is then extracted with dichloromethane. The combined extraction fractions are dried over MgSO$_4$ and filtered. The sample is concentrated in vacuo, taken up in ethyl acetate and washed with water (three times), and brine. The organic phase is dried over MgSO$_4$, filtered and concentrated in vacuo to give N,N-diethyl-3,4-difluoro-2-imidazol-1-ylmethyl-benzamide as a yellow oil; $^1$H NMR (400 MHz, CHLOROFORM-d) δ ppm 0.95 (t, J=7.1 Hz, 3 H), 1.26 (t, J=7.1 Hz, 3 H), 2.82 (q, J=7.1 Hz, 2 H), 3.52 (q, J=7.1 Hz, 2 H), 5.25 (br. s., 2 H), 6.96 (s, 1 H), 6.98-7.03 (m, 1 H), 7.01 (s, 1 H), 7.16-7.25 (m, 1 H), 7.51 (s, 1 H).

(c) 5,6-Difluoro-4-imidazol-1-yl-3,3-dimethyl-isochroman-1-one

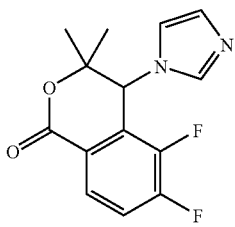

N,N-Diethyl-3,4-difluoro-2-imidazol-1-ylmethyl-benzamide (0.832 g, 2.695 mmol) is dissolved in THF (15 mL) and cooled to −78° C. LHMDS (1.0M in THF, 4.0 mL, 4.0 mmol) is added over 5 min, resulting in a dark brown solution. After another 10 min, acetone (0.79 g, 13.47 mmol) is added. After 30 min, the mixture is quenched with a pH 7 aqueous buffer and extracted twice with ethyl acetate. The combined organic phase is dried over magnesium sulfate and concentrated in vacuo to give a brown residue, which is redissolved in dioxane (25 mL). 1M aqueous KOH (13.5 mL, 13.5 mmol) is added. The solution is heated to 65° C. After 3 h, the mixture is cooled with a water bath, and acidified to pH=1 with conc. HCl. The mixture is heated to 65° C. After 1 h, the mixture is diluted with ethyl acetate and washed with saturated aqueous sodium bicarbonate, water and brine, dried over magnesium sulfate and filtered through a cotton plug. Concentration in vacuo gives a residue which is purified by silica gel flash chromatography (methylene chloride-methanol, 49:1 to 97:3) to give 5,6-difluoro-4-imidazol-1-yl-3,3-dimethyl-isochroman-1-one as an oil, which is converted to its HCl salt to give a solid; MS (ESI) m/z 279.1 (M+H); $^1$H NMR (400 MHz, MeOD) of the HCl salt, δ ppm 1.34 (s, 3 H), 1.61 (s, 3 H), 6.29 (s, 1 H), 7.46 (br. s., 1 H), 7.53 (br. s., 1 H), 7.66-7.75 (m, 1 H), 8.20 (ddd, J=8.8, 4.6, 1.6 Hz, 1 H), 8.79 (br. s., 1 H).

(d) (R)- and (S)-5,6-Difluoro-4-imidazol-1-yl-3,3-dimethyl-isochroman-1-one

Resolution of the enantiomers of the title compound is achieved by chiral HPLC using the ChiralPak IA column with a 4:1 heptane-ethanol mobile phase to give enantiomer A (t$_r$=13.1 min) and enantiomer B (t$_r$=25.1 min).

Example 32

(a) 2-Cyclopropyl-3,3-dimethyl-1 oxo-1,2,3,4-tetrahydro-isoquinoline-4-carboxylic Acid

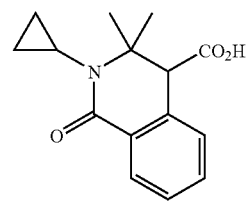

To type-I neutral alumina (16 g) is added cyclopropylamine (4.2 mL, 60 mmol) followed by dichloromethane (10 mL). The resulting slurry is cooled to 0° C. and acetone (6 mL, 82 mmol) is added slowly. The slurry is brought to room temperature and permitted to stir for 9 h, at which time the reaction mixture is filtered through a fritted funnel. The alumina cake is washed with chloroform (150 mL) and homophthalic anhydride (10.0 g, 62 mmol) is added to the combined filtrate. The resulting yellow solution is permitted to stir for 15 h at which time it is concentrated in vacuo and the resulting residue is dissolved in glacial acetic acid (130 mL) and placed at reflux for 4 h. The reaction mixture is then cooled to room temperature and concentrated to dryness in vacuo. The reaction mixture is then purified by silica gel flash chromatography [(6% ethyl acetate/0.08% acetic acid/93.92% dichloromethane) to (18% ethyl acetate/0.24% acetic acid/81.76% dichloromethane)] to afford 2-cyclopropyl-3,3-dimethyl-1-oxo-1,2,3,4-tetrahydro-isoquinoline-4-carboxylic acid as an off-white powder; MS (ESI) m/z 260.1 (M+H).

(b) 2-Cyclopropyl-4-hydroxy-3,3-dimethyl-3,4-dihydro-2H-isoquinolin-1-one

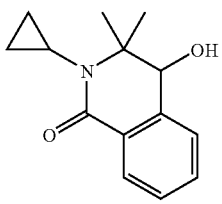

To a solution of 2-cyclopropyl-3,3-dimethyl-1-oxo-1,2,3,4-tetrahydro-isoquinoline-4-carboxylic acid (4.1 g, 15.8 mmol) in acetic acid (300 mL) is added benzene (150 mL), potassium acetate (10.9 g, 111 mmol), cupric acetate (0.145 g, 0.8 mmol) and lead (IV) acetate (12.7 g, 28.6 mmol). The green reaction mixture is heated to reflux for 2.5 h. The reaction mixture is then cooled to room temperature and quenched by the addition of ethylene glycol (ca. 6 mL). The resulting solution is the concentrated in vacuo to near dryness. The resulting dark green oil is dissolved in ethyl acetate (ca. 500 mL) and stirred vigorously while cautiously treating with saturated aqueous sodium bicarbonate (ca. 200 mL), followed by solid $NaHCO_3$ until the aqueous layer reached a pH greater than 8. The layers are separated and the aqueous layer is extracted three times with ethyl acetate. The organic layer is dried with $Na_2SO_4$ filtered and concentrated. The resulting brown oil is then dissolved in THF (150 mL). Water (30 ml) and LiOH $H_2O$ (3.5 g, 83.4 mmol) are added. The reaction mixture is placed at 45° C. for 18 h, whereupon it is cooled to room temperature. The reaction is concentrated in vacuo to ca. ¾ of its original volume, diluted with methylene chloride and saturated aqueous $NaHCO_3$. The layers are separated and the aqueous layer is extracted three times with ethyl acetate. The organic layers are combined, dried with $Na_2SO_4$, filtered and concentrated in vacuo to afford a brown oil. Purification by silica gel flash chromatography (ethyl acetate-dichloromethane, 1:19 to 1:4) gave 2-cyclopropyl-4-hydroxy-3,3-dimethyl-3,4-dihydro-2H-isoquinolin-1-one as an off-white solid; MS (ESI) m/z 232.1 (M+H).

(c) 3-(2-cyclopropyl-3,3-dimethyl-1-oxo-1,2,3,4-tetrahydro-isoquinolin-4-yl)-3H-imidazole-4-carboxylic Acid Methyl Ester

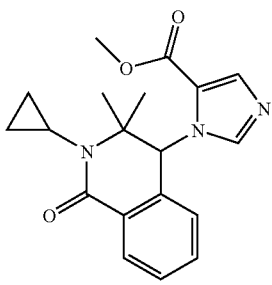

To a solution of 2-cyclopropyl-4-hydroxy-3,3-dimethyl-3,4-dihydro-2H-isoquinolin-1-one (2.25 g, 9.72 mmol) in THF (100 mL) is added triphenylphosphine (4.3 g, 16.5 mmol), and methyl-4-imidazolecarboxylate (2.08 g, 16.5 mmol). The heterogeneous reaction mixture is cooled to 0° C. and di-tert-butyl azodicarboxylate (3.81 g, 16.5 mmol) is added. The reaction is allowed to warm to room temperature and stirred for 45 min, and then heated at 44° C. for an additional 75 min, at which time the reaction is cooled to 0° C. and 4M HCl in dioxane (20 mL, 80 mmol) is added. The reaction is brought to room temperature and allowed to stir for 1 h. The reaction mixture is then basified to a pH of ca. 9 via the cautious addition of saturated aqueous $NaHCO_3$. The resulting mixture is further diluted with ethyl acetate and saturated aqueous $NaHCO_3$, and the layers are separated. The aqueous layer is extracted three times with ethyl acetate and the organic layers are combined, dried over $Na_2SO_4$, filtered and concentrated in vacuo. The resulting residue is adsorbed onto silica gel and submitted to silica gel flash chromatography (ethyl acetate-dichloromethane, 1:24 to 1:4) to provide 3-(2-cyclopropyl-3,3-dimethyl-1-oxo-1,2,3,4-tetrahydro-isoquinolin-4-yl)-3H-imidazole-4-carboxylic acid methyl ester as an off-white solid; HRMS (ESI) m/z 340.1668 [(M+H)$^+$; calculated for $C_{19}H_{22}N_3O_3$: 340.1661]; $^1$H NMR (400 MHz, CHLOROFORM-D) δ ppm 0.34-0.45 (m, 1 H), 0.78-0.88 (m, 1 H), 0.90-0.99 (m, 1 H), 1.05-1.16 (m, 1 H), 1.31 (s, 3 H), 1.45 (s, 3 H), 2.29-2.43 (m, 1 H), 3.94 (s, 3 H), 6.55 (s, 1 H), 7.28-7.33 (m, 2 H), 7.44-7.55 (m, 2 H), 7.78 (s, 1 H), 8.17-8.29 (m, 1 H)

Example 33

(a) 3,3-Dimethyl-1-oxo-1,2,3,4-tetrahydro-isoquinoline-4-carboxylic Acid

To 2-(3,4-dimethoxy-benzyl)-3,3-dimethyl-1-oxo-1,2,3,4-tetrahydro-isoquinoline-4-carboxylic acid (9.6 g, 26 mmol), prepared in manner analogous to 2-cyclopropyl-3,3-dimethyl-1-oxo-1,2,3,4-tetrahydro-isoquinoline-4-carboxylic acid, is added thioanisole (36 mL, 304 mmol) and trifluoroacetic acid (360 mL). The resulting solution is heated to 70° C. for 13 h. The reaction is then cooled to room temperature and concentrated in vacuo to near dryness. The resulting purple oil is purified via silica gel flash chromatography (dichloromethane-methanol, 1:0 to 9:1, with 0.5% acetic acid) to furnish 3,3-dimethyl-1-oxo-1,2,3,4-tetrahydro-isoquinoline-4-carboxylic acid as an off-white foam; MS (ESI) m/z 220.0 (M+H).

(b) 4-Hydroxy-3,3-dimethyl-3,4-dihydro-2H-isoquinolin-1-one

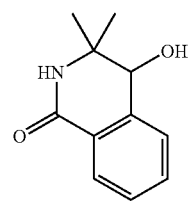

To a solution of 3,3-dimethyl-1-oxo-1,2,3,4-tetrahydro-isoquinoline-4-carboxylic acid (5.0 g, 22.8 mmol) in acetic acid (450 mL) and benzene (160 mL) is added successively, potassium acetate (15.7 g, 160 mmol), cupric acetate (210 mg, 1.14 mmol), and lead (IV) acetate (18.2 g, 41.1 mmol). The green solution is heated to reflux for 4 h, at which time additional lead (IV) acetate (2.0 g 4.5 mmol) is added. After a total of 5 h at reflux the reaction is cooled to room temperature and quenched by the addition of ethylene glycol (ca. 5 mL). The reaction is concentrated in vacuo to near dryness. The resulting dark green oil is dissolved in ethyl acetate and stirred vigorously while cautiously treating with saturated aqueous sodium bicarbonate followed by solid NaHCO₃ until the aqueous layer reached a pH greater than 8. The layers are separated and the aqueous layer is extracted 3 times with ethyl acetate. The organic layer is dried with Na₂SO₄ filtered and concentrated. The resulting brown oil is then dissolved in THF (200 mL). Water (40 ml) and LiOH.H₂O (5.0 g, 118.6 mmol) are added. The reaction mixture is heated to 45° C. and stirred for 18 h, at which time it is cooled to room temperature. The reaction is concentrated in vacuo to ca. ¾ of its original volume, diluted with methylene chloride and saturated aqueous NaHCO₃. The layers are separated and the aqueous layer is extracted 3 times with ethyl acetate. The organic layers are combined, dried with Na₂SO₄, filtered and concentrated in vacuo to afford a brown oil, which is pre-adsorbed on silica gel for further purification. Purification by silica gel flash chromatography (dichloromethane-methanol, 99:1 to 23:2) furnished 4-hydroxy-3,3-dimethyl-3,4-dihydro-2H-isoquinolin-1-one as an off-white foam; MS (ESI) m/z 192.1 (M+H).

(c) 3-(3,3-Dimethyl-1-oxo-1,2,3,4-tetrahydro-isoquinolin-4-yl)-3H-imidazole-4-carboxylic Acid Methyl Ester

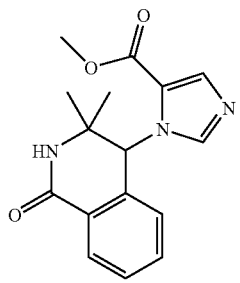

To a solution of 4-hydroxy-3,3-dimethyl-3,4-dihydro-2H-isoquinolin-1-one (1.15 g, 6.0 mmol) in THF (85 mL) is added triphenylphosphine (2.7 g, 10.2 mmol), and methyl-4-imidazolecarboxylate (1.3 g, 10.2 mmol). The heterogeneous reaction mixture is cooled to 0° C. and di-tert-butyl azodicarboxylate (2.4 g, 10.2 mmol) is added. The reaction is allowed to warm to room temperature and stirred for 45 min, and then heated at 40° C. for an additional 75 min, at which time the reaction is cooled to 0° C. and 4M HCl in dioxane (20 mL, 80 mmol) is added. The reaction is brought to room temperature and allowed to stir for 45 min. The reaction mixture is then basified to a pH of ca. 8 via the cautious addition of saturated aqueous NaHCO₃. The resulting mixture is further diluted with ethyl acetate and saturated aqueous NaHCO₃ and the layers are separated. The aqueous layer is extracted 3 times with ethyl acetate and the organic layers are combined, dried over Na₂SO₄, filtered and concentrated in vacuo. The resulting residue is adsorbed onto silica gel and submitted to silica gel flash chromatography [35 to 60% of a stock solution in hexanes (stock solution is made of 17% v/v reagent alcohol in ethyl acetate)] to provide 3-(3,3-dimethyl-1-oxo-1,2,3,4-tetrahydro-isoquinolin-4-yl)-3H-imidazole-4-carboxylic acid methyl ester as an off-white solid. HRMS (ESI) m/z 300.1354 [(M+H)⁺; calculated for C₁₆H₁₈N₃O₃: 340.1348]; ¹H NMR (400 MHz, CHLOROFORM-d) δ ppm 1.07 (s, 3 H), 1.45 (s, 3 H), 3.94 (s, 3 H), 5.72 (br. s., 11 H), 6.59 (s, 1 H), 7.32-7.38 (m, 1 H), 7.41 (s, 1 H), 7.50-7.61 (m, 2 H), 7.78 (s, 1 H), 8.19-8.28 (m, 1 H).

(d) 3-(2,3,3-Trimethyl-1-oxo-1,2,3,4-tetrahydro-isoquinolin-4-yl)-3H-imidazole-4-carboxylic Acid Methyl Ester

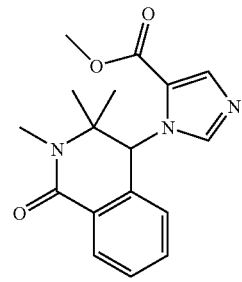

To a solution of 3-(3,3-dimethyl-1-oxo-1,2,3,4-tetrahydro-isoquinolin-4-yl)-3H-imidazole-4-carboxylic acid methyl ester (55 mg, 0.184 mmol) in DMF (3.7 mL) at −10° C. is added sodium hydride (60% dispersion in oil 10 mg, 0.25 mmol). The reaction is stirred for 5 min at −10° C. and then placed at room temperature for 10 min. The resulting red solution is re-cooled to −10° C. and methyl iodide (0.025 mL, 0.40 mmol) is added dropwise. The reaction is placed at room temperature. After 10 min the yellow reaction mixture is quenched by the addition of saturated aqueous NH₄Cl (ca. 1 mL). The resulting mixture is diluted with ethyl acetate and saturated aqueous NaHCO₃. The layers are separated and the aqueous layer is extracted twice with ethyl acetate (ca. 10 mL). The organic layers are combined, dried with Na₂SO₄, filtered and concentrated in vacuo to afford 3-(2,3,3-trimethyl-1-oxo-1,2,3,4-tetrahydro-isoquinolin-4-yl)-3H-imidazole-4-carboxylic acid methyl ester as a yellow foam requiring no further purification prior to the next transformation; HRMS (ES) m/z 300.1354 [(M+H)⁺; calculated for C₁₆H₁₈N₃O₃: 340.1348]; ¹H NMR (400 MHz, MeOD) δ ppm 1.30 (s, 3H), 1.41 (s, 3 H), 3.10 (s, 3 H), 4.04 (br. s., 3 H), 6.85 (br. s., 1 H), 7.50 (br. s., 1 H), 7.61-7.73 (m, 2 H), 8.09-8.27 (m, 3 H).

(e) 4-(5-Hydroxymethyl-imidazol-1-yl)-2,3,3-trimethyl-3,4-dihydro-2H-isoquinolin-1-one

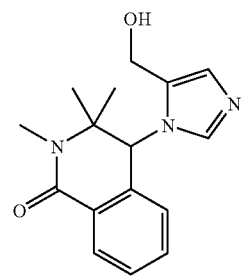

To a solution of 3-(2,3,3-trimethyl-1-oxo-1,2,3,4-tetrahydro-isoquinolin-4-yl)-3H-imidazole-4-carboxylic acid methyl ester (190 mg, 0.367 mmol) in THF (5.5 mL) at −25° C. is added lithium aluminum hydride (18 mg, 0.48 mmol). The reaction is permitted to warm to 0° C. over 2 h and the reaction is stirred for an additional 30 min at 0° C. After a total of 2.5 h the reaction is quenched at 0° C. by the consecutive addition of 9:1 THF/H₂O (0.225 mL), 2M aqueous NaOH (0.090 mL), and H$_2$O (0.170 mL). The reaction is warmed to room temperature and diluted with THF (2.0 mL). After addition of MgSO$_4$ (250 mg), the heterogeneous mixture is stirred for 15 min and then filtered through a pad of Celite. The pad of Celite is washed with ethyl acetate and the combined filtrate is concentrated in vacuo. The resulting residue is purified by silica gel flash chromatography (dichloromethane-methanol, 49:1 to 9:1) to afford 4-(5-hydroxymethyl-imidazol-1-yl)-2,3,3-trimethyl-3,4-dihydro-2H-isoquinolin-1-one as a colorless foam. High resolution mass spectrum (ES+) m/z 286.1547 [(M+H)$^+$; calculated for C$_{16}$H$_{20}$N$_3$O$_2$: 286.1556]; $^1$H NMR (400 MHz, CHLOROFORM-d) δ ppm 1.22 (s, 3 H), 1.36 (s, 3 H), 2.12 (br. s, 1 H), 3.11 (s, 3 H), 4.65-4.95 (m, 2 H), 5.33 (s, 1 H), 6.95 (s, 1 H), 7.31-7.36 (m, 1 H), 7.37 (s, 1 H), 7.43-7.54 (m, 2 H), 8.18-8.25 (m, 1 H).

(f) (R)- and (S)-4-(S-Hydroxymethyl-imidazol-1-yl)-2,3,3-trimethyl-3,4-dihydro-2H-isoquinolin-1-one Resolution of the enantiomers of the title compound is achieved by chiral HPLC using the ChiralPak AD-H column with a 1:4 ethanol-heptane mobile phase to give enantiomer A (t$_r$=12.3 min) and enantiomer B (t$_r$=19.1 min).

Example 34

(a) 4-(5-hydroxymethyl-imidazol-1-yl)-3,3-dimethyl-3,4-dihydro-2H-isoquinolin-1-one

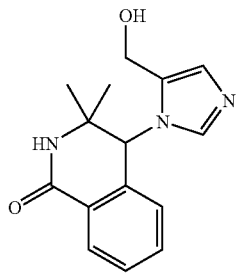

To a solution of 3-(3,3-dimethyl-1-oxo-1,2,3,4-tetrahydro-isoquinolin-4-yl)-3H-imidazole-4-carboxylic acid methyl ester (200 mg, 0.67 mmol) (Example 33c) in THF (20 mL) at −10° C. is added lithium aluminum hydride (56 mg, 1.47 mmol). After stirring for 5 min the reaction is placed at room temperature for 1 h, at which time the reaction is cooled to 0° C. and quenched by the consecutive addition of 9:1 THF/H$_2$O (0.8 mL), 2M aqueous NaOH (0.92 mL), and H$_2$O (0.6 mL). The reaction is then warmed to room temperature and diluted with THF (6 mL). After the addition of MgSO$_4$ (900 mg), the heterogeneous mixture is stirred for 15 min and then filtered through a pad of Celite®. The pad of Celite® is washed with ethyl acetate and the combined filtrate is concentrated. The resulting residue is purified by silica gel flash chromatography (ethyl acetate-hexanes-ethanol, 6.5:2.5:1 to 9:0.5:1.2) to furnish 4-(5-hydroxymethyl-imidazol-1-yl)-3,3-dimethyl-3,4-dihydro-2H-isoquinolin-1-one; MS (ESI) m/z 272.0 (M+H); $^1$H NMR (400 MHz, CHLOROFORM-d) δ ppm 1.11 (s, 3 H), 1.42 (s, 3 H), 2.25 (br. s., 1 H), 4.61-4.93 (m, 2 H), 5.40 (s, 1 H), 5.73 (br. s., 1 H), 6.96 (s, 1 H), 7.32-7.37 (m, 1 H), 7.38 (s, 1 H), 7.46-7.56 (m, 2 H), 8.15-8.26 (m, 1 H).

(b) (R) and (S)-4-(5-hydroxymethyl-imidazol-1-yl)-3,3-dimethyl-3,4-dihydro-2H-isoquinolin-1-one The resolution of the enantiomers the title compound is achieved by chiral HPLC using a ChiralPak IA column with 4.1 heptanes-reagent alcohol to give enantiomer A (t$_r$=8.3 min) and enantiomer B (t$_r$=8.8 min).

Example 35

(a) 3-(2-Ethyl-3,3-dimethyl-1-oxo-1,2,3,4-tetrahydro-isoquinolin-4-yl)-3H-imidazole-4-carboxylic Acid Methyl Ester

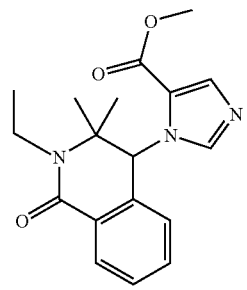

To a solution of 3-(3,3-dimethyl-1-oxo-1,2,3,4-tetrahydro-isoquinolin-4-yl)-3H-imidazole-4-carboxylic acid methyl ester (114 mg, 0.381 mmol) (Example 33c) in DMF (6 mL) at −10° C. is added NaH [60% dispersion in oil (20 mg, 0.5 mmol)]. The reaction is stirred at −10° C. for 10 min, placed at room temperature for 5 min, and then recooled to −10° C., at which time ethyl iodide (0.070 mL, 0.875 mmol) is added. After 45 min the reaction is quenched with saturated aqueous NH$_4$Cl, diluted with ethyl acetate and saturated aqueous NaHCO$_3$. The layers are separated and the aqueous layer is extracted two more times with ethyl acetate. The combined organic layers are dried over Na$_2$SO$_4$, filtered, and concentrated. The resulting residue is purified by silica gel flash chromatography (ethyl acetate-dichloromethane, 1:7 to 1:0) to afford 3-(2-ethyl-3,3-dimethyl-1-oxo-1,2,3,4-tetrahydro-isoquinolin-4-yl)-3H-imidazole-4-carboxylic acid methyl ester; HRMS: (ESI) m/z 328.1673 [(M+H)$^+$: Calcd for C$_{18}$H$_{22}$N$_3$O$_3$: 328.1661]; $^1$H NMR (400 MHz, CHLOROFORM-d) δ ppm 1.21 (t, J=7.1 Hz, 3 H), 1.24 (s, 3 H), 1.40 (s, 3 H), 3.47-3.57 (m, 1 H), 3.67-3.78 (m, 1H), 3.94 (s, 3 H), 6.56 (s, 1 H), 7.28-7.33 (m, 1 H), 7.42 (s, 1 H), 7.46-7.55 (m, 2 H), 7.77 (s, 1 H), 8.20-8.26 (m, 1 H).

(b) (R)- and (S)-3-(2-Ethyl-3,3-dimethyl-1-oxo-1,2,3,4-tetrahydro-isoquinolin-4-yl)-3H-imidazole-4-carboxylic Acid Methyl Ester The resolution of the enantiomers the title compound is achieved by chiral HPLC using a ChiralPak OD column with 9:1 heptanes-reagent alcohol to give enantiomer A (t$_r$=15.3 min) and enantiomer B (t$_r$=19.0 min).

Example 36

(a) 2,2-Dimethyl-indan-1,3-dione (CAS# 17190-77-1)

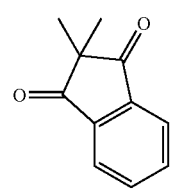

Potassium fluoride on Celite® [loading wt: 50% purchased from Sigma-Aldrich Co.] (5.8 g, ~50 mmol) is heated at 135°

C. for 2 h under vacuum (<20 torr). The solid is then permitted to cool to room temperature and placed under a nitrogen atmosphere at which time a solution of indan-1,3-dione (CAS# 606-23-5, 1.46 g, 10.0 mmol) in acetonitrile (15 mL) is added followed by iodomethane (1.8 mL, 30 mmol). The reaction is heated in a sealed vessel at 70° C. overnight. The reaction mixture is cooled to room temperature and filtered through a pad of Celite®. The resulting residue is purified by silica gel flash chromatography (ethyl acetate-heptane, 0:1 to 1:9) to furnish 2,2-dimethyl-indan-1,3-dione; $^1$H NMR (400 MHz, CHLOROFORM-d) δ ppm 1.30 (s, 6 H), 7.84-7.89 (m, 2 H), 7.96-8.02 (m, 2 H).

(b) 3-Hydroxy-2,2-dimethyl-indan-1 one (CAS# 59269-93-1)

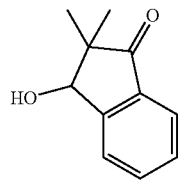

To a solution of 2,2-dimethyl-indan-1,3-dione (430 mg, 2.47 mmol), in ethanol (80 mL) at −30° C. is added a solution of NaBH$_4$ (29 mg, 0.74 mmol) in ethanol (3 mL). After one h the reaction is quenched with saturated aqueous NH$_4$Cl and the mixture is brought to room temperature. The reaction mixture is concentrated to approximately half of its original volume and then diluted with ethyl acetate and washed with water. The aqueous layer is then back-extracted twice with ethyl acetate. The organic layers are combined, dried with Na$_2$SO$_4$, filtered, and concentrated. The resulting residue is purified by silica gel flash chromatography (ethyl acetate-heptane, 0:1 to 1:6) to afford 3-hydroxy-2,2-dimethyl-indan-1-one; MS (ESI) m/z 177.0 (M+H)$^+$.

(c) 3-Imidazol-1-yl-2,2-dimethyl-indan-1-one

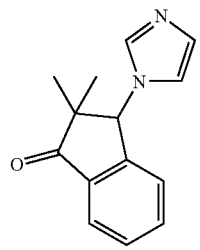

To a solution of trifluoromethansulfonic anhydride (1.13 mL, 6.75 mmol) in dichloromethane (10 mL) at −78° C. is added, via cannula, a solution of diisopropylethylamine (1.8 mL, 10.1 mmol) and 3-hydroxy-2,2-dimethyl-indan-1-one, prepared as described in Example 8c, (400 mg, 2.25 mmol) in dichloromethane (5 mL). The reaction is stirred at −78° C. for 10 min and then is placed at −10° C. for 10 min. The reaction is then re-cooled to −7.8° C. and a solution of imidazole (920 mg, 13.5 mmol) in dichloromethane (12 mL) is added via cannula. The reaction is then placed at room temperature for 1 h, at which time it is diluted with saturated aqueous NaHCO$_3$ and ethyl acetate. The layers are separated and the aqueous layer is extracted twice with ethyl acetate. The combined organic layers are dried with MgSO$_4$, filtered, and concentrated. The resulting residue is purified by silica gel flash chromatography (ethyl acetate-dichloromethane, 1:3 to 1:0) to afford 3-imidazol-1-yl-2,2-dimethyl-indan-1-one; MS (ESI) m/z 227 (M+H)$^+$; $^1$H NMR: (400 MHz, CHLOROFORM-d) δ ppm 0.80 (s, 3 H), 1.41 (s, 3 H), 5.52 (s, 1 H), 6.73 (s, 1 H), 7.12 (s, 1 H), 7.51 (d, J=7.6 Hz, 1 H), 7.56 (s, 1 H), 7.62 (t, J=7.5 Hz, 1 H), 7.70-7.80 (m, 1 H), 7.91 (d, J=7.6 Hz, 1 H).

(d) 4-Imidazol-1-yl-3,3-dimethyl-3,4-dihydro-2H-isoquinolin-1-one

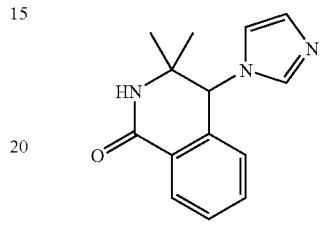

To a solution of 3-imidazol-1-yl-2,2-dimethyl-indan-1-one (350 mg, 1.55 mmol) in methanol (19 mL) is added pyridine (1.6 mL, 19.6 mmol) and then hydroxylamine hydrochloride (270 mg, 3.9 mmol). The reaction is stirred at 55° C. for ca. 14 h and then cooled to room temperature. The reaction is concentrated in vacuo to ca. half of the original volume. The mixture is then diluted with ethyl acetate and 50% saturated aqueous NaCl. The layers are separated and the aqueous layer is extracted two additional times with ethyl acetate. The organic layers are combined, dried over Na$_2$SO$_4$, filtered, and concentrated. The resulting residue is dissolved in pyridine (10 mL) and placed at 0° C. The solution is charged with DMAP (ca. 6 mg, 0.05 mmol) and p-toluenesulfonyl chloride (615 mg, 3.22 mmol), and placed at room temperature for 1 h. The reaction is then warmed to 50° C. and stirred for ca. 14 h. The reaction is then cooled to room temperature, diluted with saturated aqueous NaHCO$_3$ and ethyl acetate. The layers are separated and the organic layer is washed with brine, dried over Na$_2$SO$_4$, filtered, and concentrated. The resulting residue is dissolved in pyridine (11 mL) and heated by microwave irradiation at 190° C. for 35 min in a sealed vessel. The reaction is cooled to room temperature quenched with saturated aqueous NaHCO$_3$ (ca. 0.5 mL) and diluted with ethyl acetate. The mixture is then dried with Na$_2$SO$_4$, filtered, and concentrated. The resulting residue is purified by silica gel flash chromatography (methanol-dichloromethane, 0:1 to 1:10) to provide 4-imidazol-1-yl-3,3-dimethyl-3,4-dihydro-2H-isoquinolin-1-one; HRMS (ESI) m/z 242.1293 [(M+H)$^+$; Calcd for C$_{14}$H$_{16}$N$_3$O: 242.1293]; $^1$H NMR (400 MHz, CHLOROFORM-d) δ ppm 1.15 (s, 3 H), 1.40 (s, 3 H), 5.09 (s, 1 H), 5.73 (br. s., 1 H), 6.82 (s, 1 H), 7.04 (s, 1 H), 7.21-7.26 (m, 1 H), 7.50-7.60 (m, 3 H), 8.17-8.26 (m, 1 H).

(e) (R)- and (S)-4-Imidazol-1-yl-3,3-dimethyl-3,4-dihydro-2H-isoquinolin-1-one

The resolution of the enantiomers the title compound is achieved by chiral HPLC using a ChiralPak AS-H column with 83:17 heptanes-isopropyl alcohol to give enantiomer A (t$_r$=23.0 min) and enantiomer B (t$_r$=26.0 min).

Example 37

(a) 4-Imidazol-1-yl-2,3,3-trimethyl-3,4-dihydro-2H-isoquinolin-1-one

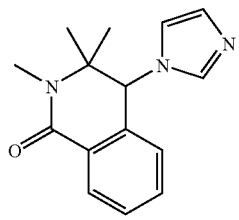

To a solution of 4-imidazol-1-yl-3,3-dimethyl-3,4-dihydro-2H-isoquinolin-1-one, which can be prepared as described in Example 36d (140 mg, 0.58 mmol) in DMF (8 mL) at −10° C. is added NaH [60% dispersion in oil (30 mg, 0.75 mmol)]. After 10 min, the reaction is warmed to room temperature for 5 min and then re-cooled to −10° C. The reaction is then charged with methyl iodide (0.075 mL, 1.2 mmol) and placed at room temperature. After 20 min, the reaction is cooled to −10° C., quenched with saturated aqueous $NH_4Cl$, and diluted with saturated aqueous $NaHCO_3$ and ethyl acetate. The layers are separated and the aqueous layer is extracted two times with ethyl acetate. The combined organic layers are dried over $Na_2SO_4$, filtered, and concentrated. The resulting residue is purified by silica gel flash chromatography (methanol-dichloromethane, 0:1 to 1:12) to afford 4-imidazol-1-yl-2,3,3-trimethyl-3,4-dihydro-2H-isoquinolin-1-one; HRMS (ESI) m/z 256.1448 [(M+H)$^+$: Calcd for $C_{15}H_{18}N_3O$: 256.1450]; $^1$H NMR (400 MHz, CHLOROFORM-d) δ ppm 1.22 (s, 3 H), 1.33 (s, 3 H), 3.09 (s, 3 H), 5.01 (s, 1 H), 6.78 (s, 1 H), 7.02 (s, 1 H), 7.20 (d, J=3.8 Hz, 1 H), 7.47-7.57 (m, 3 H), 8.20-8.28 (m, 1 H).

(b) (R)- and (S)-4-imidazol-1-yl-2,3,3-trimethyl-3,4-dihydro-2H-isoquinolin-1-one The resolution of the enantiomers of the title compound is achieved by chiral HPLC using a ChiralPak AS-H column with 85:15 heptanes: reagent alcohol to give enantiomer A ($t_r$=10.9 min) and enantiomer B ($t_r$=22.9 min).

We claim:

1. A compound of formula (I):

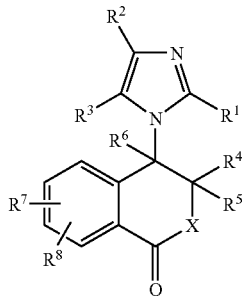

(I)

wherein,
X is oxygen;
$R^1$ is hydrogen;
$R^2$ is hydrogen;
$R^3$ is $R^{12}R^{11}(R^{13}O)C—$;
$R^4$ and $R^5$ are independently $(C_1-C_4)$ alkyl;
$R^6$ is hydrogen;
$R^7$ is hydrogen;
$R^8$ is hydrogen or halogen;
$R^{11}$ and $R^{12}$ are independently hydrogen;
$R^{13}$ is hydrogen or $(C_1-C_6)$ alkyl;
or pharmaceutically acceptable salts thereof; or an optical isomer thereof; or a mixture of optical isomers.

2. A compound of formula (I):

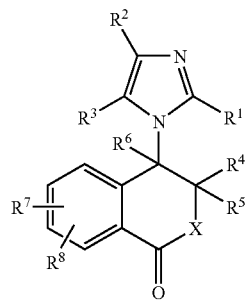

(I)

wherein
X is oxygen;
$R^1$ is hydrogen;
$R^2$ is hydrogen;
$R^3$ is hydrogen or $(C_1-C_7)$ alkyl that is optionally substituted by one to four substituents selected from halogen, amino, mono-$(C_1-C_7)$ alkylamino, and di-$(C_1-C_7)$ alkylamino;
$R^4$ and $R^5$ are independently $(C_1-C_7)$ alkyl;
$R^6$ is hydrogen;
$R^7$ and $R^8$ are independently hydrogen, halogen, cyano, nitro, mono-$(C_1-C_7)$ alkylamino or di-$(C_1-C_7)$ alkylamino;
or a pharmaceutically acceptable salt thereof; or an optical isomer thereof; or a mixture of optical isomers.

3. A compound of formula I according to claim 1, which is 4-(5-hydroxymethyl-imidazol-1-yl)-3,3-dimethyl-isochroman-1-one.

4. A compound of formula I according to claim 2, which is 4-(5-difluoromethyl-imidazol-1-yl)-3,3-dimethyl-isochroman-1-one.

5. A compound of formula I according to claim 2, which is 6-fluoro-4-imidazol-1-yl-3,3-dimethyl-isochroman-1-one.

6. A compound of formula I according to claim 2, which is 7-fluoro-4-imidazol-1-yl-3,3-dimethyl-isochroman-1-one.

7. A method of inhibiting aldosterone synthase activity in a subject, wherein the method comprises administering to the subject a therapeutically effective amount of the compound of formula (I) according to claim 1.

8. A method of inhibiting aldosterone synthase activity in a subject, wherein the method comprises administering to the subject a therapeutically effective amount of the compound of formula (I) according to claim 2.

9. A method of treating a disorder or a disease selected from hypokalemia, hypertension, congestive heart failure, renal failure, restenosis, atherosclerosis, syndrome X, obesity, nephropathy, post-myocardial infarction, coronary heart diseases, increased formation of collagen, cardiac fibrosis and remodeling following hypertension and endothelial dysfunction in a subject, wherein the method comprises administering to the subject a therapeutically effective amount of the compound of formula (I) according to claim 1.

10. A method of treating a disorder or a disease selected from hypokalemia, hypertension, congestive heart failure, renal failure, restenosis, atherosclerosis, syndrome X, obesity, nephropathy, post-myocardial infarction, coronary heart diseases, increased formation of collagen, cardiac fibrosis and remodeling following hypertension and endothelial dysfunction in a subject, wherein the method comprises administering to the subject a therapeutically effective amount of the compound of formula (I) according to claim 2.

11. A pharmaceutical composition comprising a therapeutically effective amount of a compound of formula (I) according to claim 1 and one or more pharmaceutically acceptable carriers.

12. A pharmaceutical composition comprising a therapeutically effective amount of a compound of formula (I) according to claim 2 and one or more pharmaceutically acceptable carriers.

* * * * *